US009408825B2

(12) United States Patent
Lephart et al.

(10) Patent No.: US 9,408,825 B2
(45) Date of Patent: Aug. 9, 2016

(54) USE OF EQUOL FOR TREATING ANDROGEN MEDIATED DISEASES

(71) Applicants: Edwin Douglas Lephart, Orem, UT (US); Trent D. Lund, Wheaton, IL (US); Robert J. Handa, Fort Collins, CO (US)

(72) Inventors: Edwin Douglas Lephart, Orem, UT (US); Trent D. Lund, Wheaton, IL (US); Robert J. Handa, Fort Collins, CO (US)

(73) Assignees: BRIGHAM YOUNG UNIVERSITY, Provo, UT (US); COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 0 days.

(21) Appl. No.: 14/810,117

(22) Filed: Jul. 27, 2015

(65) Prior Publication Data
US 2015/0342924 A1    Dec. 3, 2015

Related U.S. Application Data

(63) Continuation of application No. 13/903,748, filed on May 28, 2013, now Pat. No. 9,089,547, which is a continuation of application No. 13/442,466, filed on Apr. 9, 2012, now Pat. No. 8,450,364, which is a continuation of application No. 12/572,791, filed on Oct. 2, 2009, now Pat. No. 8,153,684, which is a continuation of application No. 10/533,045, filed as application No. PCT/US03/34441 on Oct. 29, 2003, now abandoned.

(60) Provisional application No. 60/422,469, filed on Oct. 29, 2002.

(51) Int. Cl.
A61K 31/352 (2006.01)
A23L 1/30 (2006.01)
A61K 31/35 (2006.01)
A61K 31/353 (2006.01)

(52) U.S. Cl.
CPC .............. *A61K 31/352* (2013.01); *A23L 1/30* (2013.01); *A61K 31/35* (2013.01); *A61K 31/353* (2013.01); *A23V 2002/00* (2013.01)

(58) Field of Classification Search
CPC .................................................. A61K 31/352
See application file for complete search history.

(56) References Cited

U.S. PATENT DOCUMENTS

| | | | |
|---|---|---|---|
| 4,390,559 A | 6/1983 | Zilliken |
| 4,814,346 A | 3/1989 | Albert et al. |
| 5,141,746 A | 8/1992 | Fleury et al. |
| RE34,457 E | 11/1993 | Okamoto et al. |
| 5,352,384 A | 10/1994 | Shen |
| 5,424,331 A | 6/1995 | Shlyankevich |
| 5,468,501 A | 11/1995 | Kydonieus et al. |
| 5,498,631 A | 3/1996 | Gorbach et al. |
| 5,523,087 A | 6/1996 | Shlyankevich |
| 5,613,958 A | 3/1997 | Kochinke et al. |
| 5,693,018 A | 12/1997 | Kriesel et al. |
| 5,726,034 A | 3/1998 | Bryan et al. |
| 5,733,926 A | 3/1998 | Gorbach |
| 5,804,234 A | 9/1998 | Suh et al. |
| 5,830,887 A | 11/1998 | Kelly |
| 5,848,991 A | 12/1998 | Gross et al. |
| 5,849,798 A | 12/1998 | Charpentier et al. |
| 5,855,892 A | 1/1999 | Potter et al. |
| 5,942,539 A | 8/1999 | Hughes, Jr. et al. |
| 5,952,374 A | 9/1999 | Clarkson et al. |
| 5,958,946 A | 9/1999 | Styczynski et al. |
| 5,990,291 A | 11/1999 | Waggle et al. |
| 6,004,558 A | 12/1999 | Thurn et al. |
| 6,020,471 A | 2/2000 | Johns et al. |
| 6,054,636 A | 4/2000 | Fader |
| 6,060,070 A | 5/2000 | Gorbach |
| 6,083,526 A | 7/2000 | Gorbach |
| 6,146,668 A | 11/2000 | Kelly et al. |
| 6,159,959 A | 12/2000 | Miller |
| 6,194,450 B1 | 2/2001 | Charpentier et al. |
| 6,242,594 B1 | 6/2001 | Kelly |

(Continued)

FOREIGN PATENT DOCUMENTS

AU    20006896 A4    5/2000
CA    2389560    11/2002

(Continued)

OTHER PUBLICATIONS

Aldercreutz, H., et al., "Urinary Excretion of Lignans and Isoflavonoid Phytoestrogens in Japanese Men and Women Consuming a Traditional Japanese Diet," *Am. J. Clin. Nutr.*, 54:1093-1100 (1991).

(Continued)

*Primary Examiner* — Paul Zarek

(74) *Attorney, Agent, or Firm* — Brinks Gilson & Lione

(57) ABSTRACT

Equol (7-hydroxy-3(4'hydroxyphenyl)-chroman), the major metabolite of the phytoestrogen daidzein, specifically binds and blocks the hormonal action of 5α-dihydrotestosterone (DHT) in vitro and in vivo. Equol can bind circulating free DHT and sequester it from the androgen receptor, thus altering growth and physiological hormone responses that are regulated by androgens. These data suggest a novel model to explain equol's biological properties. The significance of equol's ability to specifically bind and sequester DHT from the androgen receptor have important ramifications in health and disease and may indicate a broad and important usage for equol in the treatment and prevention of androgen-mediated pathologies. Thus, equol can specifically bind DHT and prevent DHT's biological actions in physiological and pathophysiological processes.

5 Claims, 61 Drawing Sheets

(56) References Cited

U.S. PATENT DOCUMENTS

| | | | |
|---|---|---|---|
| 6,258,856 | B1 | 7/2001 | Chamberlain et al. |
| 6,326,366 | B1 | 12/2001 | Potter et al. |
| 6,340,703 | B1 | 1/2002 | Kelly |
| 6,375,994 | B1 | 4/2002 | Paul et al. |
| 6,455,032 | B1 | 9/2002 | Kelly et al. |
| 6,497,906 | B1 | 12/2002 | Kelly |
| 6,509,043 | B1 | 1/2003 | Hoie |
| 6,518,301 | B1 | 2/2003 | Barlaam et al. |
| 6,544,566 | B1 | 4/2003 | Waggle et al. |
| 6,562,380 | B1 | 5/2003 | Kelly |
| 6,565,864 | B2 | 5/2003 | Pillai et al. |
| 6,599,536 | B1 | 7/2003 | Kelly et al. |
| 6,638,543 | B2 | 10/2003 | Kang et al. |
| 6,642,212 | B1 | 11/2003 | Kelly |
| 6,649,648 | B1 | 11/2003 | Kelly et al. |
| 6,716,424 | B1 | 4/2004 | Uchiyama et al. |
| 7,396,855 | B2 | 7/2008 | Sechell et al. |
| 7,960,432 | B2 * | 6/2011 | Setchell ............ A23L 1/30 514/456 |
| 8,580,846 | B2 * | 11/2013 | Lephart ............ A61K 31/35 424/400 |
| 8,668,914 | B2 * | 3/2014 | Lephart ............ A61K 8/498 424/401 |
| 9,018,247 | B2 * | 4/2015 | Setchell ............ A23L 1/30 514/456 |
| 9,089,547 | B2 * | 7/2015 | Lephard ............ A61K 31/35 |
| 2002/0001565 | A1 | 1/2002 | Shapiro |
| 2002/0019377 | A1 | 2/2002 | Jenkins et al. |
| 2002/0035074 | A1 | 3/2002 | Kelly |
| 2002/0160064 | A1 | 10/2002 | Zulli et al. |
| 2002/0198248 | A1 | 12/2002 | Kelly et al. |
| 2003/0018060 | A1 | 1/2003 | Kelly et al. |
| 2003/0027772 | A1 | 2/2003 | Breton |
| 2003/0059384 | A1 | 3/2003 | Kelly et al. |
| 2003/0078214 | A1 | 4/2003 | Kelly |
| 2003/0219499 | A1 | 11/2003 | Kelly |
| 2004/0147594 | A1 | 7/2004 | Setchell et al. |
| 2004/0235758 | A1 * | 11/2004 | Setchell ............ A23L 1/30 514/27 |
| 2005/0036962 | A1 | 2/2005 | Kelly |
| 2005/0245492 | A1 | 11/2005 | Lephart et al. |
| 2006/0122262 | A1 | 6/2006 | Lephart et al. |
| 2007/0027329 | A1 | 2/2007 | Setchell et al. |
| 2007/0043108 | A1 | 2/2007 | Lephart et al. |
| 2009/0018185 | A1 | 1/2009 | Setchell et al. |
| 2010/0076071 | A1 | 3/2010 | Lephart et al. |

FOREIGN PATENT DOCUMENTS

| | | | | |
|---|---|---|---|---|
| EP | 1 961 309 | A1 | 8/2008 | |
| JP | H02-124883 | | 5/1990 | |
| WO | 93/23069 | | 11/1993 | |
| WO | 94/23716 | | 10/1994 | |
| WO | 96/10341 | | 4/1996 | |
| WO | 97/06273 | | 2/1997 | |
| WO | 98/08503 | | 3/1998 | |
| WO | WO 98/08503 | * | 3/1998 | ............ A61K 31/35 |
| WO | 98/21946 | A1 | 5/1998 | |
| WO | 98/25588 | | 6/1998 | |
| WO | 98/26784 | A1 | 6/1998 | |
| WO | 98/48790 | | 11/1998 | |
| WO | 9852546 | A1 | 11/1998 | |
| WO | 98/56373 | | 12/1998 | |
| WO | 99/07392 | | 2/1999 | |
| WO | 99/36050 | | 7/1999 | |
| WO | 99/36067 | | 7/1999 | |
| WO | 99/49851 | A1 | 10/1999 | |
| WO | 99/61028 | A1 | 12/1999 | |
| WO | 00/13661 | A1 | 3/2000 | |
| WO | 00/30663 | A1 | 6/2000 | |
| WO | 00/41491 | A2 | 7/2000 | |
| WO | 00/49009 | A1 | 8/2000 | |
| WO | 00/62765 | A2 | 10/2000 | |
| WO | 00/62774 | A1 | 10/2000 | |
| WO | 02/03976 | A2 | 1/2002 | |
| WO | 02/03977 | A2 | 1/2002 | |
| WO | 02/03992 | A2 | 1/2002 | |
| WO | 02/11675 | A2 | 2/2002 | |
| WO | 02/053108 | A2 | 7/2002 | |
| WO | 02/062367 | A1 | 8/2002 | |
| WO | 02/067988 | | 9/2002 | |
| WO | 02/087517 | | 11/2002 | |
| WO | 02/089757 | | 11/2002 | |
| WO | 2004/009035 | A2 | 1/2004 | |
| WO | 2004/009035 | A2 | 1/2004 | |
| WO | 2004/022023 | | 3/2004 | |
| WO | 2004/026274 | | 4/2004 | |
| WO | 2004/039327 | A2 | 5/2004 | |

OTHER PUBLICATIONS

Allison, D.B., et al, "A Novel Soy-Based Meal Replacement Formula for Weight Loss Among Obese Individuals: A Randomized Controlled Clinical Trial," *Eur J. Clin Nutr*, 57:514-522 (2003).

Chang, Y.C., and Nair, M.G., "Metabolism of Daidzein and Genistein by Intestinal Bacteria," *J. of Natural Products*, 58(12):1892-1896 (1995).

Chopin, P., and Briley, M., "The Benzodiazepine Antagonist Flumazenil Blocks the Effects of CCK Receptor Agonists and Antagonists in the Elevated Plus-Maze," *Psychopharm*, 110:409-414 (1993).

*Current Protocols in Neuroscience*, 8.3.1-8.3.15, John Wiley & Sons, NY, NY (1997).

Pellow, S., et al., "Validation of open : closed arm entries in an elevated plus-maze as a measure of anxiety in the rat," *J Neurosci Methods*, 14(3):149-167 (1985).

Imhof J.T., et al., "Influence of Gender and Age on Performance of Rats in the Elevated Plus Maze Apparatus," *Behav Brain Res.*, 56(2):177-80 (Sep. 1993).

Jayagopal, V., et al., "Beneficial Effects of Soy Phytoestrogen Intake in Postmenopausal Women With Type 2 Diabetes," *Diabetes Care*, 25:1709-1714 (2002).

Knight, D.C., et al, "A Review of the Clinical Effects of Phytoestrogens," *Obstet Gynec*, 87:897-904 (1996).

Kurosawa, K., et al., "The Absolute Configurations of the Annual Metabolite, Equol, Three Naturally Occurring Isoflavans, and One Natural Isoflavanquinone," *Chemical Communications*, 1265-1264 (1968).

Kurzer, M.S., et al, "Dietary Phytoestrogens," *Annu Rev Nutr.*, 17:353-381 (1997).

Lephart, E.D., et al, "Neurobehavioral effects of dietary soy phytoestrogens," *Neurotoxicology Teratology*, 24(1):5-16 (2002).

Lund, T.D., et al, "Dietary Soy Phytoestrogens Produce Anxiolytic Effects in the Elevated Plus-Maze," *Brain Res*, 913:180-184 (2001).

Magee, P., et al., "Equol: A Comparison of the Effects of the Racemic Compound with That of the Purified S-Enantiomer on the Growth, Invasion, and DNA Integrity of Breast and Prostate Cells in Vitro," *Nutrition and Cancer*, 54(2):232-242 (2006).

Marrian, G.F. and Haslewood, G.D., "CXLV. Equol, a New Inactive Phenol Isolated from the Ketohydroxy-Oestrin Fraction of Mares' Urine," University College, London, Department of Physiology and Biochemistry, 1227-1232 (1932).

Sandoval, D.A., and Davis S.N., "Leptin: Metabolic Control and Regulation, " *J Diabetes Complications*, 17:108-113 (2003).

Setchell, K.D.R., "Phytoestrogens: biochemistry, physiology and implications for human health of soy isoflavones," *Am J Clin Nutr*, 129:1333S-1346S (1998).

Setchell, K.D.R., et al., "Exposure of Infants to Phytoestrogens from Soy Infant Formulas," *The Lancet*, 350:23-27 (1997).

Setchell, K.D.R., et al., "The Clinical Importance of the Metabolite Equol—A Clue to the Effectiveness of Soy and Its Isoflavones," *J. Nutr.*, 132:3577-3584 (2002).

Setchell, K.D.R., et al., "S-Equol, A Potent Ligand for Estrogen Receptor β, is the Exclusive Enantiomeric form of the Soy Isoflavone Metabolite Produced by Human Intestinal Bacterial Flora," *Am. J. Clin. Nutr.*, 81:1072-1079 (2005).

(56) References Cited

OTHER PUBLICATIONS

Setchell, K.D.R. and Cole, S.J., "Method of Defining Equol-Producer Status and Its Frequency Among Vegetarians," *J. of Nutrition*, 136(8):2188-2192 (2006).
Setchell, K.D.R., et al., "Equol—Origins, Actions, and Clinical Relevance of this Specific Soy Isoflavone Metabolite," Fifth International Symposium on the Role of Soy in Preventing and Treating Chronic Disease, Oral Presentation Abstracts, *J. of Nutrition*, 134:1234S-1247S (2004).
Verbit, L. and Clark-Lewis, J.W., "Optically Active Aromatic Chromophores—VIII Studies in the Isoflavonoid and Rotenoid Serices," *Tetrahedron*, 24:5519-5527 (1968).
Wang, X.L., et al., "Enantioselective Synthesis of S-Equol from Dihydrodaidzein by a Newly Isolated Anaerobic Human Intestinal Bacterium," *Applied and Environmental Microbiology*, 71(1):214-219 (2005).
Watanabe, S., et al., "Antioxidant Activity of Soya Hypocotyl Tea in Humans," *Biofactors*, 12(1-4):233-41 (2000).
Lund, T.D., et al., "Equol is a Novel Anti-Androgen that Inhibits Prostate Growth and Hormone Feedback," *Biol. Reprod*, 70(4):1188-95 (2004), E-Pub. (2003).
Lund, T. D., "The Phytoestrogen Metabolite Equol Acts as a Novel Anti-Androgen to Inhibit Prostate Growth and Hormone Feedback," *Abstract Published for Endo 2003 Program; Endocrine Society 85th Annual Meeting*.
Lund, T.D., "Altered Sexually Dimorphic Nucleus of the Preoptic Area (SDN-POA) Volume in Adult Long-Evans Rats by Dietary Soy Phytoestrogens," *Brain Research*, 914(1-2):92-9 (Sep. 2001).
Setchell, K.D.R., et al., "Bioavailability of Pure Isoflavones in Healthy Humans and Analysis of Commercial Soy Isoflavone Supplements," *American Society for Nutritional Sciences*, 1362S-1375S (2001).
Setchell, K.D.R. et al., "Evidence for Lack of Absorption of Soy Isoflavone Glycosides in Humans, Supporting the Crucial Role of Intestinal Metabolism for Bioavailability," *Am J Clin Nutr*, 447-453 (2002).
Setchell, K.D.R., et al., "Nonsteroidal Estrogens of Dietary Origin: Possible Role in Hormone-Dependent Disease," *Am J Clin Nutr*, 40:569-578 (1984).
Setchell, K.D.R., et al., "Dietary Phytoestrogens and Their Effect on Bone: Evidence from in Vitro and in Vivo," Human Observational and Dietary Intervention Studies, *Am J Clin Nutr*, 78(Suppl):593S-609S (2003).
Setchell, K.D.R., et al., "Bioavailability, Disposition, and Dose-Response Effects of Soy Isoflavones When Consumed by Healthy Women at Physiologically Typical Dietary Intakes," *American Society for Nutritional Sciences*, 1027-1035 (2003).
Setchell, K.D.R., et al., "The Clinical Importance of the Metabolite Equol—A Clue to the Effectiveness of Soy and Its Isoflavones," *American Society for Nutritional Sciences*, 3577-3584 (2002).
Setchell, K.D.R., et al., "Phytoestrogens: The Biochemistry, Physiology, and Implications for Human Health of Soy Isoflavones," *Am J Clin Nutr*, 1333S-1346S (1998).
Setchell, K.D.R., et al., "S-Equol, a Potent Ligand for Estrogen Receptor β, is the Exclusive Enantiomeric Form of the Soy Isoflavone Metabolite Produced by Human Intestinal Bacterial Flora," *Am J Clin Nutr*, 81(5):1072-1079 (2005).
Setchell, K.D.R., "Equol—Its Unique Property as a Selective Estrogen Receptor Modulator (SERM) and a Selective Androgen Modulator (SAM)," *Soy & Health*, Brugge, Belgium, Oct. 7-8, 2004.
Brown, Nadine M., et al., "Animal Modes Impacted by Phytoestrogens in Commercial Chow: Implications for Pathways Influenced by Hormones," *Laboratory Investigation*, 81(5):735-747 (2001).
Lephart, E.D., "Brain 5alpha-Reductase: Cellular, Enzymatic, and Molecular Perspectives and Implications for Biological Function," *Molecular and Cellular Neurosciences*, 4:473-484 (1993).
Lephart, E.D., et al., "Brain Androgen and Progesterone Metabolizing Enzymes: Biosynthesis, Distribution and Function," *Brain Res. Brain Res. Rev.*, 37(1-3):25-37 (2001).
Lephart, E.D., "Neurobehavioral Effects of Dietary Soy Phytoestrogens," *Neurotoxicol Teratol*, 24(1):5-16 (2002).
Lephart, E.D., "Estrogens and Phytoestrogens: Brain Plasticity of Sexually Dimorphic Brain Volumes," *J Steroid Biochem Mol Biol.*, 85(2-5):299-309 (2003).
Lephart, E.D., "Dietary Soy Phytoestrogen Effects on Brain Structure and Aromatase in Long-Evans Rats," *NeuroReport*, 12(16):3451-3455 (2001).
Lephart, E.D., "Behavioral Effects of Endocrine-Disrupting Substances: Phytoestrogens," *ILAR J.*, 45(4):443-54 (2004).
Lephart, E.D., "Dietary Isofavones After Regulatory Behaviors, Metabolic Hormones and Neuroendocrine Function in Long-Evans Male Rates," *Nutrition & Metabolism*, 1(16):1-14 (2004).
Lephart, E.D., "Equol Reduces Prostate Size and Tail Skin Temperature in Male Rats," *Experimental Biology*, Abstract #280.9, San Diego, CA, Apr. 2-6, 2005.
Lephart, E.D., "Antiaging Effects of Equol: A Unique Antiandrogenic Isoflavone Metabolite and its Influence in Stimulating Collagen Deposition in Human Dermal Monolayer Fibroblasts," *American Academy of Dermatology*, 52(3):1005, 63rd Annual Meeting, New Orleans, LA (Feb. 18-22, 2005).
Lephart, E.D., "Equol: A Unique Anti-Androgenic Isoflavone Metabolite Stimulates Collagen (I & III), Elastin and Human Fibroblast Proliferation and Inhibits MMP's and Elastase in 3-D Cultures via FACS Analysis," (2005).
Weber, K.S., "Dietary Soy-Phytoestrogens Decrease Testosterone Levels and Prostate Weight Without Altering LH, Prostate 5α-reductase or Testicular Steroidogenic Acute Regulatory Peptide Levels in Adult Male Sprague-Dawley Rats," *J of Endocrinology*, 170:591-599 (2001).
Adlercreutz, H., et al., "Dietary Phytoestrogens and Cancer: In Vitro and In Vivo Studies," *J. Steroid Biochem Mol Biol*, 41(3-8):331-37 (1992).
Adlercreutz, H., et al., "Dietary Phytoestrogens and the Menopause in Japan," *Lancet*, 339(8803):1233 (1992).
Adlercreutz, H., et al., "Effect of Dietary Components, Including Lignans and Phytoestrogens, on Enterophepatic Circulation and Liver Metabolism of Estrogens and on Sex Hormone Binding Globulin (SHBG)," *J Steroid Biochem*, 27(4-6):1135-44 (1987).
Adlercreutz, H., et al., "Diet and Breast Cancer," *Acta Oncol*, 31(2):175-81 (1992).
Adlercreutz, H., et al., "Determination of Urinary Lignans and Phytoestrogen Metabolites, Potential Antiestrogen and Anticarcinogens in Urine of Women on Various Habitual Diets," *J. Steroid Biochem*, 25:791-797 (1996).
Akaza, H., et al., "Is Daidzein Non-Metabolizer a High Risk for Prostate Cancer? A Case-Controlled Study of Serum Soybean Isoflavone Concentration," *Jpn J Clin Oncol*, 32(8):296-300 (2002).
Albert, A., et al., "Efficacy and Safety of a Phytoestrogen Preparation Derived from Glycine max (L.) Merr in Climacteric Symptomatology: A Multicentric, Open, Prospective and Non-Randomized Trial," *Phytomedicine*, 9(2):85-92 (2002).
Alvira, E. et al., "Molecular Modeling Study for Chiral Separation of Equol Enantiomers by ~-Cyclodextrin," *Chemical Physics*, 240:101-108 (1999).
Anderson, Edith L. et al., "The Identification of Equol as 7-Hydroxy-3-(4'-Hydroxyphenyl) Chroman, and the Synthesis of Racemic Equol Methyl Ether," *J. Biol. Chem*, 127: 649-56 (1939).
Atkinson, C. et al., "In Vitro Incubation of Human Feces with Daidzein and Antibiotics Suggests Interindividual Differences in the Bacteria Responsible for Equol Production," *Amer. Society for Nutritional Sciences*, 134:596-599 (Mar. 2004).
Axelson, M. et al., "The Identification of the Weak Oestrogen Equol [7-hydroxy-3-(4'-hydroxyphenyl)chroman] in Human Urine," *Biochem. J.*, 201:353-357 (1982).
Axelson, M., et al., "Soya—A Dietary Source of the Non-Steroidal Oestrogen Equol in Man and Animals," *J Endocrinol*, 102(1):49-56 (1984).
Bowey, E. et al., Metabolism of Isoflavones and Lignans by the Gut Microflora: a Study in Germ-Free and Human Flora Associated Rats, *Food Chem Toxicol.*, 41(5):631-6 (May 2003).

(56) References Cited

OTHER PUBLICATIONS

Cassidy, A., "Physiological Effects of Phyto-Oestrogens in Relation to Cancer and Other Human Health Risks." *Proc Nutr Soc*, 55(1B):399-417 (1996).
Cassidy, A., S. Bingham, and K. Setchell, "Biological Effects of Isoflavones in Young Women: Importance of the Chemical Composition of Soya Bean Products," *Br J Nutr*, 74(4):587-601 (1995).
Duncan, A. M. et al., "Premenopausal Equol Excretors Show Plasma Hormone Profiles Associated with Lowered Risk of Breast Cancer," *Cancer Epidemiol, Biomarkers Prev*, 9: 581-586 (Jun. 2000).
Gambacciani, M., et al., "Effects of Low-Dose, Continuous Combined Estradiol and Noretisterone Acetate on Menopausal Quality of Life in Early Postmenopausal Women," *Maturitas*, 44(2):157-63 (2003).
Garreau, B., et al., "Phytoestrogens: New Ligands for Rat and Human Alpha-Fetoprotein," *Biochim Biophys Acta*, 1094(3):339-45 (1991).
Giri, A.K. and LJ. Lu, "Genetic Damage and the Inhibition of 7, 12-dimethylbenz[a]anthracene-induced Genetic Damage by the Phytoestrogens, Genistein and Daidzein, in Female ICR Mice," *Cancer Lett*, 95(1-2):125-33 (1995).
Goldin, B.R. and S.L. Gorbach, "Phytoestrogens: Possible Role in Preventing Human Disease," *Nutrition*, 12(3):216-217 (1996).
Hartley, D.E., et al., "The Soya Isoflavone Content of Rat Diet can Increase Anxiety and Stress Hormone Release in the Male Rat," *Psychopharmacology (Berl)*, 167(1):46-53 (2003).
Havsteen, B., "Flavonoids, A Class of Natural Products of High Pharmacological Potency," *Biochem Pharmacol*, 32(7):1141-8 (1983).
Hedlund, T.E., W.U. Johannes, and GJ. Miller, "Soy Isoflavonoid Equol Modulates the Growth of Benign and Malignant Prostatic Epithelial Cells In Vitro," *Prostate*, 54(1):68-78 2003.
Hwang, J. et al., "The Phytoestrogen Equol Increases Nitric Oxide Availability by Inhibiting Superoxide Production: An Antioxidant Mechanism for Cell-Mediated LDL Modification," *Free Radical Biology & Medicine*, 34(10):1271-1282 (2003).
Kao, P.C. and K. P'eng F, "How to Reduce the Risk Factors of Osteoporosis in Asia," *Zhonghua Yi Xue Za Zhi (Taipei)*, 55(3):209-13 (1995).
Kaziro R. et al., "The Oestrogenicity of Equol in Sheep," *J Endocrinol*, 103(3):395-9 (Dec. 1984).
Kinjo, J., "Phytoestrogens," *Japanese Journal of Clinical Medicine*, 58(12):2434-8 (Dec. 2000).
Kohli, J.C. et al., "Specific Separation of Equol from Estrogens by Thin-Layer Chromatography," *Journal of Chromatography*, 129: 473-474 (1976).
Kostelac, D., G. Rechkemmer, and K. Briviba, "Phytoestrogens Modulate Binding Response of Estrogen Receptors Alpha and Beta to the Estrogen Response Element," *J Agric Food Chem.*, 51 (26):7632-5 (2003).
Lamartiniere, C.A., et al., "Daidzein: Bioavailability, Potential for Reproductive Toxicity, and Breast Cancer Chemoprevention in Female Rats," *Toxicol Sci*, 65(2):228-38 (2002).
Lamberton, John A. et al., "Catalytic Hydrogenation of Isoflavones. The Preparation of(±)-Equol and Related Isoflavans," *Aust. J. Chem.*, pp. 455-457 (1978).
Landstrom, M., et al., "Inhibitory Effects of Soy and Rye Diets on the Development of Dunning R3327 Prostate Adenocarcinoma in Rats," *Prostate*, 36(3):151-61 (1998).
Lu, L.J., et al., "Effects of Soya Consumption for One Month on Steroid Hormones in Premenopausal women: Implications for Breast Cancer Risk Reduction," *Cancer Epidemiol Biomarkers Prev*, 5(1):63-70 (1996).
Lyn-Cook, B.D., et al., "Methylation Profile and Amplification of Proto-Oncogenes in Rat Pancreas Induced with Phytoestrogens," *Proc Soc Exp Biol Med*, 208(1):116-119 (1995).
Martin, M.E., et al., "Interactions Between Phytoestrogens and Human Sex Steroid Binding Protein," *Life Sci*, 58(5):429-436 (1996).

Mitchell, J.H., SJ. Duthie, and AR. Collins, "Effects of Phytoestrogens on Growth and DNA Integrity in Human Prostate Tumor Cell Lines: PC-3 and LNCaP," *Nutr Cancer*, 38(2):223-228 (2000).
Morito, K., et al., "Interaction of Phytoestrogens with Estrogen Receptors Alpha and Beta," *Biol Pharm Bull*, 24(4):351-356 (2001).
Murkies, A.L., et al., "Dietary Flour Supplementation Decreases Post-Menopausal Hot Flushes: Effect of Soy and Wheat," *Maturitas*, 21(3):189-195 (1995).
Muthyala, R.S., et al., "Equol, A Natural Estrogenic Metabolite from Soy Isoflavones: Convenient Preparation and Resolution of R- and S-Equols and Their Differing Binding and Biological Activity through Estrogen Receptors Alpha and Beta," *Bioorg Med Chern*, 12(6):1559-1567 (2004).
Naim, M., et al., "Antioxidative and Antihemolytic Activities of Soybean Isoflavones," *J Agric Food Chem*, 24(6):1174-1177 (1976).
Ogawara, H., "A Specific Inhibitor for Tyrosine Protein Kinase from Pseudomonas," *The Journal of Antibiotics*, 39(4):606-608 (Apr. 1936).
Ohta, Atsutane et al., "A Combination of Dietary Fructooligosaccharides and Isoflavone Conjugates Increases Femoral Bone Mineral Density and Equol Production in Ovariectomized Mice," *American Society for Nutritional Sciences*, 132:2048-2054 (2002).
Rafii, F. et al., "Variations in Metabolism of the Soy Isoflavonoid Daidzein by Human Intestinal Microfloras from Different Individuals," *Arch Microbiol.*, 180(1):11-6 (Jul. 2003) (Epub May 29, 2003).
Rimbach, G., et al., "Antioxidant and Free Radical Scavenging Activity of Isoflavone Metabolites," *Xenobiotica*, 33(9):913-925 (2003).
Rowland, I.R., et al., "Interindividual Variation in Metabolism of Soy Isoflavones and Lignans: Influence of Habitual Diet on Equol Production by the Gut Microflora," *Nutr Cancer*, 36(1):27-32 (2000).
Sathyamoorthy, N. et al., "Differential Effects of Dietary Phyto-Oestrogens Daidzein and Equol on Human Breast Cancer MCF-7 Cells," *European Journal of Cancer*, 33(14):2384-2389 (Dec. 1997).
Sharma, O.P., et al., "Soy of Dietary Source Plays a Preventive Role Against the Pathogenesis of Prostatitis in Rats," *J Steroid Biochem Mol Biol*, 43(6):557-564 (1992).
Sharpe, R.M. and N.E. Skakkebaek, "Are Oestrogens Involved in Falling Sperm Counts and Disorders of the Male Reproductive Tract?" *Lancet*, 341(8857):1392-5 (1993).
Sigma-Aldrich webpage, (±)-Equol, Product No. 45405, Oct. 23, 2003.
Sigma-Aldrich webpage, Equol, Product No. 45405, Jul. 10, 2003.
Spinozzi, F., et al., "The Natural Tyrosine Kinase Inhibitor Genistein Produces Cell Cycle Arrest and Apoptosis in Jurkat T-leukemia Cells," *Leuk Res*, 18(6):431-9 (1994).
Thompson, M.A. et al., "Characterization of the Estrogenic Properties of a Nonsteroidal Estrogen, Equol, Extracted from Urine of Pregnant Macaques," *Biol Reprod*, 31:705-713 (Nov. 1984).
Wahala, Kristina et al., "Synthesis of the [2H]-Labeled Urinary Lignans, Enterolactone and Enterodiol, and the Phytoestrogen Daidzein and its Metabolites Equol and O-Demethyl-angolensin," *J. Chem. Soc. Perkin Trans. 1*, pp. 95-98 (1986).
Whitehead, M., "Treatments for Menopausal and Post-Menopausal Problems: Present and Future," *Baillieres Clin Obstet Gynaecol*, 10(3):515-30 (1996).
Widyarini, S., et al., "Isoflavonoid Compounds from Red Clover (*Trifolium pratense*) Protect from Inflammation and Immune Suppression Induced by UV Radiation," *Photochem Photobiol.*, 74(3):465-470 (Sep. 2001).
Luk, K.C., et al., "Isolation and Identification of "Diazepam-Like" Compounds from Bovine Urine," *Journal of Natural Products*, 46(6):852-861 (Nov.-Dec. 1983).
Supplementary European Search Report, Application No. EP03777944, mailed Jun. 6, 2007, 6 pgs.
"Isoflavonoid Compounds from Red Clover (*Trifolium pratense*) Protect from Inflammation and Immune Suppression Induced by UV Radiation," *Photochemistry and Photobiology*, 74(3):465-470 (2001).
"Phytoestrogens," *Japanese J. of Clinical Medicine*, 58(12):2434-2438 (2000).

(56) References Cited

OTHER PUBLICATIONS

Evans, et al., "Inhibition of 5a-reductase in genital skin fibroblasts and prostate tissue by dietary lignans and isoflavonoids," *J. Endocrinol*, 147(2):295-302 (1995).

Mitchell, et al., "Effects of Phytoestrogens on Growth and DNA Integrity in Human Prostate Tumor Cell Lines: PC-3 and LNCaP," *Nutr. Cancer*, 38(2):223-228 (2000).

European Search Report in European Application No. EP10194495, dated Feb. 22, 2011.

Examiner's Report in Canadian Application No. 2,564,399, dated Mar. 2, 2011.

Third Party Observations filed in European Patent Application No. 10194495.7, dated Aug. 10, 2011; provided with the letter from the European associate dated Aug. 22, 2011 (copy enclosed).

Gimenez et al., J. Hypertens., 15:1303-8 (1997).

Lou et al., J. Med. Food, 2(3-4):257-60 (1999).

Chin-Dusting et al., Br. J. Pharmacol., 133:595-605 (2001).

DeVito et al., Peptides, 31:1412-1419 (2010).

Supplementary European Search Report in EP Application No. 06813546.6-1216/2063898 dated Jan. 17, 2012.

International Search Report and Written Opinion in PCT Application No. PCT/US2010/043017 dated Feb. 3, 2012.

Wähälä, et al., "Monoalkylation of Daidzein (7,4'-Dihydroxyisoflavone) Synthesis of 7-O-(Carboxybutyl)equol," *Finnish Chemical Letters*, 16(1-6):79-83 (1989).

Jokela, "Synthesis of Reduced Metabolites of Isoflavonoids, and their Enantiomeric Forms," *Laboratory of Organic Chemistry, Department of Chemistry, Faculty of Science, University of Helsinki, Finland* (Nov. 26, 2011).

Roy, "An Introduction to Pharmaceutical Sciences, Production, Chemistry, Techniques and Technology," *Biohealthcare Publishing Textbook, Series on Pharma, Biotech and Biosciences* (2011).

*Edward Douglas Lephart, et al., v. Kenneth David Reginald Setchell, et al.*, Patent Interference No. 105,950, Decision—Motions—Bd. R. 125(a), Dec. 19, 2014.

*Edward Douglas Lephart, et al., v. Kenneth David Reginald Setchell, et al.*, Patent Interference No. 105,950, Judgement—Bd. R. 127(a), Dec. 19, 2014.

US 6,448,237, 09/2002, Kelly (withdrawn)

\* cited by examiner

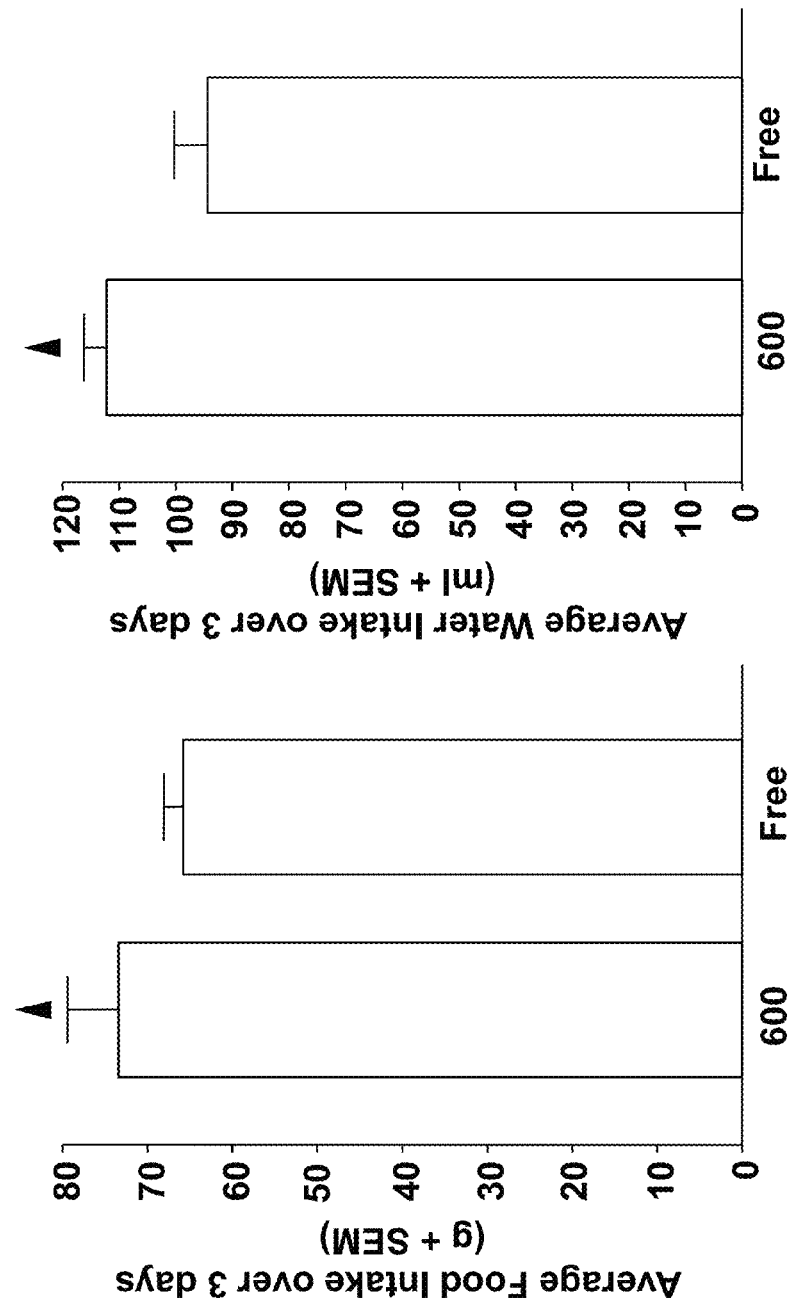

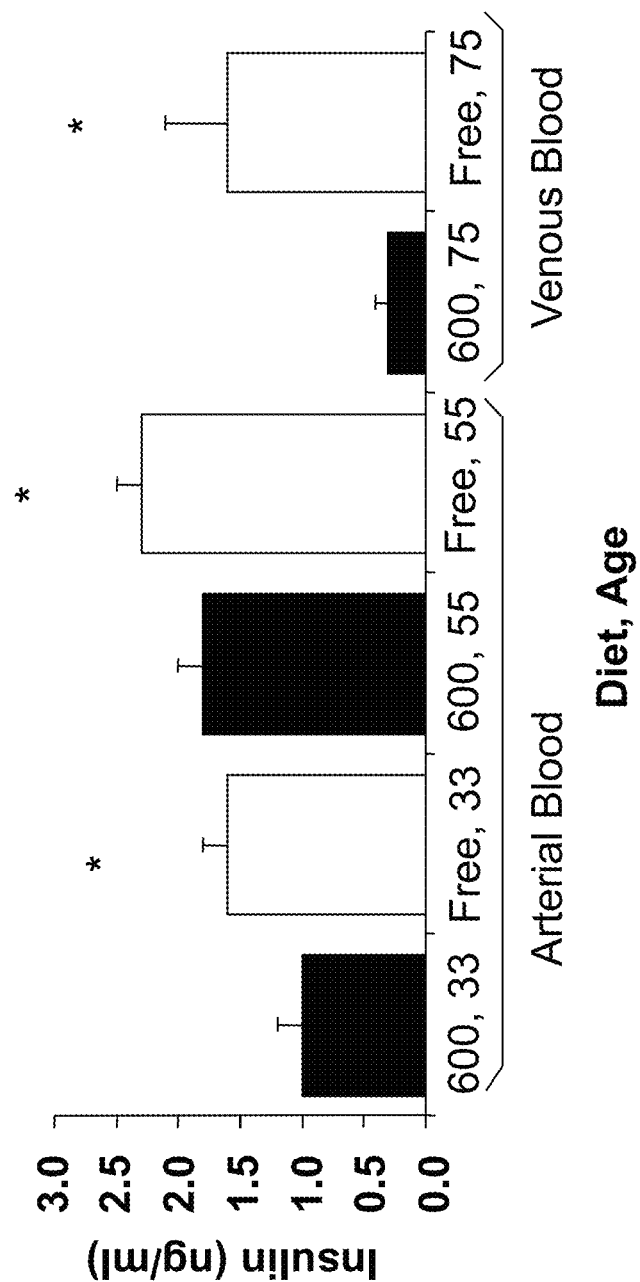

□ = significantly increased number of entries compared to AIN- 76 values
* = significantly increased number of entries compared to all other groups
n = 7 animals per group □ = significantly increased time spent in open arms compared to AIN-76 values
? = significantly increased time spent in open arms compared to AIN-76 and Phyto-free values
n = 7 animals per group

USE OF EQUOL FOR TREATING ANDROGEN MEDIATED DISEASES

CROSS-REFERENCE TO RELATED APPLICATIONS

The present application is a continuation application of U.S. Ser. No. 13/903,748, filed May 28, 2013, now issued U.S. Pat. No. 9,089,547, which is a continuation of U.S. Ser. No. 13/442,466, filed Apr. 9, 2012, now issued U.S. Pat. No. 8,450,364, which is a continuation of U.S. Ser. No. 12/572, 791, filed Oct. 2, 2009, now issued U.S. Pat. No. 8,153,684, which is a continuation application of U.S. Ser. No. 10/533, 045, filed Oct. 20, 2005, now abandoned, which is a U.S. national stage filing under 37 U.S.C. §371 of International Application PCT/US03/34441, filed Oct. 29, 2003, which claims priority to U.S. provisional patent application No. 60/422,469, filed Oct. 29, 2002, contents of which are incorporated herein by reference in their entirety.

GOVERNMENT INTERESTS

This invention was made with Government support under Grant No. NS3995 1, awarded by the National Institute of Health (NIT, and Grant No. NRI 2002-00798, awarded by the U.S. Dept. of Agriculture (USDA). The Government has certain rights in this invention.

BACKGROUND OF THE INVENTION

This invention relates to equol and its mechanism of action and use as a therapeutic compound for treating and preventing physiological and pathophysiological conditions mediated by androgens.

In recent years phytoestrogens have received increased investigative attention due to their potential protective effects against age-related diseases (e.g. cardiovascular disease and osteoporosis) and hormone-dependent cancers (i.e., breast and prostate cancer). There are three main classifications of phytoestrogens: 1) isoflavones (derived principally from soybeans), 2) lignans (found in flaxseed in large quantities) and 3) coumestans (derived from sprouting plants like alfalfa). Of these three main classifications, human consumption of isoflavones has the largest impact due to its availability and variety in food products containing soy. Of the isoflavones, genistein and daidzein are thought to exert the most potent estrogenic hormone activity and thus most attention has been directed toward these molecules (Knight D. C. et al., Obstet Gyneco, 187:897-904, (1996), Setchell, K. D. R., Am J Clin Nutr, 129:1333S-1346S (1998); Kurzer, M. S. et al., Anne Rev Nutr, 17:353-381(1997)). However, these isoflavone molecules do not exist at high levels in their biologically active form in soy foods, but rather are at high abundance in a precursor form. For example, genistin, the precursor of genistein, is the glycosidic form that contains a carbohydrate portion of the molecule. Additionally, malonylglucoside and acetylglucoside forms also are found. These conjugates are metabolized in the GI tract by intestinal bacteria, which hydrolyze the carbohydrate moiety to the biologically active phytoestrogen, genistein. The same metabolic step occurs for the aglycone daidzein, which is converted from the glycosidic form daidzin. Diadzein is then further metabolized to equol in an "equol-producing" mammal. Thereafter, equol circulates in the blood stream at very high concentrations. Equol is not normally present in the urine of most healthy adults unless soy is consumed. The formation of equol in vivo is exclusively dependent on intestinal microflora as evidenced from the finding that germ-Phyto-Free animals do not excrete equol, and that equol is not found in the plasma and urine of newborn or 4-month old infants fed exclusively soy foods from birth due to the fat that the intestinal flora has not yet developed in neonates. See Setchell K. D. R. et al The Lancet 1997; 350:23-27).

The phenolic ring structures of isoflavones enable these compounds to bind estrogen receptors (ER) and mimic estrogen. Although genistein and daidzein bind to ER, it is with a lower affinity when compared to estradiol, and with a greater affinity for ERβ than to ERα. Additionally, phytoestrogens have been reported to act like natural selective estrogen receptor modulators (SERMs) at various tissue sites throughout the body. In some tissues, there is evidence that phytoestrogens act as estrogen agonists, whereas in others, they display antagonistic characteristics comparable to that of tamoxifen or raloxifene where SERM activity appears to be sex-hormone and gender dependent.

While the bulk of the scientific literature has focused on the natural isoflavones in soy or clover, little has been reported on the actions or effects of their intestinally derived metabolites.

Equol (7-hydroxy-3(4'hydroxyphenyl)-chroman) represents the major metabolite of the phytoestrogen daidzein, one of the main isoflavones found abundantly in soybeans and soy-foods. Equol, however, is not a phytoestrogen, because it is not a natural constituent of plants. Equol does not occur naturally in any plant-based products. Rather, it is a non-steroidal isoflavone that is exclusively a product of intestinal bacterial metabolism (relatively few individuals, ~30-40%, have the micro flora necessary to convert soy isoflavones to equol). Previous research with equol has identified that equol possess some weak estrogenic properties, binds sex hormone binding globulin, binds α-fetoprotein, and has antioxidant activity. However, equol is unique among the plant-derived isoflavones in that it possesses a chiral center and as such exists as two distinct enantiomeric forms, the R- and S-enantiomers. We have shown that the S-enantiomer of equol is the exclusive equol form found in the urine and plasma of "equol-producing" mammals consuming soy, and is the only equol enantiomer made by human intestinal bacteria. All previous studies on equol appear to have been conducted with the racemic form of equol. There has in general been a lack of appreciation that two forms of equol exist and to our knowledge no previous study has reported on the specific actions or activity of the individual enantiomers. The R- and S-enantiomers conformationally differ, which subsequently influences their biological activity. For example, only the S-enantiomer of equol binds estrogen receptor (ER) with sufficient affinity to make it relevant to bind circulating equol levels reported in humans. Compared to 17β-estradiol the relative binding affinities of the R- and S-equol enantiomer for ERα are 210.6 and 49.2 fold less respectively. However, the S-equol enantiomer seems to be largely ER☐-selective with a relatively high affinity for ERβ. Enantiomer S-equol binds ERβ at approximately 20% that of 17β-estradiol [equol, Kd=0.7 nM vs. 17β-estradiol, Kd=0.15 nM], while the R-equol enantiomer binds at approximately 100 fold less. R-Equol, although not naturally occurring, is of considerable importance because of its ability to modulate androgen-mediated processes in the body.

The prostate gland depends on androgen hormone action for its development and growth, and the development of human benign prostatic hyperplasia (BPH) clearly requires a combination of testicular androgens during the aging process. However, testosterone is not the major androgen responsible for growth of the prostate. The principal prostatic androgen is dihydrotestosterone (DHT), as evidenced by current treatments of prostatic cancer are directed toward reducing DHT with 5α-reductase inhibitors. Although not elevated in human BPH, DHT levels in the prostate remain at a normal level with aging, despite a decrease in the plasma testosterone. Testosterone is converted to DHT by 5α-reductase in prostatic stromal and basal cells. DHT is primarily responsible for prostate development and the pathogenesis of BPH. Inhibitors of 5α-reductase reduce prostate size by 20% to 30%. This reduction in glandular tissue is achieved by the induction of apoptosis, which is histologically manifested by ductal atrophy. 5α-reductase occurs as 2 isoforms, type 1 and type 2, with the prostate expressing predominantly the type-2 isoform, and the liver and skin expressing primarily the type-I isoform. Patients have been identified with deficiencies in the type-2 5α-reductase, but not type 1. Knockout mice with the type-2 5α-reductase null-mutation demonstrate a phenotype similar to that seen in men with 5α-reductase deficiency. Type-1 5α-reductase knockout male mice are phenotypically normal with respect to reproductive function. Enzymatic activity for 5α-reductase or immunohistochemical detection has been noted in other genitourinary tissues, such as the epididymis, testes, gubernaculum, and corporal cavernosal tissue.

Quantitatively, women secrete greater amounts of androgen than of estrogen. The major circulating steroids generally classified as androgens include dehydroepiandrosterone sulphate (DHEAS), dehydroepiandrosterone (DHEA), androstenedione (A), testosterone (T), and DHT in descending order of serum concentration, though only the latter two bind the androgen receptor to a significant degree. The other three steroids are better considered as pro-androgens. –DHT is primarily a peripheral product of testosterone metabolism. Testosterone circulates both in its free form, and bound to protein including albumin and sex steroid hormone-binding globulin (SHBG), the levels of which are an important determinant of free testosterone concentration. The postmenopausal ovary is an androgen-secreting organ and the levels of testosterone are not directly influenced by the menopausal transition or the occurrence of menopause.

The work of some research has focused on the development of steroidal compounds for the treatment of androgen dependent diseases such as: hirsutism, androgenic alopecia, benign prostatic hyperplasia (BPH) and prostate cancer. DHT has been implicated as a causative factor in the progression of these diseases, largely through the clinical evaluation of males who are genetically deficient of steroid 5α-reductase enzyme. As a result of such studies, the inhibition of this enzyme has become a pharmacological strategy for the design and synthesis of new antiandrogenic drugs. However, it is unclear whether inhibition of 5α-reductase will have a deleterious impact on the system, as evidenced by contraindications arising from reported side effects of conventional treatments using 5α-reeducates inhibitors. The development of different strategies that target the inhibition of DHT effects would be a major advance in the therapy of androgen-mediated conditions.

Despite the recent gains in understanding the pharmacology of equol as it pertains to estrogen actions, our research showing potent antiandrogen effects of equol is unique and novel and opens new approaches to preventing or treating androgen-related conditions. Binding or sequestering DHT would provide a means for inhibiting its effect on DHT-sensitive tissues. There is no known ligand that is specific for DHT, but such an agent would have distinct advantages over non-discriminatory compounds that target the androgen receptor directly or the enzymes involved in androgen synthesis.

BRIEF SUMMARY OF THE INVENTION

The present invention relates to a method of modulating physiological and pathophysiological conditions mediated by androgens in a mammal, comprising the step of administering to the mammal an effective amount of an enantiomeric equol that can bind with free 5α-dihydrotestosterone, thereby inhibiting the binding of 5α-dihydrotestosterone with the androgen receptors (AR) in the mammal and mediating the conditions mediated by the androgen.

The present invention also relates to a method of treating and preventing an androgen-related disease in a mammal, comprising the step of administering to the mammal an effective amount of an enantiomeric equol that can bind with free 5α-dihydrotestosterone, thereby inhibiting the binding of the 5α-dihydrotestosterone with the androgen receptors in the mammal.

The present invention further relates to a method of modulating androgen hormone activity in a mammal, comprising the step of administering to the mammal an effective amount of an enantiomeric equol that can bind with free 5α-dihydrotestosterone, thereby modulating the binding of 5α-dihydrotestosterone with the androgen receptors in the mammal.

The present invention additionally relates to a method of preventing DHT binding to the AR by contacting the DHT with an enantiomeric equol prior to the binding of DHT and AR.

The present invention relates to a method of treating and preventing a combination of an androgen-related condition and an estrogen-related condition in a mammal, comprising the step of administering to a mammal an effective amount of a mixture of R-equol and S-equol, that can bind with free 5α-dihydrotestosterone, and with free 5α-dihydrotestosterone and the estrogen receptor, respectively, thereby inhibiting the binding of the 5α-dihydrotestosterone with the androgen receptors, and affecting binding of the estrogen receptors.

The present invention also relates to a method of modulating age-related androgen/estrogen hormonal balances, comprising the steps of: 1) determining a mammal's endocrine androgen/estrogen hormone balance, 2) administering to the mammal an effective amount of a mixture of R-equol and S-equol, that can modulate the hormone balance of 5α-dihydrotestosterone and estrogen.

The present invention further relates to a use of an enantiomeric equol to bind in vivo free DHT, for modulating physiological and pathophysiological conditions mediated by androgens in a mammal.

The present invention also relates to a method of regulating the level of LH in vivo in a mammal by contacting the DHT of the mammal with enantiomeric equol.

The present invention relates to a use of enantiomeric equol as a diagnostic agent for physiological and pathophysiological conditions mediated by androgens/androgen-related disorders affected by an estrogenic/androgenic imbalance.

The present invention further relates to a use of equol in a competitive binding assay, the assay comprising the steps of: 1) providing an androgen receptor, 2) providing a complex of DHT-enantiomeric equol, 3) providing a test substance comprising an androgen binding moiety, 4) contacting and competing for the DHT-enantiomeric equol complex.

BRIEF DESCRIPTION OF THE DRAWINGS

FIG. 8A shows two distinct peaks in [3H]-DHT+equol incubated with prostate (A), while.

FIGS. 16A and 16B show food and water intake in male rats fed a Phyto-600 or a Phyto-Free diet, respectively.

FIGS. 17A and 17B show plasma leptin and insulin levels from male rats fed a Phyto-600 or a Phyto-Free diet, respectively.

DETAILED DESCRIPTION OF THE INVENTION

Figure 1:
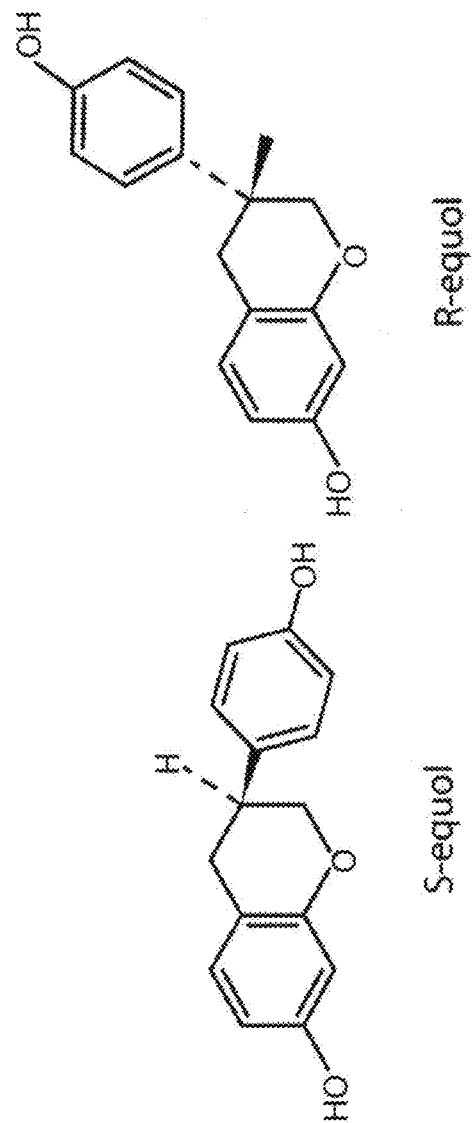
FIG. 1 shows the chemical structures of S-equol and R-equol enantiomers.

A novel mechanism of action for equol has been identified with important ramifications in health and disease and which indicates a broad and important usage for equol in the treatment of androgen mediated pathologies. Equol can act as an anti-androgen. The anti-androgenic properties of equol are unique in that equol does not bind the androgen receptor (AR) but specifically binds 5α-dihydrotestosterone (DHT) with high affinity and thereby prevents DHT from binding the AR. Furthermore, both the R- and S-enantiomers of equol specifically bind DHT, sequester DHT from the AR and block DHT's actions in physiological processes in vivo. Racemic equol, which constitutes R-equol and S-equol and R-equol or S-equol alone, selectively bind DHT.

In mammals, there are two principal androgens, testosterone and its 5α-reduced metabolite, DHT. DHT is recognized as the most potent androgen in the mammalian body. The AR, which is encoded by a single-copy gene located on the human X-chromosome, specifically mediates the actions of androgens. Although both testosterone and DHT bind the AR, certain tissues (i.e. prostate gland, hair follicles, etc.) that are only slightly influenced by testosterone are greatly influenced by DHT. Furthermore, DHT has been implicated in a number of diseases and disorders. Because equol specifically binds and prevents the actions of DHT, there is an indication for a broad and important usage for equol in the treatment of androgen-mediated pathologies.

Equol has a structure similar to the steroidal estrogen estradiol. Equol is unique among the isoflavones in that it possesses a chiral center and as such exists as two distinct enantiomeric forms, the R- and S-enantiomers. All previous studies on equol appear to have been conducted with the racemic form of equol. There has in general been a lack of appreciation that two forms of equol exist and to our knowledge no previous study has reported on the specific actions or activity of the individual enantiomers. R- and S-equol specifically bind 5α-dihydrotestone (DHT). Equol racemic, R-equol or S-equol does not bind the androgen receptor. R-equol does not bind the estrogen receptor system. S-equol only binds ERβ (with an affinity approximately 5-times less than 17β-estradiol). Thus, R- and S-equol have SERM-like properties along with having the capability to selectively bind the most potent circulating androgen, DHT.

Most of the interest in soy and its constituent isoflavone, genistein, and to a lesser extent daidzein, has focused on either their estrogenic actions, or other non-hormonal actions such as their affects on enzymes, growth factors or cytokines, or their antioxidant actions. Never previously has there been any discussion of the potential antiandrogen actions for isoflavones and rarely is the enantiomeric forms of equol even mentioned. The present invention addresses the effects of the enantiomeric forms of equol and specifically, the ability of both S-equol, the natural metabolite of daidzein, and R-equol to antagonize the actions of the potent androgen dihydrotestosterone, DHT. Such effects open up novel possibilities for dietary, nutraceutical, and pharmacological approaches to prevention and treatment of disease where the potent androgen DHT plays a detrimental role. This includes but is not restricted to prostate cancer, skin diseases, hair loss, and obesity. Additionally, the estrogenic actions of S-equol can also be of benefit in treating or preventing prostate cancer because the combined actions of equol acting at the estrogen receptor level and as an antiandrogen.

Equol Binds with DHT

Equol (7-hydroxy-3(4'hydroxyphenyl)-chroman) represents the major metabolite of phytoestrogens daidzin and daidzein, isoflavones found abundantly in soybeans and soyfoods, and is an important biologically active molecule. In animals fed a phytoestrogen-rich diet, the major circulating isoflavone is equol, which accounts for 70-90% of the total circulating isoflavone levels. The present invention discloses a novel model of equol's biological properties. In binding studies, equol enantiomers specifically bind 5α-dihydrotestosterone (DHT), but not testosterone, DHEA or estrogen. By doing so, equol sequesters DHT from the androgen receptor without directly binding the androgen receptor itself. In vivo studies demonstrate that equol treatment of intact male rats significantly decreased prostate and epididymis but not testes weights. In castrated male rats treated with DHT after administering equol, equol blocked DHT's trophic effects on the prostate gland and its negative feedback effects on plasma luteinizing hormone (LH) levels.

It has been found that equol can act as an anti-androgen, by specifically binding DHT and preventing DHT from binding to the androgen receptor (AR) without itself binding the AR. It also has been shown that DHT that has already been bound to the AR will not be competitively bound by enantiomeric equol. Therefore, one embodiment of the present invention is a method of preventing DHT binding to the AR by contacting DHT with equol prior to DHT-AR binding occurs. The enantiomeric equol may be brought into contact with the DHT in vitro or in vivo. When the DHT is to be contacted in vivo, the equol may be administered by any route that allows absorption of equol to the blood stream. Biologically available DHT is free and unbound by any native ligand prior to binding with equol.

Reproductive organs such as the prostate and epididymis are known to be under androgenic control. Previous data has shown that before puberty, when circulating androgen levels are very low, rats fed a diet containing high levels of soy-derived isoflavones have prostate weights that are not altered by the consumption of this diet. However, after puberty when androgen levels increase, prostate weights are significantly decreased in phytoestrogen-rich-diet fed rats compared to animals fed a phytoestrogen-free diet. These data are similar to the present findings that equol-treated intact rats display significant decreases in prostate and epididymis weights (without alterations in testes or pituitary weights during short-term studies). Notably, if the prostate and epididymal values are standardized to body weight (per 100 grams) the ratios are still significantly different between equol-treated and control values. Equol also blocked DHT's androgenic trophic influence on the prostate and epididymis, without significantly altering testosterone levels.

DHT has negative feedback effects on circulating plasma levels of luteinizing hormone (LH). Equol significantly increases LH levels by binding DHT and preventing this feedback effect. Equol completely reverses the inhibitory action of DHT on LH levels in gonadectomized (GDX)

males, whereas DHT plus equol-treated male rats display LH levels similar to that of control values. These data further suggest that equol has the specific ability to bind DHT, presumably in the blood circulation system, and block the hormonal action of DHT in suppressing LH production or secretion. Therefore an embodiment of the present invention is a method of modulating LH levels in an individual by contacting the DHT of the individual with enantiomeric equol. The equol can be administered by any route that allows absorption of equol to the blood stream, with the amount administered in accordance with the nature of the ailment to be treated and size of the individual.

The Structure of Equol

Equol is distinct from most isoflavones in having a chiral center due to the lack of a double bond in the heterocyclic ring. The phytoestrogen isoflavones from soy (daidzein, glycitein and genistein), clover (formononetin and biochanin A), and kudzu, (peurarin), do not have a chiral center. FIG. 1 shows the chemical structures of R-equol and S-equol.

The R- and S-enantiomers conformationally differ and this is predicted to influence how an equol enantiomer fits into the binding site in the cavity of the dimerized ER complex, and how it binds with DHT.

Approximately 50% of equol circulates in the free or unbound form in humans, and this is considerably greater than the proportion of free daidzein (18.7%) or estradiol (4.6%) in plasma. Since it is the unbound fraction that is available for receptor occupancy, and presumably for binding DHT, this would effectively contribute to enhancing the overall potency of equol.

Compositions Containing Equol

The present invention includes a composition having an at least physiological acceptable quantity of equol that is able to bind and sequester free DHT (but not testosterone or DHEA) thereby preventing it binding to the androgen receptor following administration to an individual thereby having important ramifications in health and disease and a broad and important use in the treatment of androgen-mediated pathologies.

A composition containing S-equol, R-equol, a racemic equol mixture, or a non-racemic equol mixture, can be made for oral consumption. The composition or a product containing the composition can be a marketed or institutional food product, a pharmaceutical, and an OTC medicament. A food composition can comprise at least 1 mg, and typically up to 200 mg, enantiomeric equol or equol mixtures, per serving. An orally-administered medicament can comprise at least 1 mg, and typically up to 200 mg, enantiomeric equol or equol mixture, per dose. A product for topical application can comprise at least 0.1%, and up to 10%, by weight S-equol, or R-equol, or enantiomeric mixtures. A topical composition of the present invention can include other cosmetic and pharmaceutical actives and excipients. Such suitable cosmetic and pharmaceutical agents include, but are not limited to, antifungals, vitamins, anti-inflammatory agents, antimicrobials, analgesics, nitric oxide synthase inhibitors, insect repellents, self-tanning agents, surfactants, moisturizers, stabilizers, preservatives, antiseptics, thickeners, lubricants, humectants, chelating agents, skin penetration enhancers, emollients, fragrances and colorants.

An enantiomeric equol can also be an enantiomeric equol conjugate, conjugated at the C-4' or the C-7 position with a conjugate selected from the group consisting of glucuronide, sulfate, acetate, propionate, glucoside, acetyl-glucoside, malonyl-glucoside, and mixtures thereof.

A composition or preparation comprising enantiomeric or mixture of equol, for administering to subjects for the treatment and/or prevention of, or for reducing the predisposition to, androgen-related diseases and conditions related thereto, can also comprise one or more pharmaceutically acceptable adjuvants, carriers and/or excipients. Pharmaceutically acceptable adjuvants, carriers and/or excipients are well known in the art, for example as described in the Handbook of Pharmaceutical Excipients, second edition, American Pharmaceutical Association, 1994 (incorporated herein by reference). The composition can be administered in the form of tablets, capsules, powders for reconstitution, syrups, food (such as food bars, biscuits, snack foods and other standard food forms well known in the art), or in drink formulations. Drinks can contain flavoring, buffers and the like.

The composition of the invention can comprise a non-racemic mixture of S-equol and R-equol, having an EE for S-equol of more than 0% and less than 90%. A composition that has an EE of 0% is a 50:50 racemic mixture of the two enantiomers. The composition can be made directly from a racemic mixture, by an incomplete separation and removal of either the R-equol or S-equol enantiomer from the racemic mixture. The composition can also be made by combining a first equol component comprising a mixture (either a non-racemic or racemic mixture) of equol, with a second component comprising a composition consisting essentially of S-equol or R-equol. This produces a non-racemic composition that has an excess of S-equol or R-equol. Depending upon the specific benefit or indication for the R-equol component and the S-equol component in a composition, a composition can be prepared comprising S-equol and R-equol at a ratio of S-equol to R-equol from greater than about 50:50 to about 99.5:1, more typically about 51:49 to about 99:1, and from less than about 50:50 to about 1:99.5, more typically about 49:51 to about 1:99.

Compositions suitable for oral administration can be presented in discrete units, such as capsules, cachets, lozenges, or tablets, each containing a predetermined amount of the extract; as a powder or granules; as a solution or a suspension in an aqueous or non-aqueous liquid; or as an oil-in-water or water-in-oil emulsion.

The composition typically does not comprise a significant amount of any other androgen-receptor binding compound.

Identifying Equol Producers and Non-Equol Producers

Equol is formed following the hydrolysis of the glycoside conjugates of daidzein from soy, and the methoxylated isoflavone formononetin, or its glycosidic conjugates found in clover. Once formed, equol appears to be metabolically inert, undergoing no further biotransformation, save phase II metabolism or a minor degree of additional hydroxylation in the liver. As with daidzein and genistein, the predominant phase II reactions are glucuronidation and, to a minor extent, sulfation. Following the original discovery that equol's presence in urine was a function of soy food ingestion, it was observed that approximately 50-70% of the adult population did not excrete equol in urine even when challenged daily with soy foods, for reasons that are unclear. Furthermore, even when the pure isoflavone compounds are administered, thereby removing any influence of the food matrix, it has been shown that many people do not convert daidzein to equol. This phenomenon has led to the terminology of a person being an 'equol-producer' or 'non-equol producer' (or 'poor equol-producer') to describe these two distinct populations.

Cut-off values have been empirically derived permitting assignment of individuals to either of these categories. People who have plasma equol concentrations of less than 10 ng/mL (40 nmol/L) can be classified as 'non-equol producers' and where levels are above 10 ng/mL (40 nmol/L) this defines 'equol producers'. This distinction can also be derived from the levels in urine, an equol producer being someone excreting greater than 1000 nmol/L. Although the excretion of equol is highly variable among individuals there is a large demarcation between those that can produce equol and those that cannot, consistent with a precursor-product relationship in enzyme kinetics catalyzing the reaction. There is consequently an inverse relationship between urinary daidzein and equol levels, and thus far no significant gender differences have been defined.

Preparation and Isolation of Equol Enantiomers

Enantiomeric equol can be prepared per se or as the racemic mixture. Chemical synthesis routes can be used to produce the racemic mixture in good yields. In a typical synthesis process, standard chemical treatments are used to hydrogenate the double-bond of the heterocyclic ring and to remove the carbonyl at position C-3. Typical starting materials are isoflavones such as daidzein, genistein, glycitein, peurarin, formononetin and biochanin A and their glucoside conjugates. Any conjugated form would be reduced to its aglycon by hydrolysis. Suitable solvents for the reaction include organic acids such as glacial acetic acid, lower alcohols such as isopropanol, and mixtures thereof. Reduction catalysts typically employed include Palladium, such as 10% Pd on charcoal. Reactions can run at temperatures from ambient to 60° C., with pressures ranging from slightly above ambient, up to 200 psig (14 atm. gauge), and with reaction times of up to 30 hours or more.

After reaction completion, the catalyst is removed and any filtrate evaporated. The crude residue is purified, typically by chromatography employing a silica gel column, with an eluent comprising C2-C4 alcohols, C3-C7 alkanes, and mixtures thereof. The purified residue can be crystallized from n-hexane to produce (±)equol as a pure product, typically of at least 99%, with a yield typically of at least 75%. The equol crystallized product is colorless, not hygroscopic, and stable in air, and does not decompose during the final filtration procedure.

Method for the Isolation of the Individual R- and S-Enantiomers from Racemic Equol A racemic mixture of equol can be separated into its two distinct enantiomers using a chiral-phase column with a mobile phase comprising a C4-C8 alkyl and a C2-C4 alcohol. A typical example of a chiral-phase column is a Chiralcel OD column or OJ column, supplied by Daicel Chemical Industries Ltd. A preferred example of a mobile phase comprises 70% hexane and 30% ethanol. After a first period of time from passing the racemic mixture into the inlet, the time period depending upon the type of column, type of eluent, eluent flow rate, temperature, and mass of the racemic mixture, a first effluent is collected from an outlet of the HPLC column. The first eluent is typically S-equol. After a second period of time from passing the racemic mixture into the inlet, the second eluent R-equol is obtained. The elution of an equol enantiomer from the column can be detected by UV absorbance at 260-280 nm or by a more specific detection system such as a mass spectrometer and monitoring of ions specific to equol.

Biological Production of S-Equol

S-equol can be produced biologically in bulk using conventional food technology. A base solution media, food product or plant extract can be provided that comprises daidzein or another related isoflavone from which daidzein can be derived. The daidzein or other isoflavone can be converted to S-equol by a standard bacterial or enzyme fermentation process, to provide a bulk solution, food product or plant extract that comprises S-equol.

Conversion of daidzein to equol involves three major steps: 1) hydrolysis of any glucoside conjugate group, 2) conversion of the isoflavone aglycons to a dihydro-intermediate, and 3) conversion of the dihydro-intermediate to equol. The metabolic pathway and enzymes for each of the three steps required may not necessarily be present in one bacterium. Anecdotal evidence from human studies suggests that there may be one or more bacteria that act in conjunction to perform these reactions, as evidenced from the fact that often dihydrodaidzein can be present in significant amounts in plasma and urine yet equol may be low or barely detectable. Although equol may be produced from daidzein by a single organism it is believed that better or more efficient conversion can be achieved when using a mixture of bacterial species, each with its own metabolic profile. Important conditions for effective conversion to S-equol include the selection of the bacterial organism or mixture of organisms, the temperature of incubation, and the amount of oxygen available to the organisms. These conditions can be optimized by techniques well known to persons skilled in this art. The organisms used to effect this change can be inactivated by standard techniques used in the food industry or, alternately, allowed to remain in an active state in the product.

Typically, one or more bacterial strains are required to convert the daidzein (or other related isoflavone) through intermediate products to S-equol, which generally involves one or more of the three major reactions: the conversion of isoflavone glycone to aglycon isoflavone: the conversion of aglycon isoflavone to dihydro isoflavone; and the conversion of dihydro isoflavone to the product, equol. For example, a mixed culture of organisms isolated from equine feces or a mixed culture of organisms derived from the gastrointestinal tract of a person known to an 'equol producer' can convert, as they do in vivo, the glycone daidzein to the final product S-equol.

Typical bacterial strains that can convert a glycone to an aglycon (such as daidzein to daidzein) include *Enterococcus faecalis*, a *Lactobacillus plantarum. Listeria welshimeri*, a mixed culture of organisms isolated from the intestinal tract of an 'equol producing' mammal. *Bacteroides fragilis, Bifidobacterium lactis, Eubactria limosum, Lactobacillus casei, Lactobacillus acidophilous, Lactobacillus delbrueckii, Lactobacillus paracasei, Listeria monocytogenes, Micrococcus luteus, Proprionobacterium freudenreichii* and *Sacharomyces boulardii*, and mixtures thereof.

Typical bacterial strains that can convert an aglycon to equol (such as daidzein to S-equol) include *Proprionobacteria freundenreichii*, a mixed culture containing: *Bifidobacterium lactis, Lactobacillus acidophilus, Lactococcus lactis, Enterococcus faecium, Lactobacillus casei* and *Lactobacillus salivarius*; and a mixed culture of organisms isolated from the intestinal tract of an 'equol producing' mammal.

The time required for bacterial conversion of the glucosides to aglycons, or the aglycons to the equol product, will depend upon bacteria-related factors, particularly concentration, the availability of oxygen, and the temperature and pH of the incubating system. In most instances it is possible to achieve substantially complete conversion within 24 hours.

The pH range for bacterial conversion of the isoflavone glucosides to aglycon isoflavones is from about 3 to about 9. The optimum pH depends primarily upon the type of bacteria used, and should be selected accordingly.

The time required for enzymatic conversion of the glucosides to aglycons, and aglycons to the equol product, depends upon enzyme-related factors, particularly concentration, and the temperature and pH of the system. In most instances it is possible to achieve substantially complete conversion within 24 hours, more preferably within about 2 hours, and most preferably within about 1 hour.

S-equol produced in bulk can be separated from the resulting bulk solution of a bacterial production of S-equol, by methods well known in the art, including crystallization, solvent extraction, distillation, and precipitation/filtration. The resulting bulk solution can contain unreacted daidzein or other related isoflavone used, by-products, and any reactants. Such methods can include the use of a reverse-phase or straight-phase liquid chromatography column and these can be combined with chiral-phase chromatography A typical method of removing S-equol from a bulk solution or solid phase is by extraction. An extractant solution is added to the solution or solid phase containing the S-equol. Typically the extractant is a low molecular weight alcohol such as methanol, ethanol, isopropyl alcohol, or propyl alcohol, or an aqueous solution having a pH in the range from 3.5 to 5.5. Typically, if the aqueous alcohol method is being used, sufficient alcohol is added to bring the alcohol/water ratio to between a minimum of 40:60 and a maximum of 95:5. More typically, the ratio is at least 60:40, and even more typically a ratio between 65:35 and 90:10.

If an aqueous acid extraction method is used an aqueous acid solution is prepared with the pH adjusted to about 3.5 to about 5.5, and more preferably within the pH range of about 4.0 to about 5.0. Sufficient water is added to make a dilute liquid with a sufficiently low viscosity to permit separation of solids from liquids by centrifugation or filtration.

The liquid, from which insoluble solid matter has been removed, is concentrated by conventional methods for removing liquids. Methods used typically include, but are not limited to, removal of solvent by evaporation, preferably under reduced pressure. The residual liquid is concentrated to at least about 15% solids, and up to about 55% solids, more typically to between 30% and 50% solids. The concentrate is then diluted with water to reduce the solids content and increase the water to alcohol ratio. The amount of water added can be varied over a wide range, though a final solids content between 6% and 15%, and more typically about 13%, is preferred. The pH of the mixture is adjusted between about pH 3.0 and about pH 6.5, with a preferred value between about pH 4.0 and about pH 5.0. Typically the temperature is between about 2° C. to about 10° C., and more typically about 5° C. to 7° C.

The solid material is then separated from the liquid by standard separation techniques (centrifugation or filtration) and yields an equol-rich solid material.

The equol-rich material can optionally be purified, typically by chromatography employing a silica gel column, with an eluent comprising C2-C4 alcohols, C3-C7 alkanes, and mixtures thereof. The purified residue can be crystallized from n-hexane to produce S-equol as a pure product, typically of at least 99%, with a yield typically of at least 75%. The equol crystallized product is colorless, not hygroscopic, and stable in air, and does not decompose during the final filtration procedure.

The S-equol product can be authenticated by GC-MS analysis of the trimethylsilyl ether or tert-butyldimethylsilyl ether derivative, or some other appropriate volatile derivative of synthesized product as a single pure peak and a mass spectrum that is consistent with the published electron ionization spectrum of the trimethylsilyl (TMS) ether derivative of authentic equol. Confirmation of the product can also be established by direct mass spectrometry using electrospray ionization after introducing the sample into the instrument via an HPLC chiral-phase column.

Treatment of Disease by Administering S-Equol, R-Equol, and Mixtures

This present invention provides a means for an individual subject to overcome the problem of not being able to produce equol in vivo, or to supply R-equol in particular, by providing delivery of equol enantiomers, the S-equol or R-equol, or non-racemic mixtures of S-equol and R-equol directly, circumventing the need for intestinal bacteria for its production or for the need to consume soy foods with equal's precursor isoflavones. The delivery of S-equol can also supplement the in vivo production of S-equol in 'equol-producers', as well as in 'non-equol producers'.

Supplementing the diet of an equal producer with an equol enantiomer or mixture, can provide benefits when the ordinary level of S-equol produced by the equol producer is inadequate because of 1) insufficient consumption of isoflavones to produce equol, 2) antibiotic use that ablates the activity of intestinal bacteria to make equal from precursor isoflavones, or 3) other health factors that impact the level of equal production, e.g. short bowel syndrome or surgical construction of an intestinal stoma such as ileostomy. In addition, a supplemental level of equol is believed to provide enhanced effect on the health and well-being of the person.

This invention provides a method for delivering S-equol, R-equol, racemic equol, or non-racemic mixtures of equol, in sufficient amounts to have health benefits toward androgen-related diseases and conditions associated therewith. The anti-androgenic activity of equol can affect a number of tissues throughout the body. In particular, the blocking of androgenic activity of DHT can be beneficial for the treatment and prevention of: (A) growth of the prostate gland with aging, benign prostatic hyperplasia (BPH) and prostate cancer; (B) female- and male-pattern baldness, (C) facial and body hair growth (hirsutism), skin health (acne, anti-aging and anti-photo aging), skin integrity (collagen and elastin robustness); (D) body weight gain (and loss), reduction in adipose tissue deposition and metabolism of lipids, as well as general regulatory behaviors and effects, such as food and water intake, blood pressure changes, thyroid, glucose, leptin, insulin and the influence on the immune system; and (E) Alzheimer's disease and emotional, mental health issues, such as, mood, depression, anxiety and learning and memory by reducing the 5α-steroid metabolites (covering androgens and progesterone) that are potent modulators of the $GABA_A$ receptor in the brain that influences all of the brain characteristics above.

Typically, the amount of composition comprising the equol is administered in an amount sufficient to produce a transient level of enantiomeric equol in the blood plasma of the mammal of at least 5 nanograms per milliliter (ng/mL), more typically at least 10 ng/mL or greater, or transient levels of enantiomeric equol in urine of greater than 1000 nmol/L. Typically, the composition is administered orally in a dose amount of at least about 1 mg, more typically of at least 5 mg, and of up to 200 mg, more typically, up to 50 mg, of enantiomeric equol. A typical level of bioavailability of R-Equol in plasma after oral administration of 20 mg of R-equol enantiomer to a healthy adult is shown in the appearance/disappearance plots of R-equol in FIG. 2.

The ability to deliver R- and/or S-equol in sufficient amounts is believed to provide several advantages over delivery of a racemic mixture of equol. First, the potency of R-equol or S-equol alone would typically be at least twice that of the racemic mixture. Second, the human body only produces the S-equol, and therefore, a composition comprising only S-equol represents a "natural" product with an ingredient, S-equol, with which the body is familiar. Third, since the R-equol enantiomer has unique properties, a treatment composition comprising only, or substantially only, the R-enantiomer can produce beneficial and/or therapeutic effects. And fourth, administration of R-equol would supplement any endogenous S-equol present and allow for both estrogenic and anti-androgenic actions to occur in the body.

The invention includes the use of enantiomeric equol to treat and prevent diseases and conditions related to male- and female-pattern baldness. DHT is a known cause of scalp hair loss. An androgen, specifically the principal circulating androgen, testosterone, is converted to the more potent androgen, dihydrotestosterone (DHT) (in the hair follicle), and the hormonal action of DHT on scalp hair follicles cause hair loss. Thus, if the hormonal action of DHT can be blocked, such as by the use in the present invention of equol to bind DHT in the circulation (within blood vessels) and within the hair follicle], then scalp hair loss can be decreased or prevented.

The invention includes the use of enantiomeric equol to treat and prevent diseases and conditions related facial and body hair. Facial and body hair are regulated by androgens, but oppositely to that of the regulation of scalp hair. Specifically, the more potent androgen, DHT, increases facial and body hair. DHT also increases the production of sebum (oil) from the sebaceous gland, which can contribute to an increase in acne. Thus, the binding of DHT by equol can cause a decrease in facial and body hair and in secretion of sebum (oil), and a reduction or prevention of acne.

The invention includes the use of enantiomeric equol to treat and prevent diseases and conditions related to skin effects, skin quality and integrity, skin aging, skin photoaging, and skin pigmentation and lightening. Estrogens, before but especially after menopause, improve skin health by increasing elastin and collagen content to improve skin characteristics or robustness. Also, when skin is damaged by acne or other skin disruptions (scratches, popping pimples or minor cuts, etc.), the repair mechanism is faster and the skin heals better if estrogen or estrogen-like compounds, such as equol, are present. It is believed that an equol enantiomer mixture, and particularly S-equol, is a good stimulator of elastin and collagen and also can protect against photo-aging. Equol's blocking the hormone action of DHT can decrease sebum oil production from the sebaceous gland, which can decrease or eliminate acne. Since S-equol (though not R-equol) binds estrogen receptor(s) (mainly ERβ), the protective effects of this estrogen-like molecule would stimulate elastin and collagen in the skin. Additionally, since equol is a strong antioxidant, it can protect the skin from aging, including photo-aging.

The invention includes the use of enantiomeric equol to treat and prevent diseases and conditions related to improved prostate health. The conversion of testosterone to the more potent androgen DHT is the result of the action of the enzyme 5α-reductase within the prostate. DHT causes benign prostatic hyperplasia (BPH), increases in the prostate weight, and can result in the need for prostatectomies and radiotherapy to treat these conditions. Finally, consumption of soy foods has received increased attention due to their 'health benefits' of decreasing hormone dependent cancers such as prostate and breast cancer. Thus, blockage of DHT by equol decreases prostate weight in animal models and presumably will block BPH to prevent prostate cancer.

The invention includes the use of enantiomeric equol to treat and prevent diseases and conditions related to brain function and mental health, including brain disorders, dementia of the Alzheimer type, as well as other reduced or impaired cognitive functions associated with advancing age and with short- and long-term memory loss. Brain mechanisms are more complex, and attempting to define what molecules and factors regulate, influence, etc., mood, depression, anxiety and so on, can be difficult. However, there are some data to support the concept that estrogens or estrogen-like molecules like isoflavones can assist cognitive function in conditions such as Alzheimer's disease, and may help to prevent the onset of such disorders, especially in postmenopausal women.

In reference to mood, anxiety, depression, and other mental health conditions, there are two basic viewpoints. One line of research supports the view that estrogens (especially in women) regulate anxiety and help to decrease anxiety levels. Both estradiol and progesterone alter anxiety-related behaviors as well as the testicular androgen, testosterone (Imhof J. T. et al, Behav Brain Res, 56:177-180 (1993). The anti-androgenic activity of equol acts in the brain by enhancing neurotransmission and restoring synaptic density. Without being bound by any particular theory, we believe that R- and/or S-equol are active in the brain at the same site(s) as estrogen, exerting an estrogenic response.

The second line of research is more complex and supports the view that 5α-reduced steroids, especially progesterone, have the ability to bind $GABA_A$ receptors in the brain and cause sedation. $GABA_A$ is the major inhibitory neurotransmitter in the brain and its receptors are abundant in brain areas that control mood/emotion. By causing sedation, individuals express less anxiety. For example, most women during pregnancy, report that they feel OK but they are usually tired or sleepy. This is due to progesterone being converted by the 5α-reductase enzyme in the body, but especially in the brain to 5α-dihydroprogesterone (5α DHP) and further metabolism of this molecule results in the most potent 'neurosteroid' that can bind the $GABA_A$ receptor and enhance the action of $GABA_A$. Additional supporting evidence that this 5α-dihydroprogesterone molecule (and its metabolite) can decrease brain activity is seen in epileptic women (who experience epilepsy and hence seizures) where these individuals almost never experience seizures during pregnancy due to the high circulating levels of progesterone. It should be noted that 5α-reduced androgens like 5α-DHT also have a similar effect on $GABA_A$ receptors to cause sedation (in men) but at much lower levels compared to 5α-DHP.

Putting these two views together, estrogen on the one hand decreases anxiety and hence increases activity. Conversely, blocking the action of 5α-DHP also increases activity and thus in behavioral tests is interpreted as decreasing anxiety. For example, when the conversion of progesterone to 5α-DHP in pregnant rats has been blocked, this results in a significant increase in their locomotor activity levels.

Taking a similar perspective on this in reference to equol, equol has the ability to bind 5α-DHP (mainly seen in women) and 5α-DHT (mainly seen in men). This would decrease the potent 'neurosteroid' effects at the $GABA_A$ receptor and decrease sedation and thus increase activity or decrease anxiety. Moreover, the ability of S-equol to bind the estrogen receptor(s) beta would also increase activity. Finally, our studies using young- or mid-aged adult rats, in males or females have shown that dietary phytoestrogen consumption (Lund T. D. et al. Brain Res, 913:180-184 (2001); Lephart, E. D. et al, Neurotoxicology Teratology, 24: 1-12 (2002)), or injections with equol significantly decrease anxiety levels as expressed in the elevated plus maze test.

One report, conversely, suggests that isoflavones can increase anxiety in male rats (Hartley et al., Psychopharmacology, 2003, 167:46-53).

The elevated plus maze is a behavioral test used to quantify anxiety-related behavior and identify anxiolytic drugs (Pellow S. et al, J Neurosci Methods, 14:149-147 (1985); Current Protocols In Neuroscience (1997) 8.3.1-8.3.15, John Wiley & Sons. NY, N.Y.). The test relies on the inherent conflict between exploration of a novel environment and avoidance of its aversive features. Normally, animals spend little time and make few entries into the open arms of the maze compared to the closed arms of the maze (Imhof J. T. et al., Behav Brain Res, 56:177-180 (1993). However, animals treated with anxiolytics, such as benzodiazepines (valium), spend more time in the open arms and the number of entries into the open arms reflects a decrease in anxiety-related behaviors (Pellow S. et al, J Neurosci Methods, 14:149-147 (1985); Current Protocols In Neuroscience (1997) 8.3.1-8.3.15. John Wiley & Sons. NY, N.Y.; Chopin P. et al., Psychopharm, 110:409-414 (1993).

The invention includes the use of enantiomeric equol to treat and prevent diseases and conditions related to body weight and body fat formation. Phytoestogens including equol, have the ability to decrease the formation of white adipose (fat) tissue and increase white adipose tissue breakdown, thus decreasing body weight. Also, the estrogen-like nature of phytoestrogen molecules decreases LDL (so-called "bad" cholesterol), blood pressure, and prevents insulin resistance (or in other words, provides beneficial effects to the diabetic condition). Since equol is a more potent isoflavone molecule compared to the other phytoestrogens, it presumably provides the health benefits and protects against the conditions outlined above.

Since equol binds DHT, equol can also block the actions of DHT that promote body weight gain. Thus, equol, and particularly S-equol, combined anti-androgenic but at the same time an estrogenic hormone action from the same molecule (equol) would further improve the health benefits of body weight loss (and weight management), decrease LDL cholesterol, decrease blood pressure, and help prevent the devastating effects of diabetes.

The invention includes the use of equol, as enantiomeric equol or mixture thereof, to treat and prevent lipid disorders such as high cholesterol (hypercholesterolemia), lipidemia, lipemia and dyslipidemia (disturbances in lipids). A study has shown that plasma total cholesterol concentrations decreased 7.2% (p=0.04) in equol producers compared with baseline levels and 3.0% (p=NS) in non-equol producers. The failure of soy protein to have significant cholesterol-lowering effects in adults with normal blood cholesterol levels, is, with few exceptions, probably because of heterogeneity in the study populations with regard to the metabolism of soy isoflavones and the failure to recognize the relevance of equol formation (and specifically, non-formation in non-equol producers). These data suggest that enantiomeric equol influences lipids in a favorable manner, and that the effect is mediated by androgens. The composition comprising equol is administered in an amount sufficient to reduce the level of lipids in the blood stream.

The invention further includes the use of R- and/or S-equol to improve diminished blood vessel quality, by increasing reactivity or flexibility in response to acute changes in blood pressure, improving blood flow, and reducing blood pressure. The invention also includes the use of R- and/or S-equol to treat and prevent cancer, including benign prostate cancer, prostate cancer, and skin cancer.

Another embodiment of the present invention is the use of equol to treat enlarged prostate or epididymis. Equol may also be used to prevent enlarged prostate or epididymis in individuals believed to be at risk for development of these pathologies, without alterations in testes, pituitary or body weights. The equal may be administered by any route that allows absorption of equal to the blood stream.

DHT-Androgen Receptor

Other embodiments of the present invention include the use of equol as a diagnostic agent in androgen-related disorders as well as disorders arising from disturbances in estrogenic/androgenic balance. In these embodiments, equol is administered to an individual to bind DHT and thereby prevent DHT binding to androgen receptors. The changes in estrogenic balance are then measured or the change in androgen-binding is assessed to diagnose or further elucidate androgen-related anomalies.

Binding to DHT

Equol can be administered to bind DHT prior to or along with other therapeutic moieties in order to assess the binding capacity of DHT with respect to the therapeutic moiety in question. Also, androgen-binding moieties can be administered following administration of equol to assess the efficacy of the androgen-binding moiety to restore androgen activity and balance estrogenic activity in the absence of DHT binding. Further, equol can be administered in the presence of DHT-binding moieties in order to displace these naturally-occurring or xenobiotic DHT-binding moieties from DHT.

Administration of Equol

In each of the embodiments of the present invention described herein, if the administration of equol is to be oral, the equol may be administered by supplying an oral dosage form of equol to either an "equol-producing" mammal or a "non-equol producing" mammal, or an oral dosage of daidzein, daidzin, isoflavone mixtures containing daidzein, or soy protein preparations to an "equol-producing" mammal, wherein the administration of the oral dosage form results in effective absorption of equol to the blood stream. Administration of equol may be made by routes other than oral if desired. For example, it is contemplated that rectal or urethral administration may be used to administer equol for the treatment of enlarged prostate or to prevent prostate enlargement. Additionally, it is contemplated that the active ligand binding site of the equol molecule may be isolated and synthesized for administration, which can provide DHT binding without the full equol molecule. The dose of the equol molecule or fragment thereof having DHT-binding abilities is dependent upon the route of administration and the condition to be treated. Based on our in vivo studies it is apparent that relatively low doses of equol antagonize much higher doses of DHT, and this may be explained by the marked differences in the binding of equol to serum protein compared with DHT. The latter circulates mostly bound to proteins, while equol is 50% free. Generally, a dose sufficient to produce a concentration of equol or active fragments thereof in the bloodstream of the recipient of at least about 0.2 mg equol per kg weight of the recipient and preferably at least about 0.5 mg/kg. The dose may be increased dramatically without incurring significant dose-limiting side effects to greater than about 10 mg/kg. Oral administration can be effected in microencapsulated forms that can provide delayed or sustained release of the medicament.

Equol can be administered topically, transdermally, and subdermally in a variety of forms, including lotions, ointments, foams (including shaving creams), nasal sprays, skin patches (such as described in U.S. Pat. No. 5,613,958, incorporated herein by reference), electromechanical devices, including micropumps systems (such as described in U.S. Pat. No. 5,693,018 and U.S. Pat. No. 5,848,991, incorporated herein by reference), and subdermal implants (such as described in U.S. Pat. No. 5,468,501, incorporated herein by reference).

Experiments (a) Determination of Equol Enantiomer in 'Equol-Producing' Adults

Figure 3:
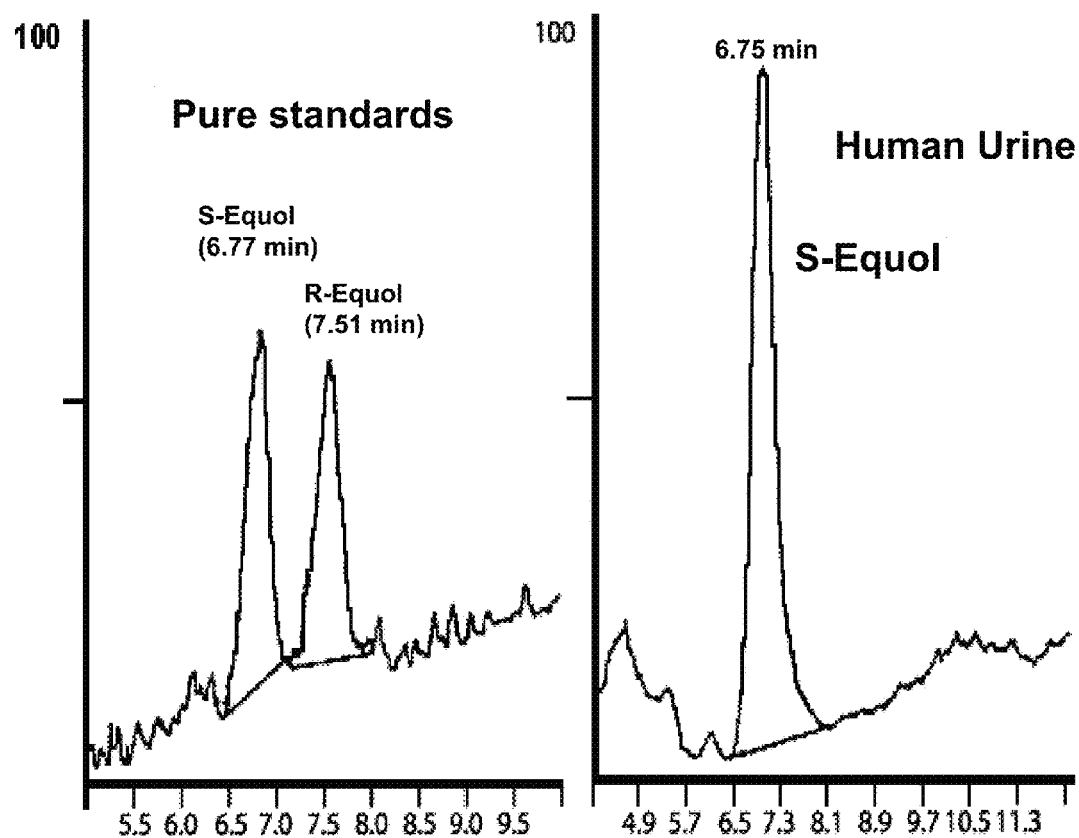
FIG. 3 shows a mass chromatogram of the elution of the equol enantiomers from a sample of urine from an adult consuming soy food, compared against pure enantiomeric standards that had been characterized by optical dichroism.

The urine samples from adults consuming soy foods previously identified as being 'equol-producers' were analyzed. Equol was isolated from urine (25 mL) by passage of the sample through a solid-phase Bond Elut C18 cartridge. After washing the cartridge with water, the isoflavones were recovered by elution with methanol (5 mL) and the methanolic phase was taken to dryness under a stream of nitrogen. The sample was subjected to enzymatic hydrolysis with *Helix pomatia* and then re-extracted on a Bond Elut C18 cartridge. The methanolic extract was taken to dryness under nitrogen gas and redissolved in HPLC mobile phase (100 μL). Equol enantiomers were identified by HPLC using a Chiralcel OJ chiral phase column as described herein above. The detection of equol was achieved by selected ion monitoring electrospray ionization mass spectrometry (ESI-MS). Mass chromatograms of a pure standard of S-equol, and of urine from an adult consuming soy food are shown in FIG. 3. Similar studies have demonstrated that soy-derived isoflavones are converted to equol in rats, as well, thus validating rodent models of isoflavone metabolism.

The retention index and mass chromatogram establish that it is exclusively the S-enantiomer of equol that is excreted in human urine as no detectable R-enantiomer of equol could be found. Analysis of the plasma from the same 'equol-producer' also revealed only the S-enantiomer of equol.

(b) Chemical Synthesis of Racemic Equol

Figure 4:
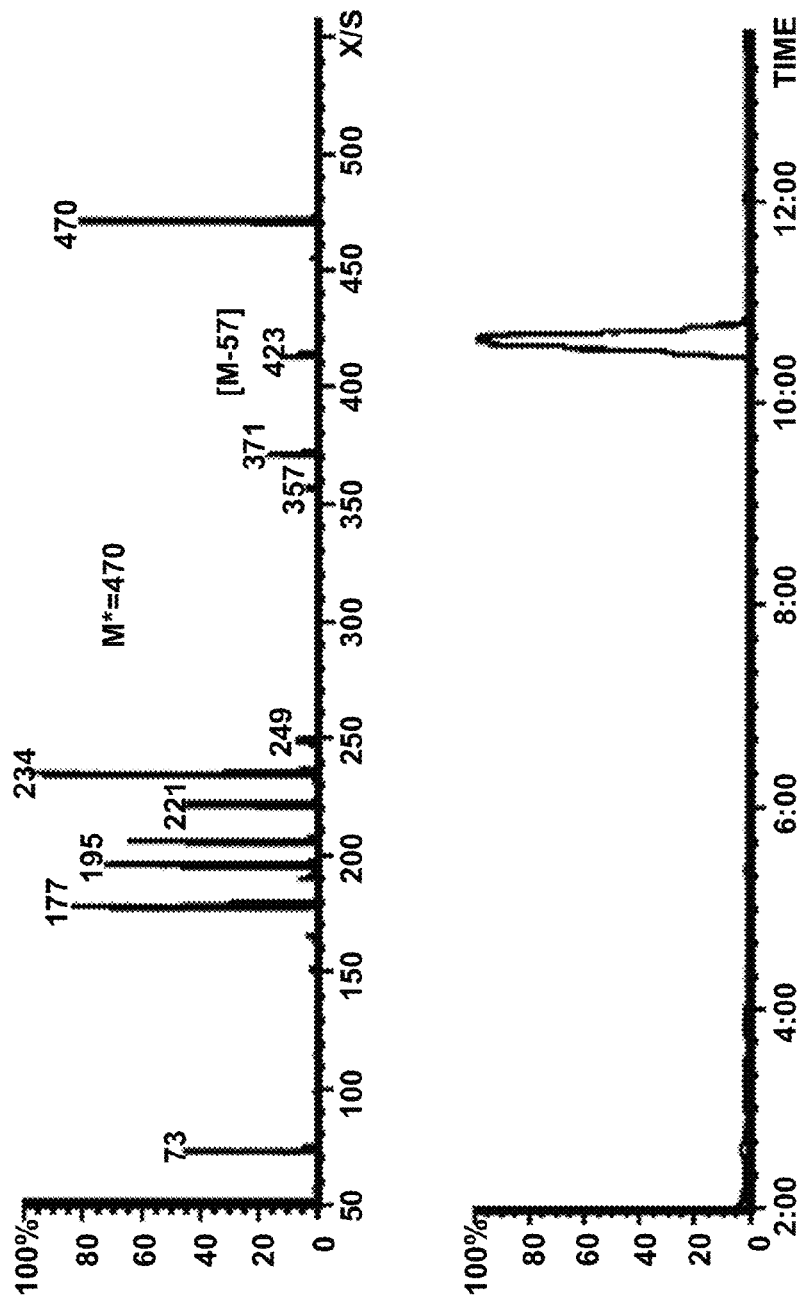
FIG. 4 shows the GC-MS analysis of the trimethylsilyl ether derivative of synthesized product.

Daidzein (200 mg, 0.8 mmol) is dissolved in a mixture of glacial acetic acid (20 mL) and isopropanol (20 mL), and is reduced with 10% Pd on charcoal (150 mg) at 55 p.s.i.g. (3.7 atm gauge). At the end of the reaction (2 hours, TLC:isopropanol/n-hexane 1/4) the catalyst is filtered off, and the filtrate is evaporated. The crude residue is purified by chromatography on a silica gel column using as eluent a mixture of isopropanol and n-hexane (1:4 v/v), to give (±)equol as a pure product (160 mg, yield: 82%) crystallized from n-hexane. The product, colorless crystals, is not hygroscopic, is stable in air, and does not decompose during the final filtration procedure. The product of this chemical synthesis was in all respects identical with an authentic sample of (±)equol (racemic equol). FIG. 4 shows the GC-MS analysis of the trimethylsilyl ether derivative of synthesized product as a single pure peak and a mass spectrum that is consistent with the published electron ionization spectrum of the trimethylsilyl (TMS) ether derivative of authentic equol. The molecular ion as expected is at m/z 470 and the base peak at m/z 234. The purified equol product had a purity of greater than 99%, as confirmed by HPLC and mass spectrometry.

(c) Elution Order of S- and R-Enantiomer by Optical Dichroism

A racemic mixture of S-equol and R-equol were separated by chiral chromatography on a Chiralcel OJ Column using a flow-rate of 1.0 mL/min and with a gradient elution consisting of an initial mobile phase of 10% ethanol in hexane and increasing to 90% ethanol in hexane over a time period of 15 minutes according to the program shown in Table 1:

TABLE 1

Chiral separation gradient eluent of hexane and ethanol

| Time (min.) | % hexane | % ethanol |
|---|---|---|
| 0 | 90 | 10 |
| 1.0 | 90 | 10 |
| 15.0 | 10 | 90 |
| 16.0 | 90 | 10 |
| 17.0 | 90 | 10 |

Figure 5:
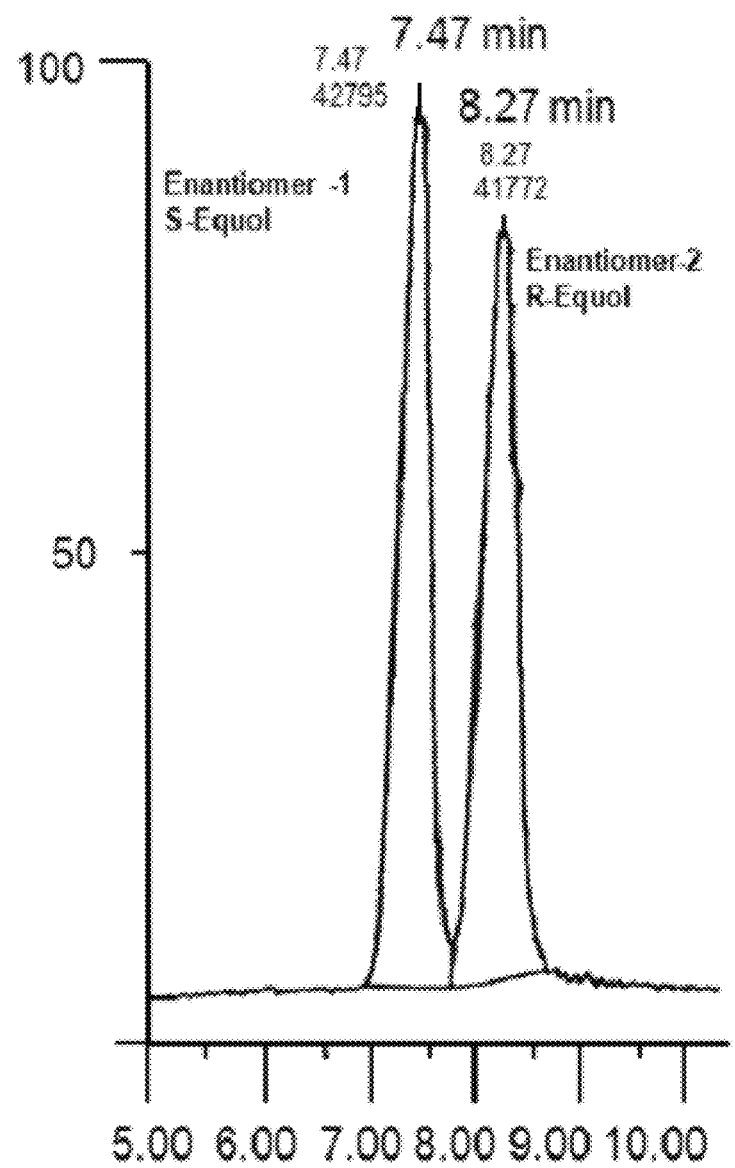
FIG. 5 shows a mass chromatogram of a chiral separation of S-equol and R-equol from a racemic mixture.

FIG. 5 shows the mass chromatogram of the ions recording (m/z 241) for a racemic mixture of S- and R-equol.

The first eluting material, designated as Enantiomer-1, and the second eluting material, designated as Enantiomer-2, were collected separately. Each enantiomer was weighed and the weighed samples dissolved in 1 mL of spectroscopic grade ethanol. Measurement of the optical rotation of each enantiomer was carried out at 20° C. using the light of wavelength in the line D of sodium.

Enantiomer-1 material (1.6 mg exact weight) had first and second measurements of −0.023 and −0.022, resulting in an optical rotation of −14 [−0.0225×1000/1.6], which corresponds with the S-enantiomer of equol. Enantiomer-2 material (1.7 mg exact weight) had first and second measurements of +0.023 and +0.023, resulting in an optical rotation of +13.5[+0.023×1000/1.7], which corresponds with the R-enantiomer of equol.

d) Determination of Receptor Binding Capacity of S- and R-Enantiomers

In vitro binding studies were performed to examine the relative affinities of S- and R-enantiomeric equol with the estrogen receptors ERα and ERβ.

Synthesis of Hormone Receptor Proteins: Full length rat ERα expression vector (pcDNA-ERα: RH Price UCSF) and ERβ expression vector (pcDNA-ERβ; TA Brown. Pfizer. Groton, Conn.) were used to synthesize hormone receptors in vitro using the TnT-coupled reticulocyte lysate system (Promega, Madison, Wis.) with T7-RNA polymerase, during a 90 min reaction at 30° C. Translation reaction mixtures were stored at −80° C. until further use.

Saturation isotherms: In order to calculate and establish the binding affinity of the S-equol and R-equol enantiomers for ERα and ERβ, 100 μL aliquots of reticulocyte lysate supernatant were incubated at optimal time and temperature: 90 min at room temperature (ERβ) and 18 hrs at 4° C. (ERα), with increasing (0.01-100 nm) concentrations of [3H]17β-estradiol (E2). These times were determined empirically and represent optimal binding of receptor with estrogen. Nonspecific binding was assessed using a 300-fold excess of the ER agonist, diethylstilbestrol, in parallel tubes. Following incubation, bound and unbound [3H]E2 were separated by passing the incubation reaction through a 1 mL lipophilic Sephadex LH-20 (Sigma-Aldrich Co., Saint Louis, Mo.) column. Columns were constructed by packing a disposable pipette tip (1 mL; Labcraft, Curtin Matheson Scientific, Inc, Houston, Tex.) with TEGMD (10 mm Tris-Cl, 1.5 mm EDTA, 10% glycerol, 25 mm molybdate, and 1 mm dithiothreitol, pH 7.4)-saturated Sephadex according to previously published protocols (Handa et al., 1986: O'Keefe and Handa, 1990). For chromatography, the columns were re-equilibrated with TEGMD (100 μL), and the incubation reactions were added individually to each column and allowed to incubate on the column for an additional 30 min. Following this incubation, 600 μL of TEGMD were added to each column, flow-through was collected, 4 mL scintillation fluid was added, and samples were counted (5 min each) in an 2900 TR Packard scintillation counter (Packard Bioscience, Meriden, Conn.).

Competition binding studies were used to assess the estrogenic properties of equol's S-equol and R-equol enantiomers. Based on the ability of S and R to compete with [3H]E2 for ER binding, the affinities for in vitro translated ER were shown to be very different for the two enantiomers. The S-equol enantiomer showed greatest affinity for ERβ [Kd (nm)=0.73±0.2], while its affinity for ERα was relatively low by comparison [Kd(nm)=6.41±1.0]. The R-equol enantiomer possessed a much lower affinity for both ERβ [Kd (nm)=: 15.4±1.3] and ERα [Kd (nm)=27.38±3.8]. For reference 17β-estradiol binds ERα with a Kd (nm)=0.13 and ERβ with a Kd (nm)=0.15 in this system.

Figure 2:
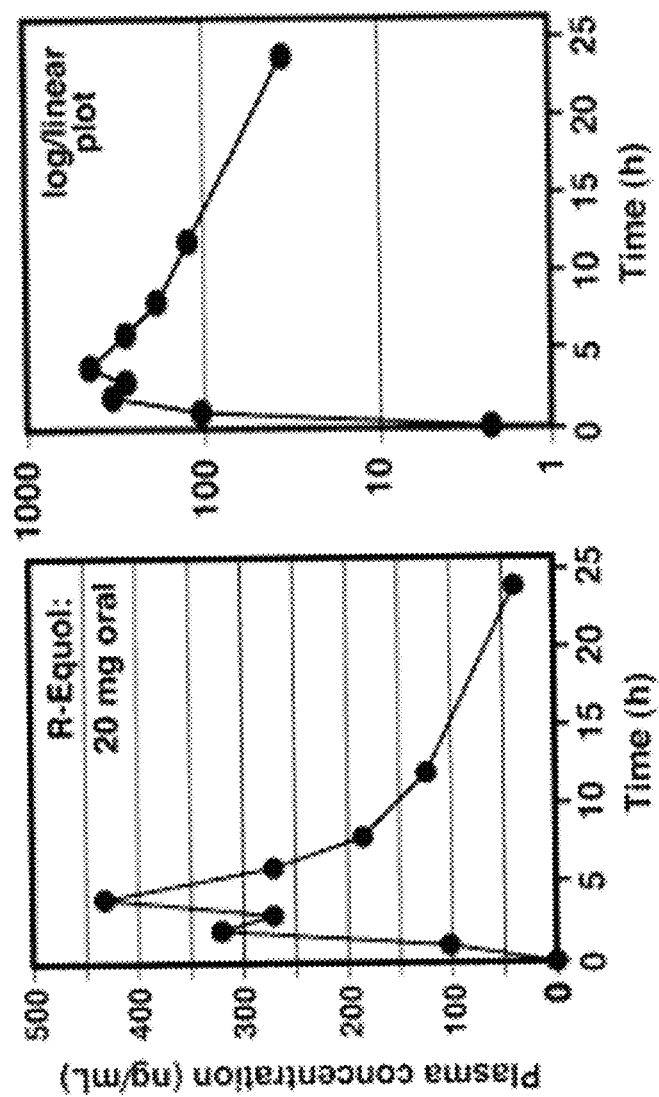
FIG. 2 shows an appearance/disappearance plot of R-equol in plasma after oral administration of R-equol to a healthy adult.

The study shows that only the S-equol enantiomer binds ER with sufficient affinity to have potential relevance to circulating equol levels reported in humans. Compared with 17β-estradiol the relative binding affinities of the S-equol and R-equol enantiomers for ERα were 49-fold and 211-fold less, respectively. However, the S-equol enantiomer seems to be largely ERβ-selective with a relatively high affinity for ERβ, while the R-equol enantiomer binds with approximately 100-fold less affinity. The separate and associated determination that exclusively S-equol is found in human plasma and urine is significant in view of the specificity in binding of the two enantiomers.

e) Bioavailability of R-Equol 20 mg of pure R-equol was administered orally to a healthy adult after an overnight fast. Blood samples were collected at timed intervals over the next 24 hours and the plasma concentration of equol was determined by isotope dilution gas chromatography-mass spectrometry with selected ion monitoring. Rapid appearance of equol is observed in the plasma with peak concentrations observed after 8 hours. The terminal elimination half-life of R-equol was approximately 8 hours. Electrospray ionization mass spectrometry confirmed that the equol present in plasma was the R-equol enantiomer (data not shown but available on request), thereby establishing that it is stable and does not undergo any racemization or further biotransformation in the intestine. FIG. 2 shows an appearance/disappearance plot of R-equol. These results establish that R-equol if administered as a pharmacologic or nutraceutical preparation is extremely bioavailable.

EXAMPLES

Where appropriate, data were analyzed by analysis of variance statistics (ANOVA) followed by Newman-Keuls post hoc tests. Significance was set at p<0.05. Curve fitting, scientific graphing, and analysis were completed using Graph-Pad Software (GraphPad Prism 3.0, San Diego, Calif.).

Example 1

This example demonstrates the in vivo effects of equol on prostate size and hormone secretion. Male Sprague-Dawley rats (400-500 grams) are obtained from Charles Rivers Laboratories (Wilmington, Mass., USA). Rats are caged in pairs and maintained on a 12-hour dark 12-hour light schedule (lights on at 0700 h) with ad libitum access to food and water.

One week following arrival, animals are given subcutaneous (sc) injections (1/day for 4 days) of either dimethylsulfoxide (DMSO) (vehicle control) or racemic equol (0.25 mg/kg). Eighteen hours after the final injection, animals are killed via decapitation and trunk blood and prostate are collected for analysis.

Figure 6A:
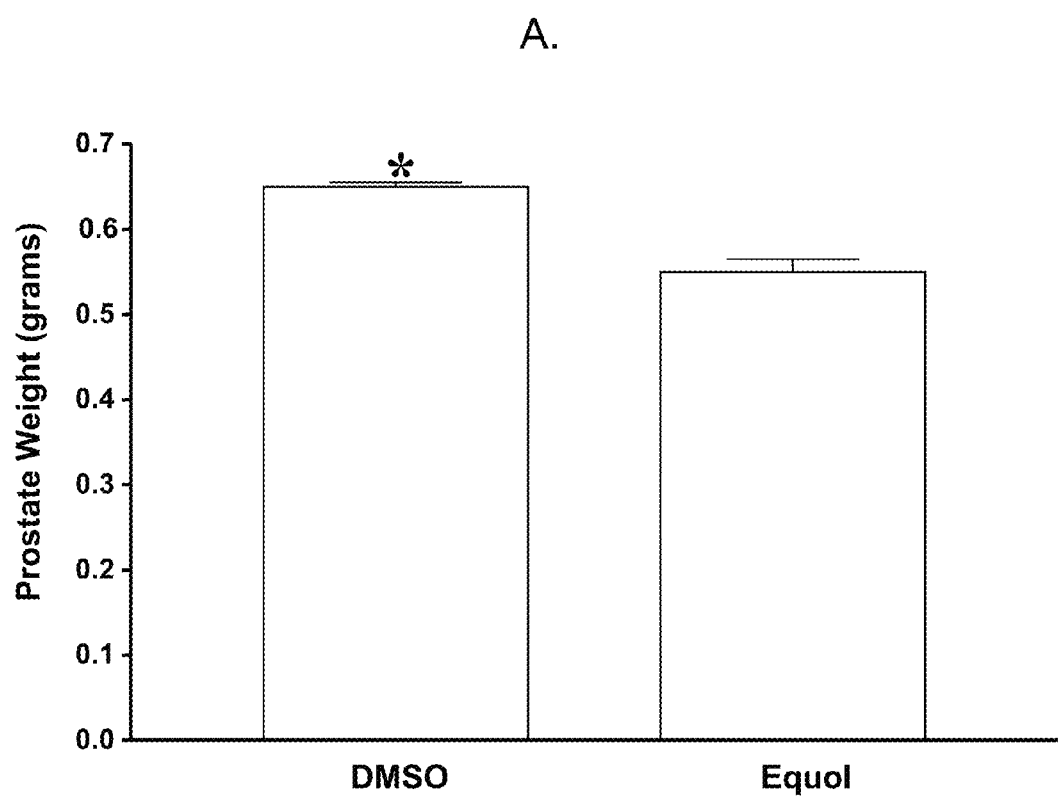
FIG. 6A shows prostate weight for in intact male rats subcutaneously injected with DMSO or equol.
Figure 6B:
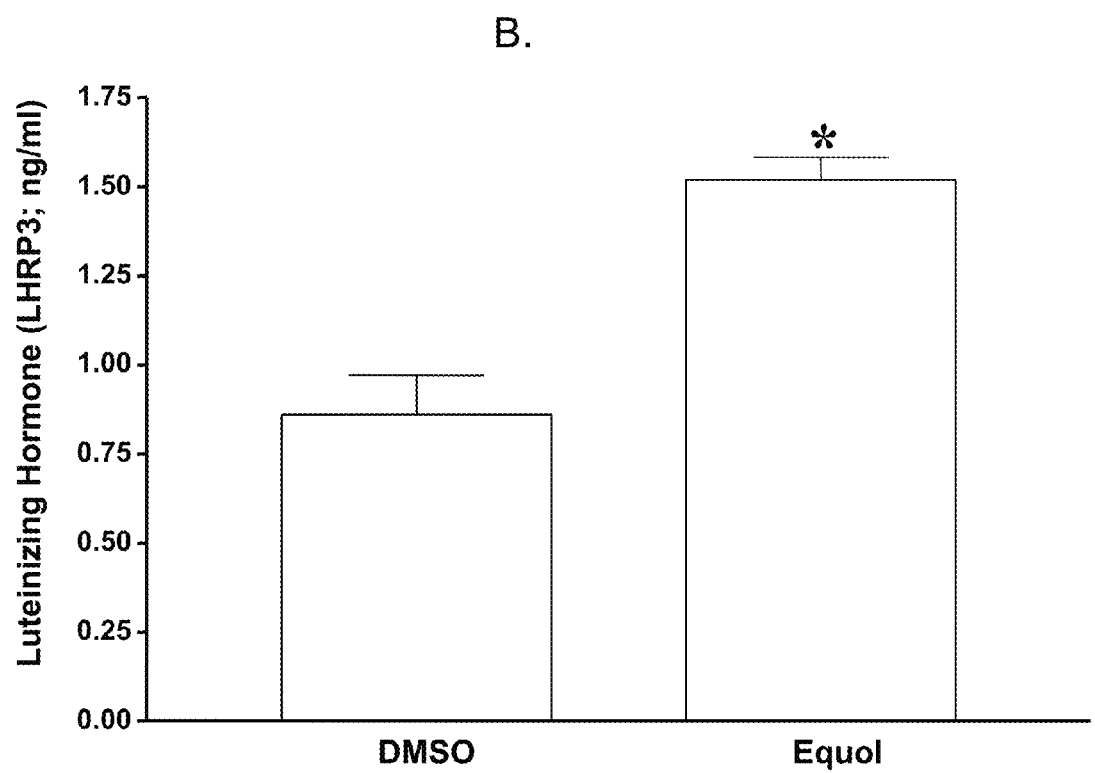
FIG. 6B shows lutenizing hormone (LH) for in intact male rats subcutaneously injected with DMSO or equol

A significant reduction in prostate weight is observed in intact males injected subcutaneously with equol in comparison to intact control males. Additionally, luteinizing hormone (LH) in these same intact males is significantly increased in equol compared to control treated males. These finding are shown in FIGS. 6A and 6B, respectively. These effects are observed with relatively low levels of equol compared to DHT and this can be explained by the marked differences in the protein binding of equol, which circulates about 50% free, and DHT which is mostly bound to serum protein.

Example 2

In addition to equol's effects on prostate racemic equol blocks the effects of DHT in other tissues, and decreases body weight. One week following arrival, intact males are given subcutaneous injections of either DMSO (control) or equol (0.5 mg/kg) once/day for 7 days. Following treatments animals are weighed and then killed via decapitation and tissue collection (prostate, testes, epididymis, and pituitary).

A significant weight decrease in the DHT-sensitive epididymis is observed in racemic equol-treated males compared to controls. However, racemic equol did not affect testes weight or pituitary weight. Body weight during this relatively brief treatment period does not differ significantly between racemic equol and control treatments. These results are presented in Table 2.

TABLE 2

Tissue weights from intact males given subcutaneously injections of either DMSO (control) or racemic equol.

| | Prostate (g) | Epididymis (g) | Testes (g) | Pituitary (g) | Body (g) |
|---|---|---|---|---|---|
| DMSO (Control) | 0.58 (±0.05) | 1.91 (±0.10) | 3.52 (±0.10) | 0.011 (±0.003) | 428.2 (±4.04) |
| Racemic Equol (0.25 mg/kg) | 0.38 (±0.06)* | 1.59 (±0.06)* | 3.48 (±0.08) | 0.014 (±0.002) | 418.0 (±7.52) |

Example 3

Adult male Sprague-Dawley rats are randomly assigned to three groups and receive daily injections of either DMSO, a racemic mixture of equol at 0.250 mg/kg/day), R-equol at 0.250 mg/kg/day, or S-equol at 0.250 mg/kg/day. The total volume of each injection is 0.3 cc, administered sc at the nape of the rat's neck. After seven consecutive days of treatment, the rats are killed and the body weight gain during the injection period is determined. Rats injected with R-equol have a significant decrease in body weight gain compared to control rats, as shown in Table 3.

TABLE 3

Body Weight Gained in Male Sprague-Dawley Rats Treated with Equol.

| Treatment Group | Prostate (g) | Epididymis (g) | Body Wt Gain (g) |
|---|---|---|---|
| Control | 0.38 (±0.01) | 0.96 (±0.03) | 59.4 (±3.4) |
| Racemic Equol (0.25 mg/kg) | 0.35 (±0.02) | 0.89 (±.03) | 56.1 (±3.7) |
| R-equol (0.25 mg/kg) | 0.31 (±0.02)* | 0.85 (±0.04)* | 45.6 (±5.5)* |
| S-equol (0.25 mg/kg) | 0.35 (±0.03) | 0.86 (±0.05) | 56.1 (±3.1) |

*Significant reduction compared to control

Testis and pituitary gland weights are not significantly altered by the treatments (data not shown). The slight decreases in body weight (around 10%) from the equol experiments are very similar to those seen between animals fed a Phyto-Free diet (a diet containing very low levels of phytoestrogens) vs. a Phyto-600 diet (a phytoestrogen-rich diet containing 600 ppm of isoflavones). The significant reduction in white adipose tissue deposition with the racemic equol injections (around 36%) is also comparable with that seen with the data sets derived from the dietary treatment studies. These findings suggest that R-equol can regulate body weight and significantly decrease white adipose deposition.

Example 4

This Example demonstrates equol binding to DHT. In initial binding competition studies conducted to determine and establish equol's binding affinity for AR, we repeatedly observed that the apparent binding of [3H]DHT was greater in the presence of equol than in its absence. Slight modifications in the protocol where AR was removed from the incubation tube (leaving only [3H]DHT and equol) resulted in the elution of [3H]DHT into the eluate containing [3H]DHT reaction complex.

Figure 7:
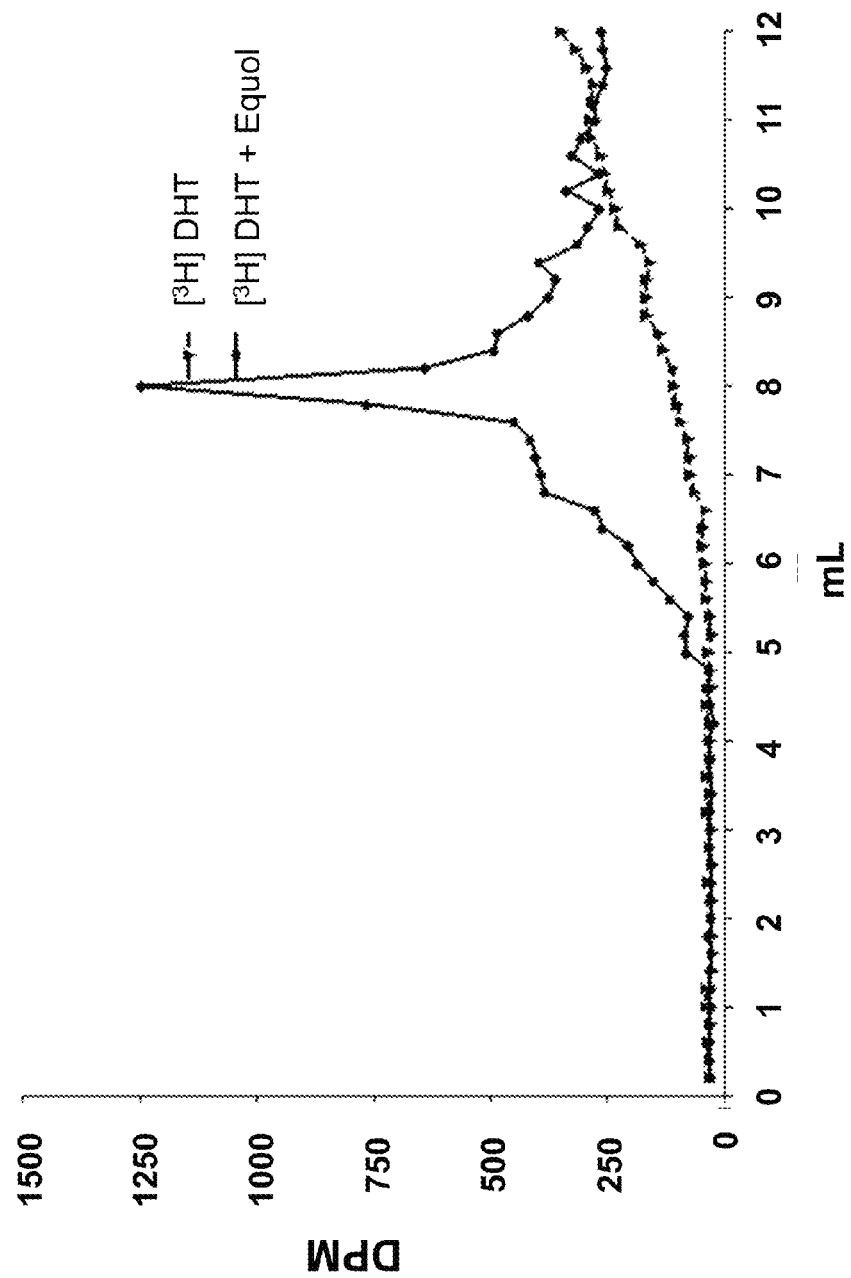
FIG. 7 shows a distinct peak in [3H] DHT+equol but not [3H] DHT alone.
Figure 8A:
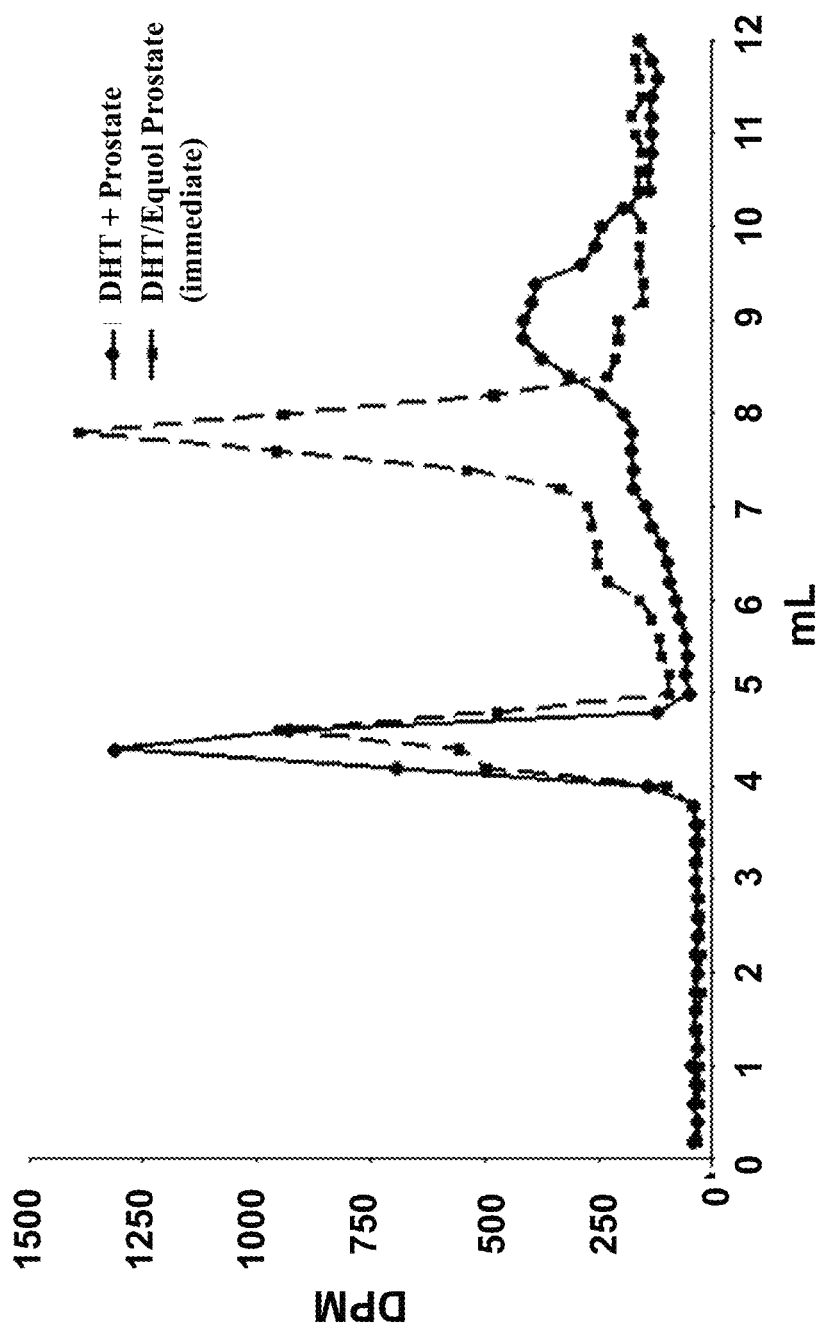
Figure 8B:
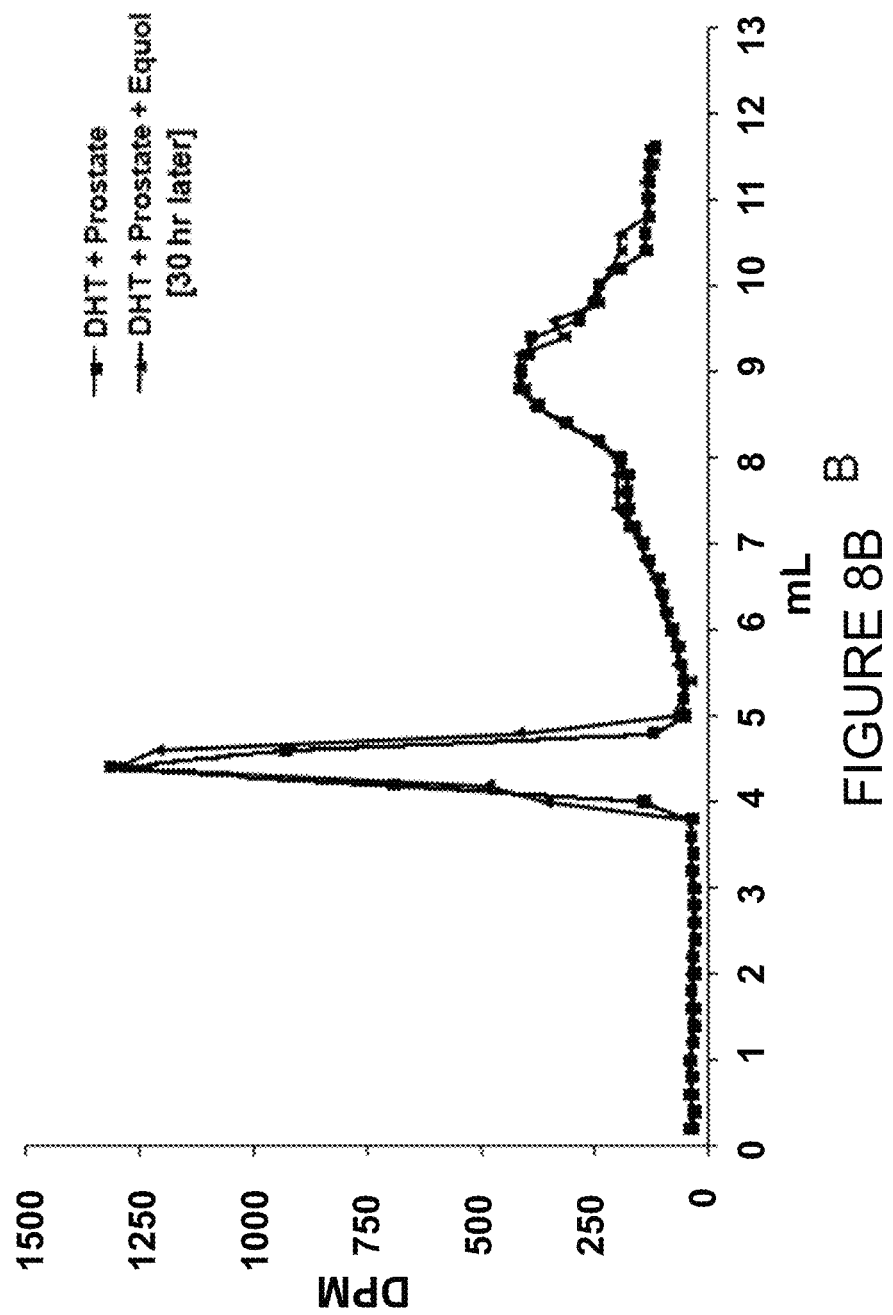
FIG. 8B shows only a single peak is present in [3H]-DHT incubated with prostate (B).
Figure 9:
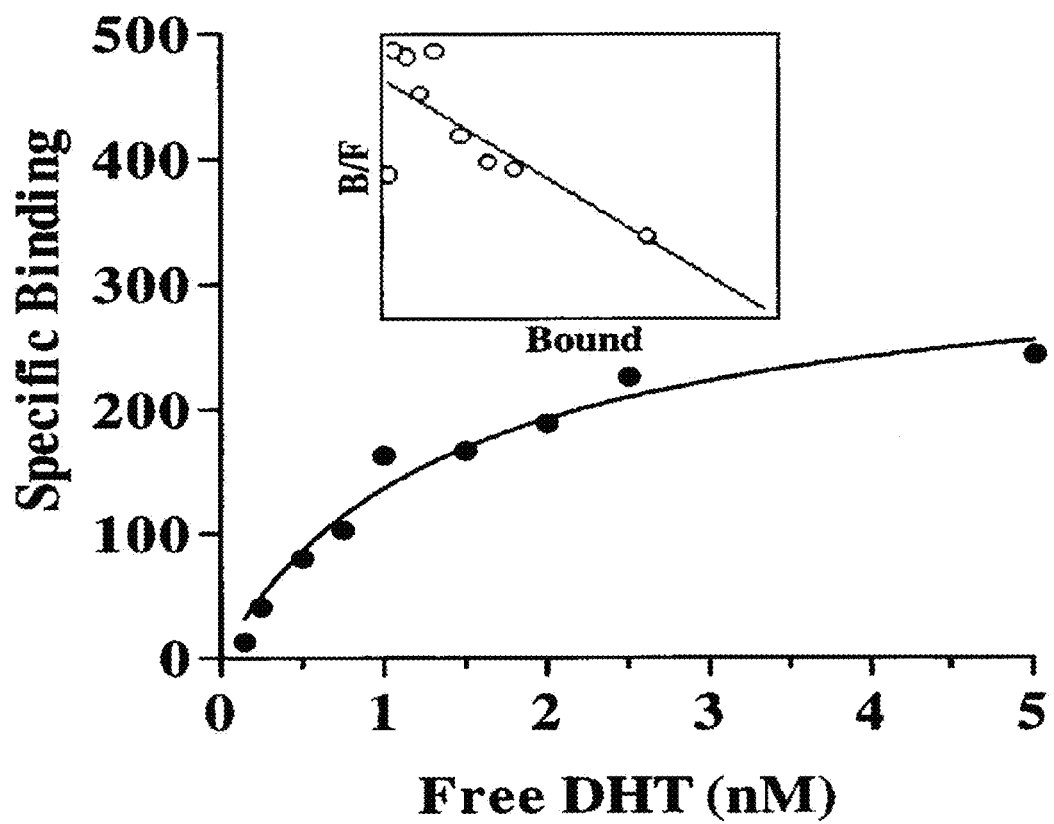
FIG. 9 shows the specific binding of equol to [3H]-DHT.

To further investigate this phenomenon, a 30 cm long Sephadex LH-20 columns are used in order to identify elution peaks establishing the binding of [3H]DHT to equol. As shown in FIG. 7, a peak of [3H]DHT is apparent in the elution fractions between 5 and 9 mL when the [3H]DHT+equol column incubate is applied. This peak is not present when [3H]DHT alone is applied to the column. Furthermore, when DHT or DHT+equol are incubated with prostate supernatant and then passed through the 30 cm column (FIG. 8A) two distinct binding peaks are identifiable. The first peak of [3H] DHT represents that bound to the AR in prostate. This is found in the elution fractions between 4 and 5 ml. In addition there is a later peak (between 5 and 9 ml), consistent with the binding of [3H]DHT to equol. However, when [3H]DHT is allowed to incubate with the prostate supernatant for 36 hours (until equilibrium) prior to the introduction of equol there is no apparent binding of [3H]DHT (FIG. 8B). Both [3H]DHT and [3H]DHT+equol (equol added 36 hours later) show a single peak in the elution between 4 and 5 ml, suggesting that equol does not compete with DHT for the AR nor does it bind [3H]DHT that is already bound to the receptor. Furthermore, it should be noted that the binding of equol to DHT appears to be specific, since similar competition and binding studies have been conducted using [3H]E2, [3H]T, [3H]DHEA, [3H] CORT and [3H]progesterone without any occurrences of binding to equol (data not shown). Saturation analysis of equol binding to [$^3$H]DHT shows an apparent Kd calculated at 1.32±0.4 nM (FIG. 9).

Example 5

Figure 10A:
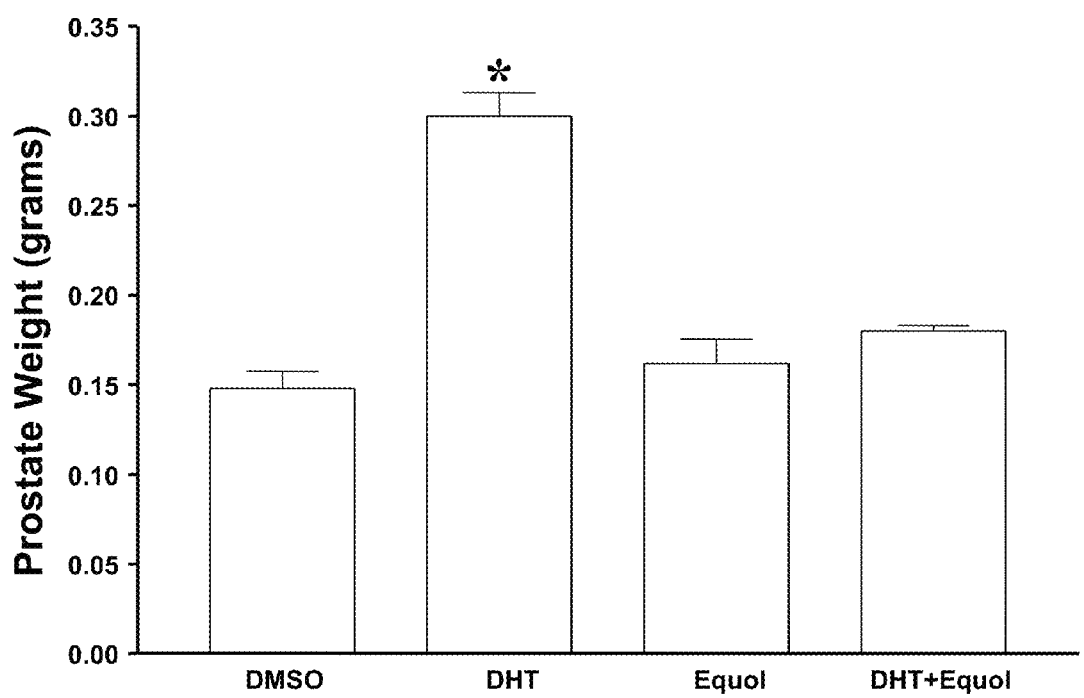
FIG. 10A shows prostate weight in gonadectomized (GDX) male rats sc injected with DMSO, DHT, equol, or both DHT and equol.
Figure 10B:
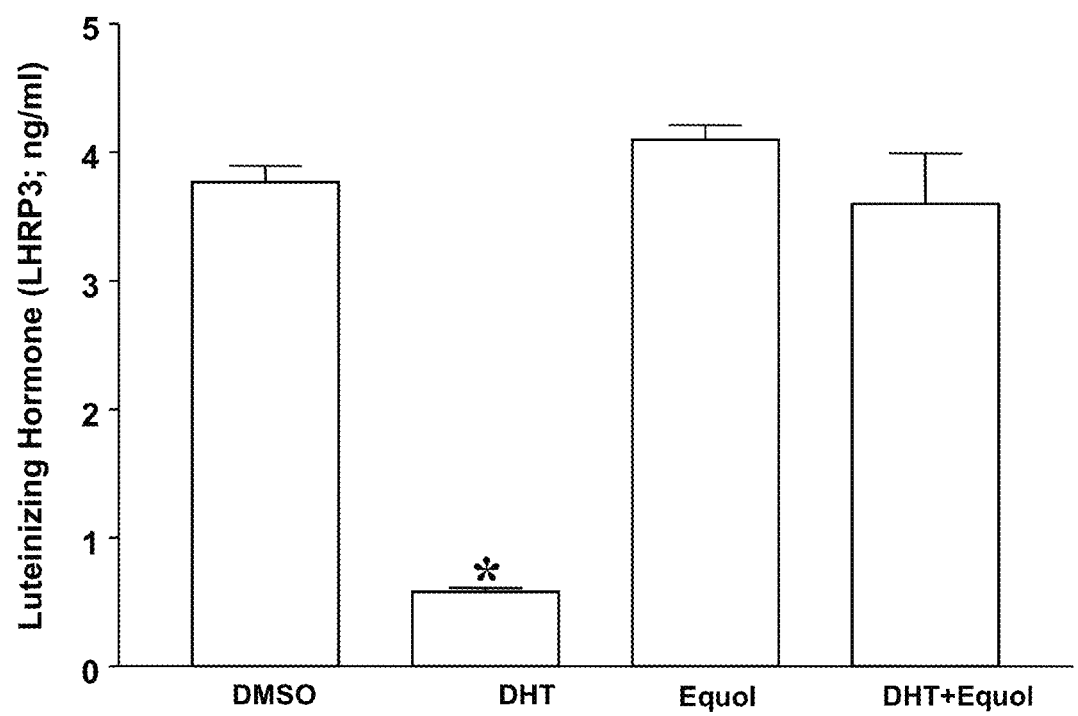
FIG. 10B shows plasma LH in gonadectomized (GDX) male rats sc injected with DMSO, DHT, equol, or both DHT and equol.

This example demonstrates that, in addition to modulating the effect of DHT on prostate size, equol binds to DHT in vivo and blocks the negative effects on LH secretion. GDX males treated with a long-lasting analog of DHT, DHT propionate (DHTP), show a significant increase in prostate weight compared to vehicle-treated GDX control rats. Concomitant treatment with equol (DHTP+equol) blocks the effects of DHTP, while equol has no effect alone on prostate size as shown in FIG. 10A. Equol also blocks DHT's negative feedback effects on LH. In GDX males LH is significantly decreased by DHTP treatment compared to treatment with DMSO. Treatment with equol in combination with DHT blocks the negative feedback effects of DHTP on LH secretion. Equol alone has no effect on LH levels, shown in FIG. 10B.

Example 6

Figure 11:
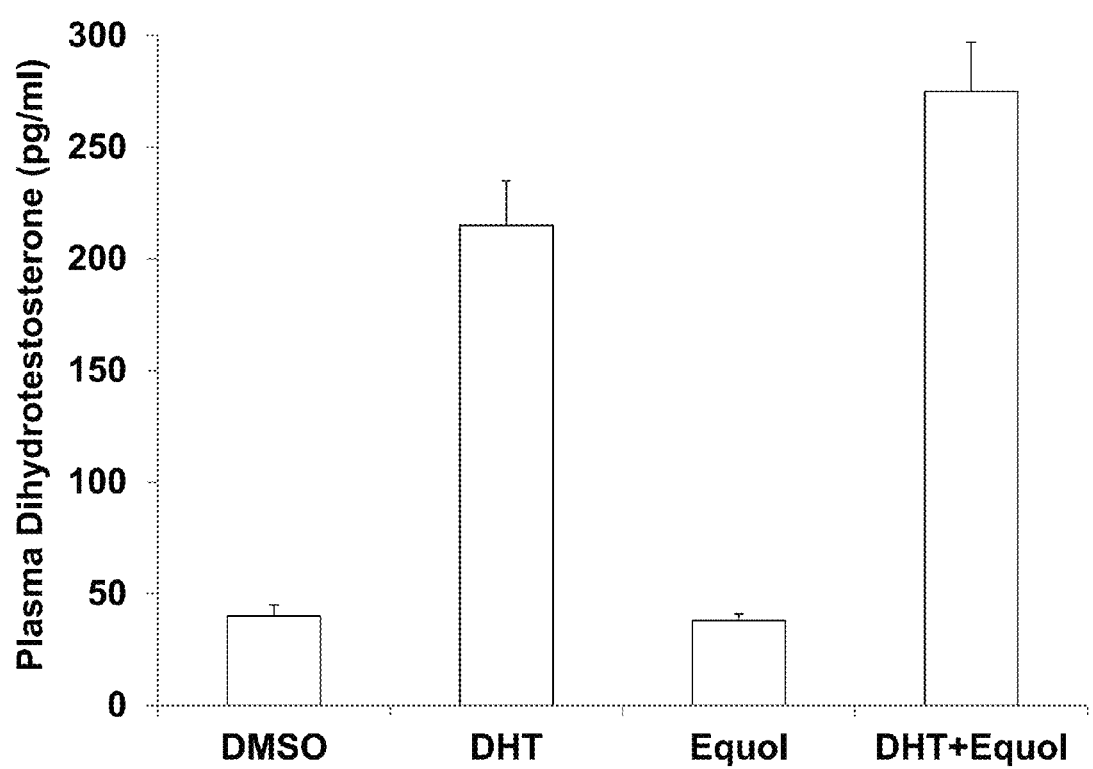
FIG. 11 shows plasma DHT levels in rats treated with DMSO, DHTP, equol, or both DHTP and equol.
Figure 12:
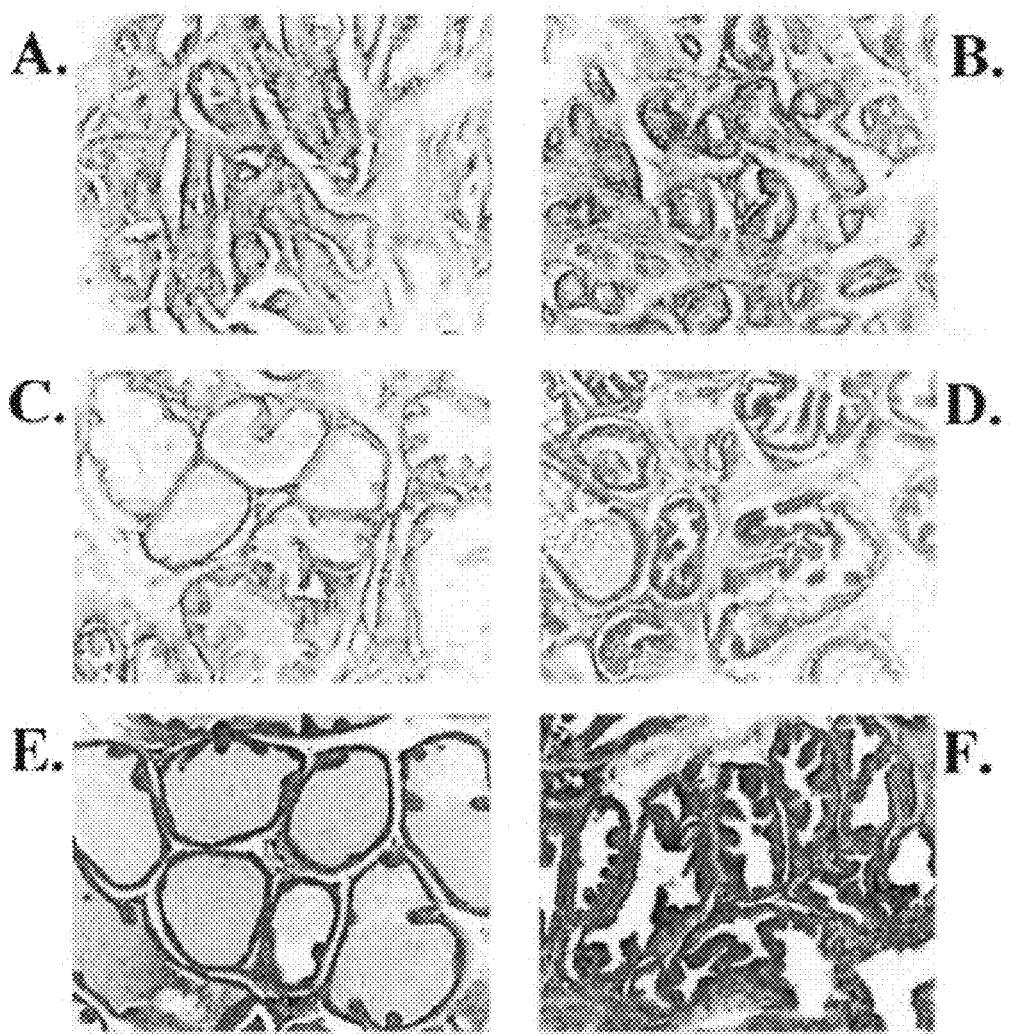
FIG. 12 shows the histological effects of equol in the prostate gland of GDX (A-D) and intact (E & F) rats treated with either Trent: DMSO (A & E), equol (B & F), DHT (C), or DHT plus equol (D).
Figure 13:
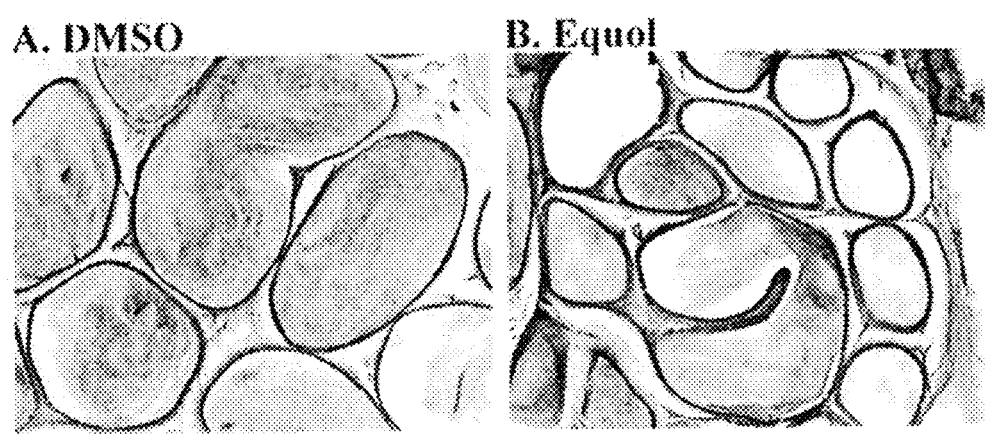
FIG. 13 shows the histological effects of equol on the epididymis of intact rats treated with DMSO (A) or equol (B).

This example demonstrates the effects of racemic equol on androgen-sensitive tissues. One week following arrival, animals are gonadectomized (GDX) under isoflurane anesthesia and allowed to recover for 7 days. Following recovery, animals are assigned to the following groups 1) DMSO, 2) DHTP (2 mg/kg), 3) racemic equol (0.25 mg/kg), or 4) both DHTP and racemic equol. Injections are given subcutaneously daily for 4 days. Animals are killed via decapitation and trunk blood and tissues are collected for analysis. Plasma DHT is measured, shown in FIG. 11. As expected there were significant elevations of plasma DHT in animals treated with DHTP (GDX+DHTP, GDX+equol+DHTP groups). Plasma DHT was further elevated, although, not significantly, by co-treatment with equol. Tissues, including prostate, testes and epididymis, are removed from the animal, dissected free of fat and connective tissues, weighed, fixed by immersion in 4% paraformaldehyde, and then sectioned at 15 µm on a cryostat. Tissue sections are mounted on charged slides (Superfrost Plus. Fisher Scientific, Pittsburgh, Pa.) prewarmed to 23° C., and stained with hematoxylin and eosin (H&E), dehydrated in ascending alcohol and cleared with xylene. Histological sections are shown in FIGS. 12 and 13. H&E stained prostates reflect a change due to both GDX and treatments. The prostate glands of control, equol, and DHTP plus equol treated groups show similar histology (FIG. 12 A, B, D). In these animals prostates are characterized by very small atrophic glands with little volume in the gland lumen. In DHTP-treated animals (FIG. 12 C), the glands show signs of cell proliferation. Lumen size is increased compared to GDX animals; the epithelium is of a tall columnar type (FIG. 12 C). In comparison to intact control animals (FIG. 12 E) the prostate of equol treated males show involution and consist of more closely spaced, atrophic glands (FIG. 12 F). In comparison to control males, the epididymal histology of equol-treated intact males shows overall smaller ducts, as evidenced by shrunken lumen (FIG. 13).

Example 7

Figure 14:
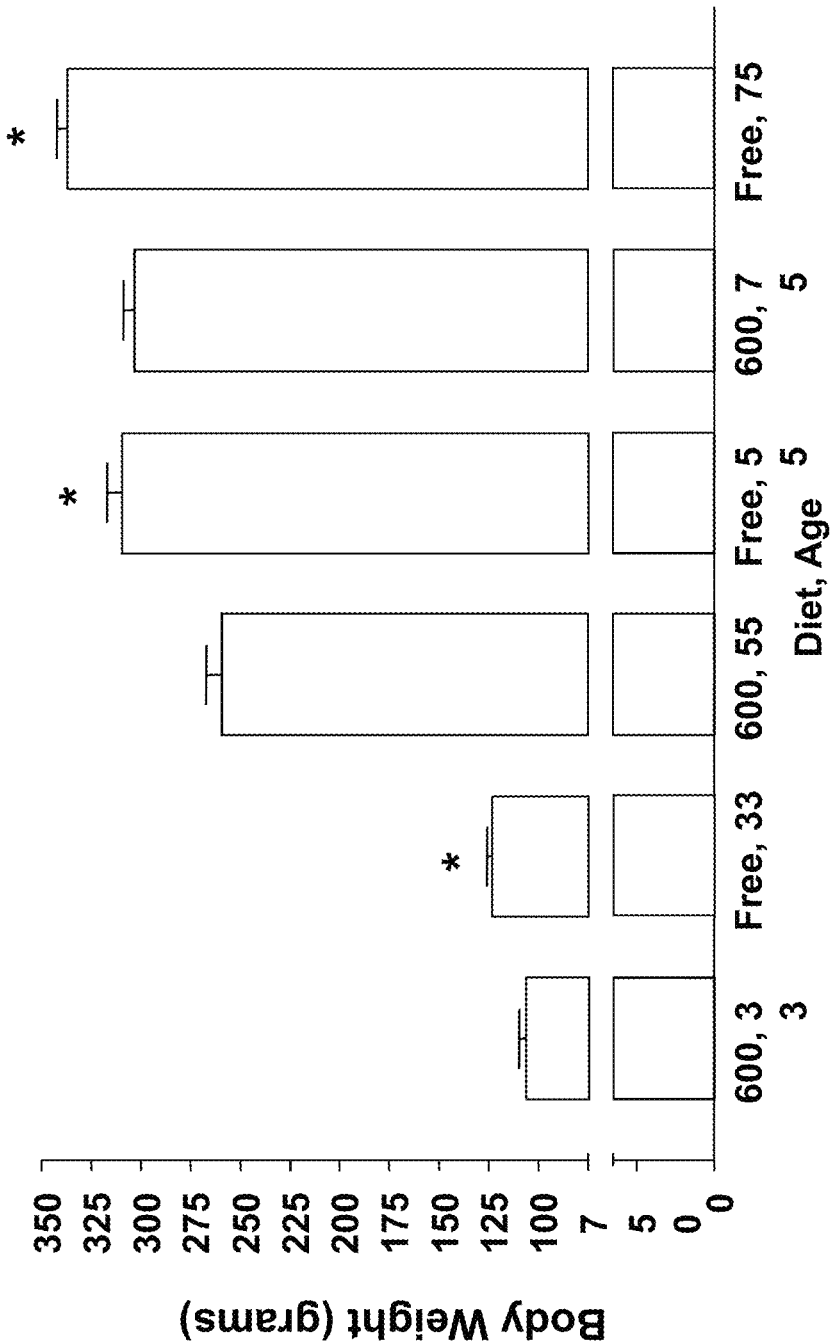
FIG. 14 shows body weight in male rats fed either an isoflavone-rich (Phyto-600) or a phytoestrogen-free (Phyto-Free) diet.
Figure 15:
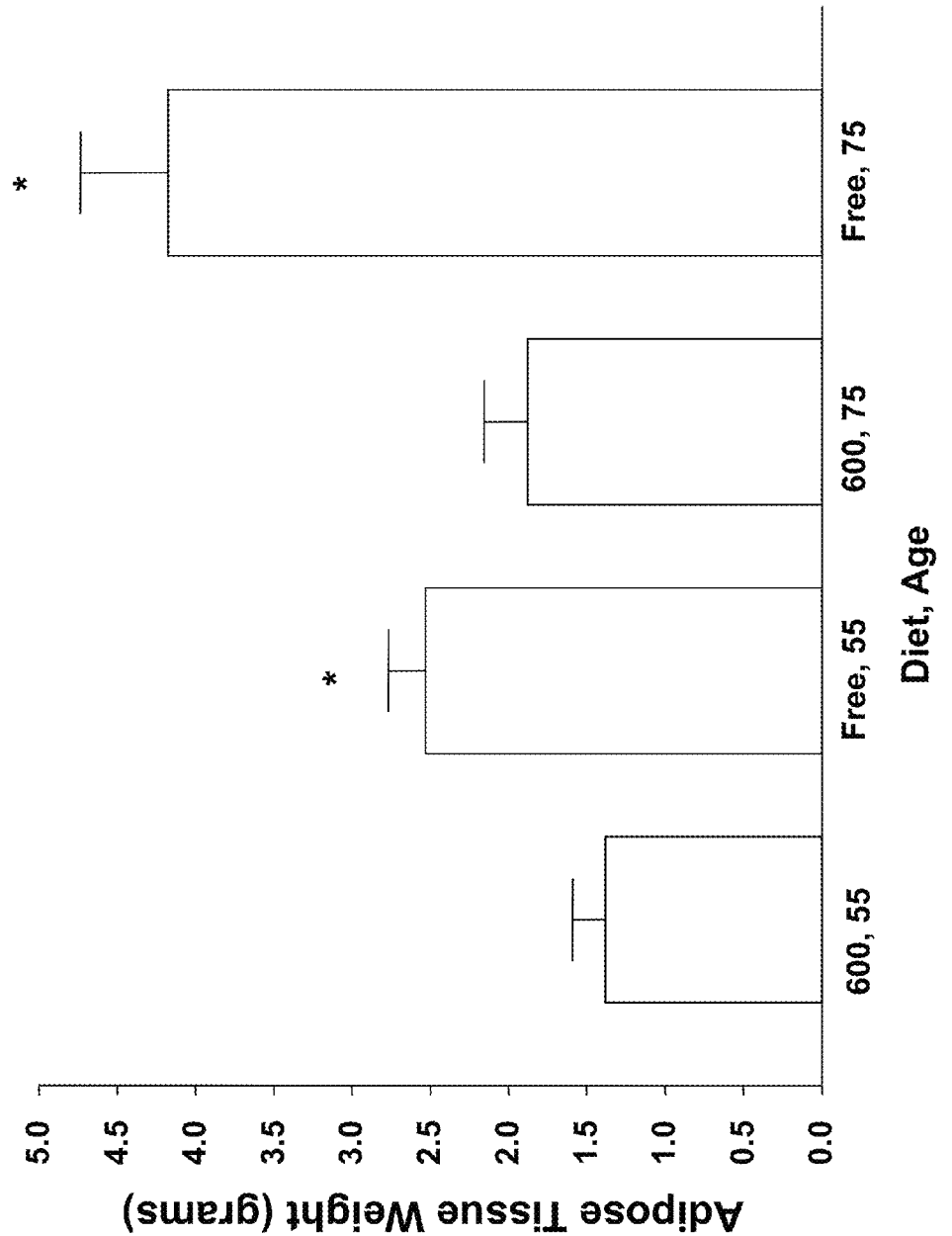
FIG. 15 shows the white adipose tissue mass in male rats fed either a Phyto-600 or Phyto-Free diet.

Long-Evans male rats are raised (life long from conception to time of sample collection) on either a phytoestrogen-rich diet containing 600 micrograms of isoflavones per gram of diet or 00) ppm of isoflavones (referred to hereafter as the "Phyto-600" diet) or a diet containing very low levels of isoflavones (referred to hereafter as the 'Phyto-Free' diet; containing approximately 10 ppm of isoflavones). As shown in FIG. 14 male Long-Evans rats fed the Phyto-600 diet display significantly lower body weights at 33, 55 or 75 days of age compared to animals fed the Phyto-Free diet. Adipose tissue (dissected from just below the kidneys to just above the testes in the abdominopelvic cavity) is measured in the 55 or 75 day-old males. At both ages, white adipose tissue mass is significantly greater in the Phyto-Free-fed males compared to Phyto-600-fed animals, FIG. 15. It should be noted that the reductions in body weight of Phyto-600-fed males are modest, at approximately 10 to 15% percent, whereas, the reductions in white adipose tissue from the same animals are approximately 50-60% compared to Phyto-Free-fed males. This greater reduction in white adipose tissue compared to body weight in soy fed animals is also a general characteristic seen in humans consuming soy-based diets (D. B. Allison et al, Eur J Clin Nutr, 2003, 57: 514-522. This particular result is repeatedly seen throughout the various experiments present in these data sets, regardless of age, sex, rat strain or whether female rats have their ovaries removed (simulating the post-menopausal condition in humans).

When food and water intake is measured to determine whether these parameters might influence body and adipose tissue weights, Phyto-600-fed males display slight but significantly higher food FIG. 16A) and water (FIG. 16B) intakes compared to Phyto-Free-fed animals. Thus, the reductions in body and adipose tissue weights cannot be explained by alterations in food/water intake between the diet treatments.

Figure 17A:
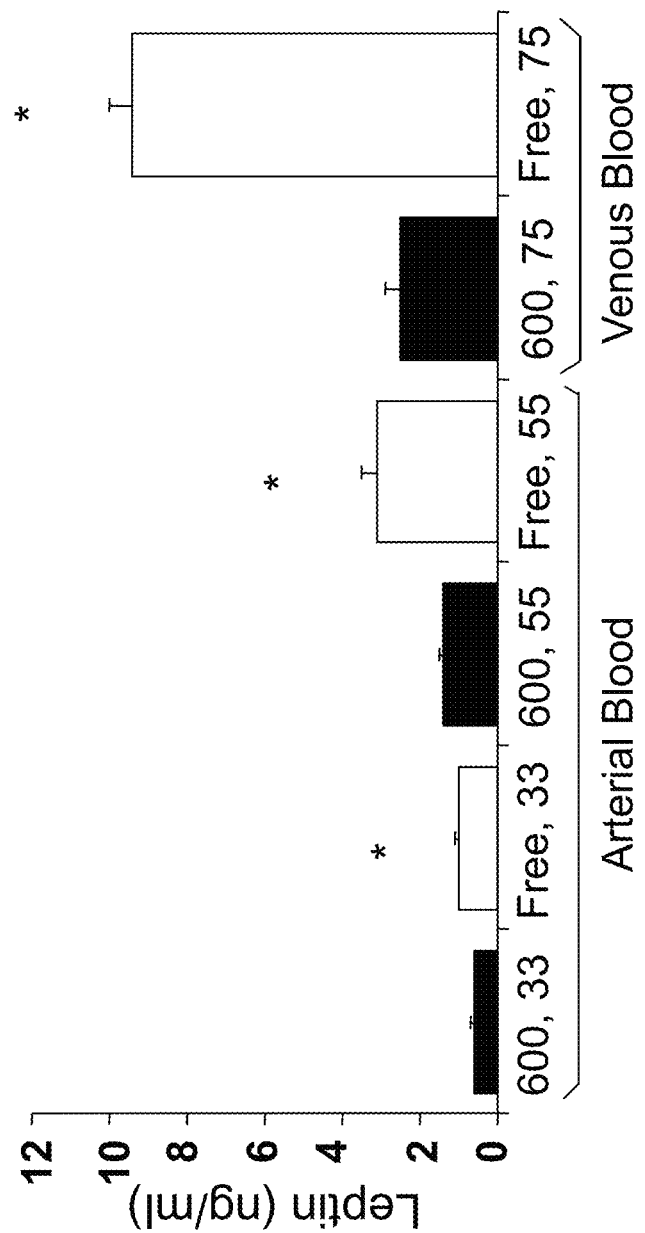

Since leptin is produced by adipose tissue (D. A. Sandoval et al., J Diabetes Complications, 2003, 17:108-113), serum leptin levels are measured, along with insulin levels, to determine the alterations in these metabolic hormones. As shown in FIG. 17A, leptin levels at 33, 55 or 75 days of age are significantly decreased in Phyto-600-fed males (which corresponds with the reductions seen in adipose tissue weights from these same animals) compared to Phyto-Free-fed males. Also, insulin levels are significantly decreased in Phyto-600-fed male vs. Phyto-Free-fed males (FIG. 17B), consistent with the benefits of protecting against insulin resistance associated with type-2 diabetes (V. Jayagopal et al., Diabetes Care, 2002, 25:1709-1714).

To demonstrate that circulating isoflavone levels are different in Phyto-600-vs. Phyto-Free-fed male and female (75 day-old) rats, serum isoflavone levels are determined by GC/MS as previously performed by our laboratories (see methods in K. D. R. Setchell, Am J Clin Nutr 129:1333S-1346S, 1998; and K. D. R. Setchell et al, J Nutr 132:3577-3584, 2002). In each case for the different classifications of isoflavones Phyto-600-fed males display significantly higher isoflavone levels compared to Phyto-Free-fed values, shown in Table 4. More importantly, equol levels in the Phyto-600-fed rats account for approximately 78% of the total phytoestrogen levels.

TABLE 4

Isoflavone concentrations in adult male and female rats

|  | Genistein | Daidzein | Equol | Total (ng/ml) |
|---|---|---|---|---|
| Males: | | | | |
| Very Low Isoflavone Diet | 9.6 ± 0.3 | 10.8 ± 0.6 | 23.2 ± 0.4 | 43.5 ± 1.0 |
| High Isoflavone Diet | 413 ± 67 | 394 ± 58 | 1,161 ± 325 | 1,967 ± 45 |
| Females: | | | | |
| Very Low Isoflavone Diet | 3.9 ± 0.2 | 5.3 ± 0.8 | 21.6 ± 1.2 | 30.8 ± 2.2 |
| High Isoflavone Diet | 99 ± 9 | 117 ± 7.4 | 931 ± 21 | 1,147 ± 5 |

Figure 18:
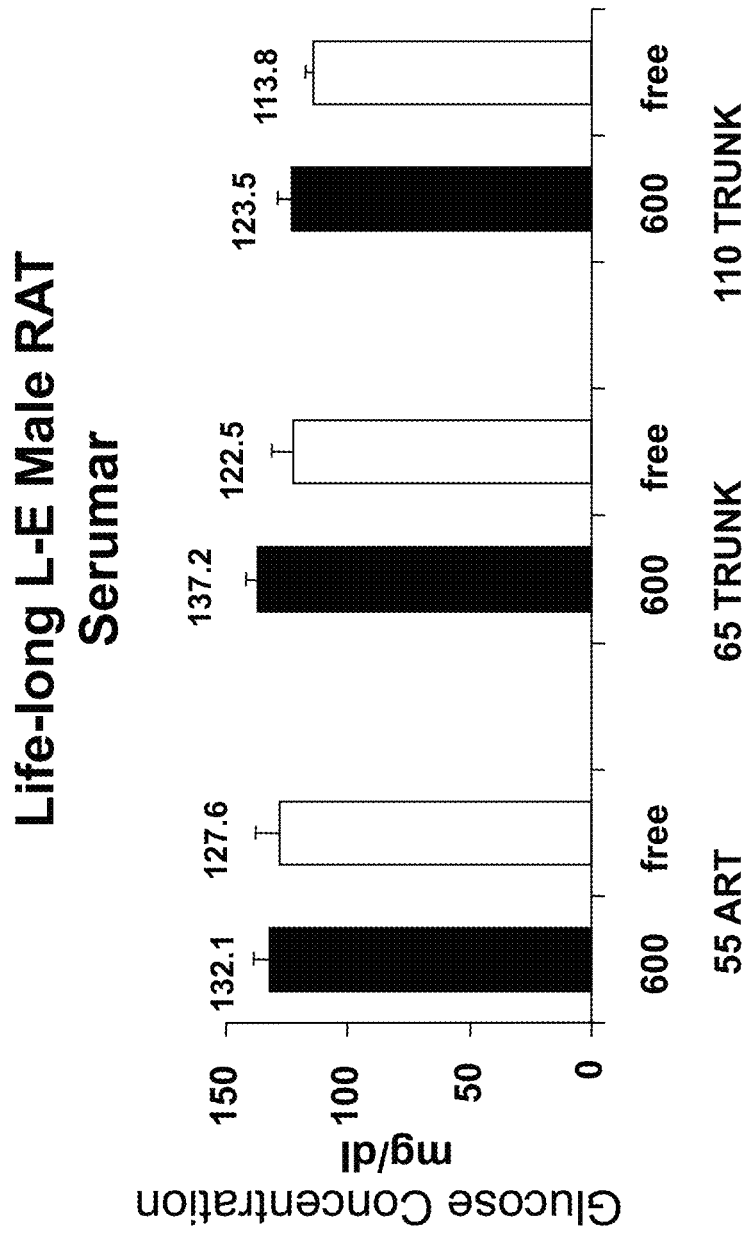
FIG. 18 shows serum glucose levels from male rats (non-fasting) fed either a Phyto-600 or Phyto-Free diet.
Figure 19:
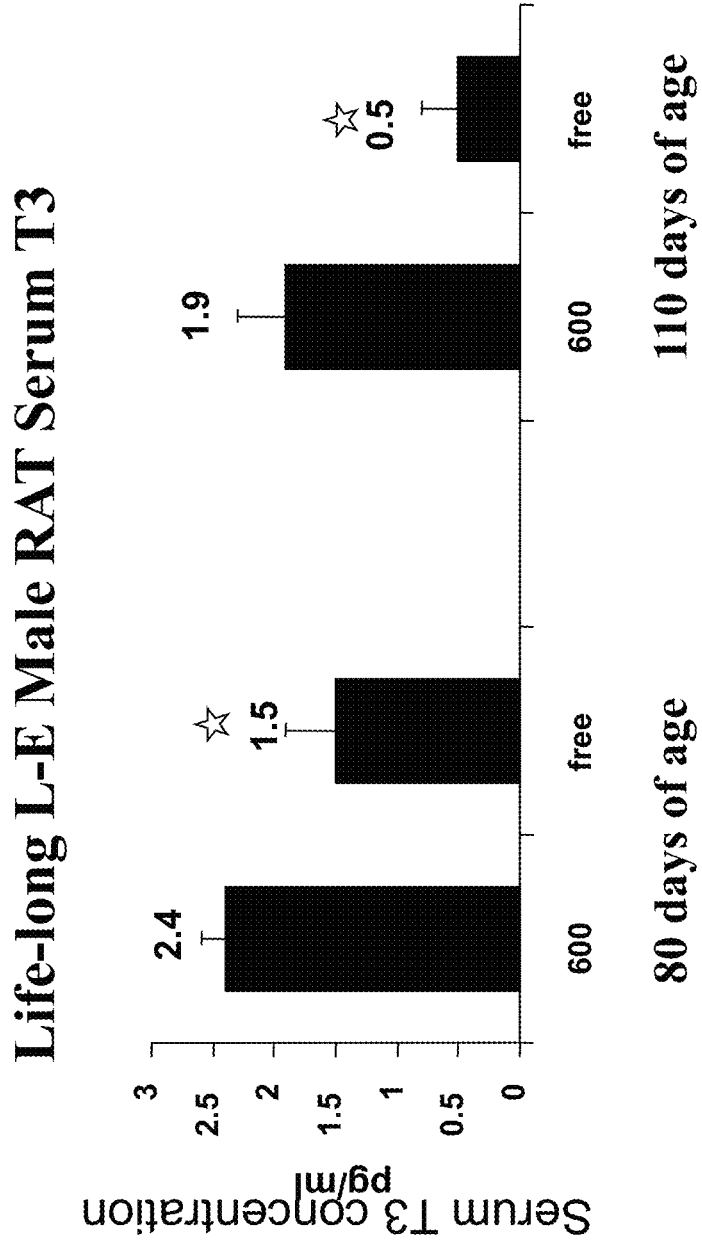
FIG. 19 shows thyroid (T3) serum levels in male rats fed either a Phyto-600 or Phyto-Free diet.

To determine if other metabolic hormones were altered by the diet treatments or by age, serum glucose and thyroid (T3) levels are assayed. Glucose levels are slightly (but not significantly) higher in the Phyto-600-fed males compared to Phyto-Free-fed values, independent of age or source of the blood samples [either arterial (ART) or venous (TRUNK)], shown in FIG. 18. However, when T3 levels are quantified, there is a significant increase in T3 serum levels in 80 or 110 day-old male Long-Evans rats fed the Phyto-600 diet compared to Phyto-Free-fed animals, shown in FIG. 19. This suggests that thyroid levels are enhanced with soy consumption consistent with anecdotal evidence of individuals that decreased their thyroid medication or went off of thyroid treatment completely with the consumption of soy based foods in their diets. This is also consistent with reports of a similar increase in T3 levels in humans following consumption of soy foods (Watanabe, S. et al, Biofactors 2000: 12(1-4):233-41).

Example 8

Figure 20:
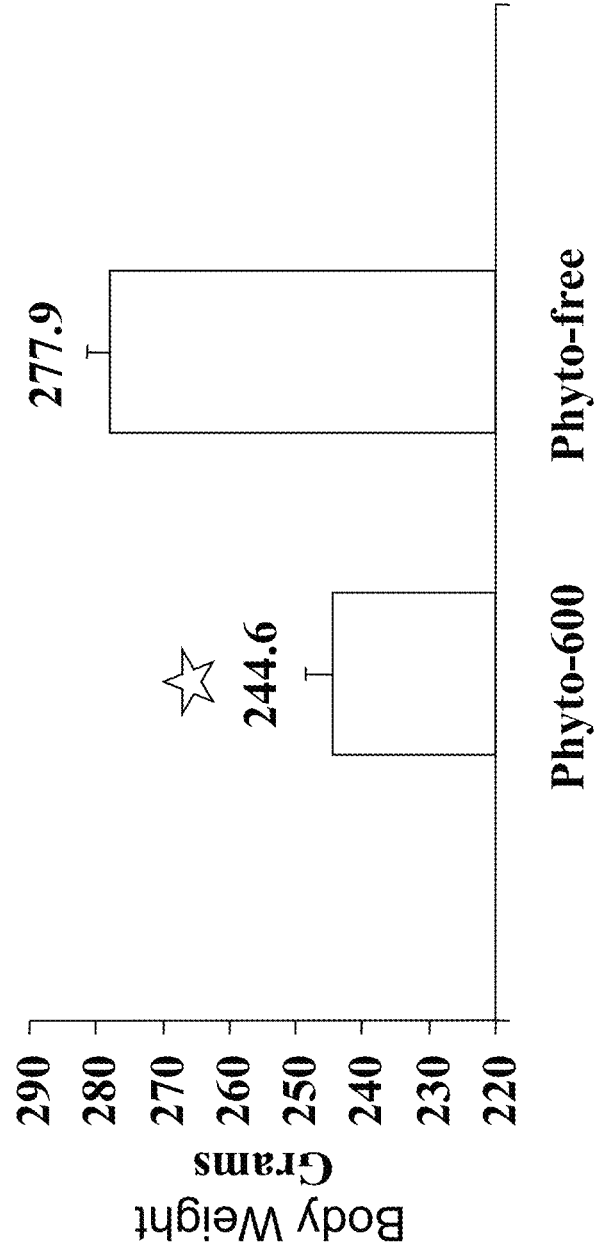
FIG. 20 shows body weights of female rats fed either a Phyto-600 or Phyto-Free diet.
Figure 21:
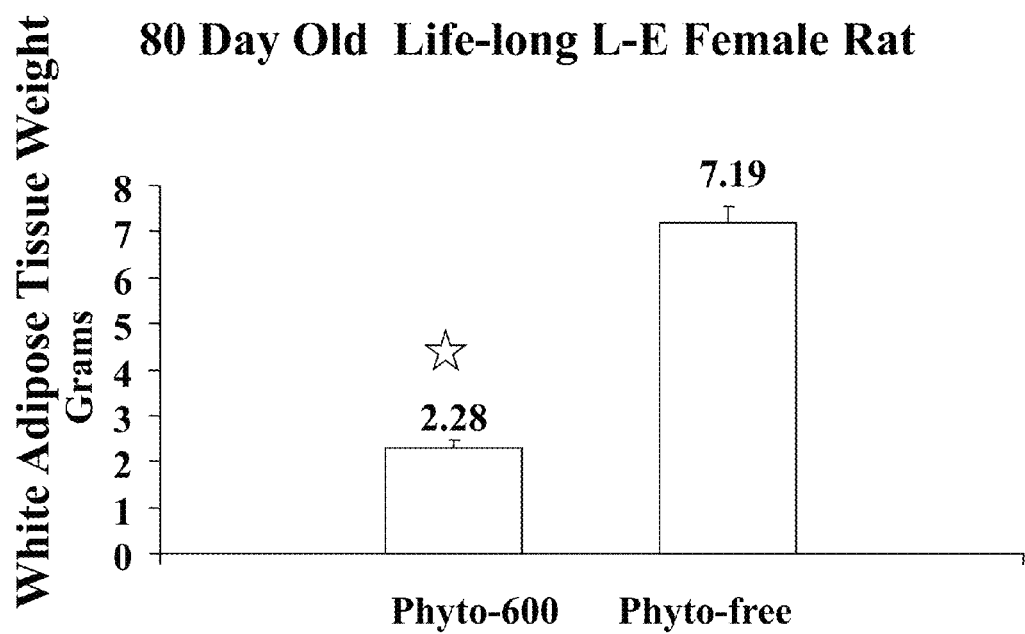
FIG. 21 shows the white adipose tissue mass from female rats fed either a Phyto-600 or a Phyto-Free diet.

In this experiment, female Long-Evans rats are raised (life long from conception to time of sample collection) on either Phyto-600 or Phyto-Free diets. As shown in FIG. 20, rats fed the Phyto-600 diet display significantly lower body weights at 80 days of age compared to animals fed the Phyto-Free diet, representing about a 12% reduction in body weight in the Phyto-600-fed animals. As seen in the male Long-Evans Phyto-600-fed rats previously, females fed the Phyto-600 diet also displayed significant reductions in adipose tissue weight (by about 68%) compared to females fed the Phyto-Free diet, shown in FIG. 21.

Figure 22:
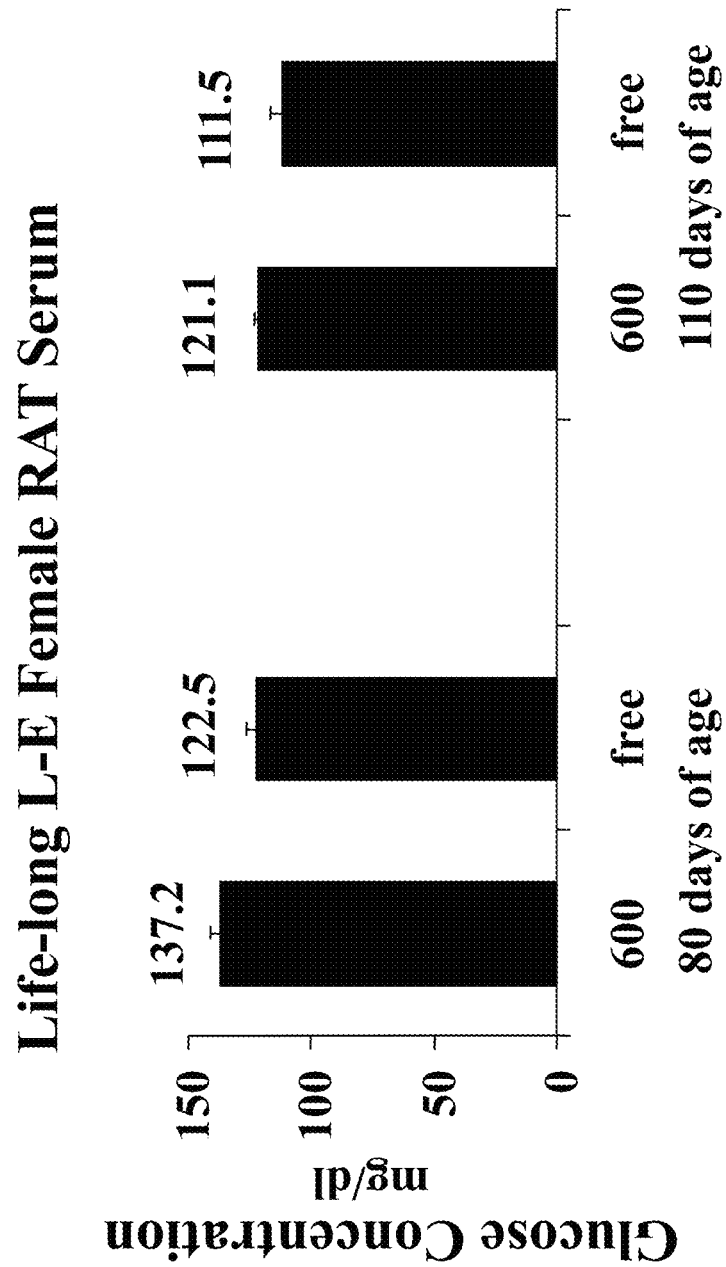
FIG. 22 shows serum glucose levels from female rats fed either a Phyto-600 or Phyto-Free diet.
Figure 23:
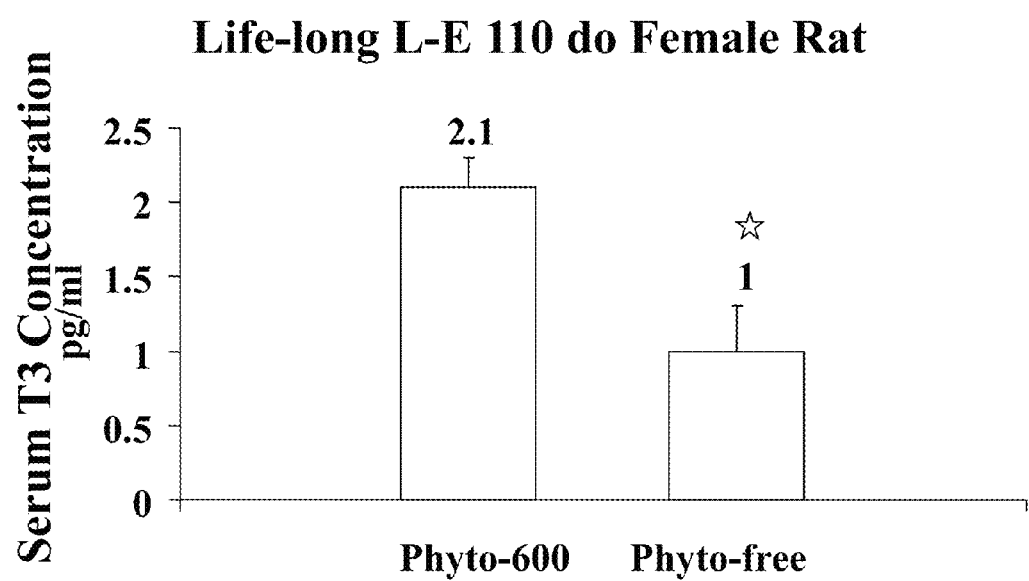
FIG. 23 shows serum T3 levels from female rats fed either a Phyto-600 or Phyto-Free diet.

Similar to results with male rats, serum glucose levels are slightly but not significantly higher in Phyto-600-fed female rats at 80 or 110 days of age compared to animals in the Phyto-Free diet treatment group, shown in FIG. 22. However, T3 levels are significantly higher in females fed the Phyto-Phyto-600 diet compared to Phyto-Phyto-Free fed animals at 110 days of age, shown in FIG. 23. The T3 and glucose results in females are very similar to those obtained in male rats exposed to the same diet treatments, and thus, suggest similar health benefits for both genders. Samples collected at 100 days of age yield similar results (i.e., significant reductions in body weight and adipose tissue weights with the consumption of the Phyto-600 diet vs. the Phyto-Free diet) in female Long-Evans rats (data not shown).

Example 9

Figure 24:
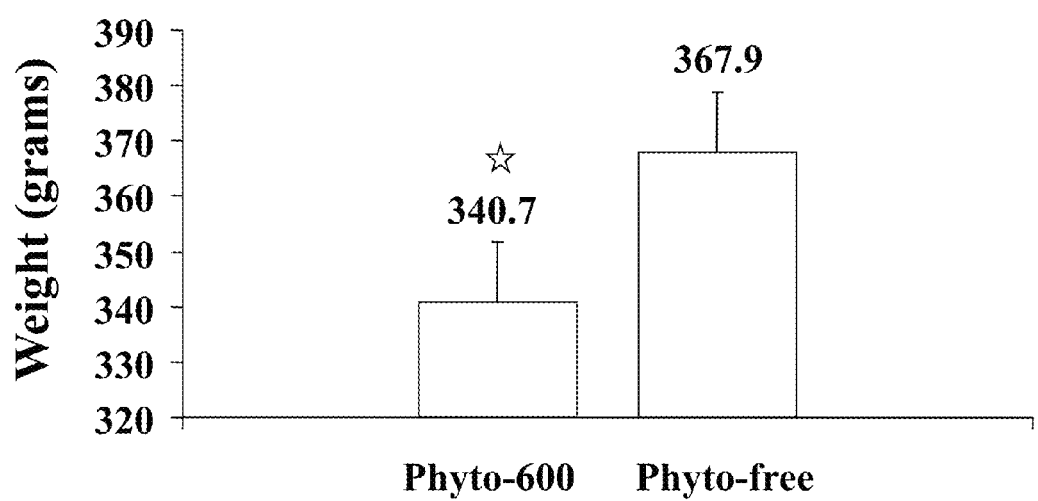
FIG. 24 shows the body weights of female rats fed either a Phyto-60) or a Phyto-Free diet after 50 days of age.
Figure 25:
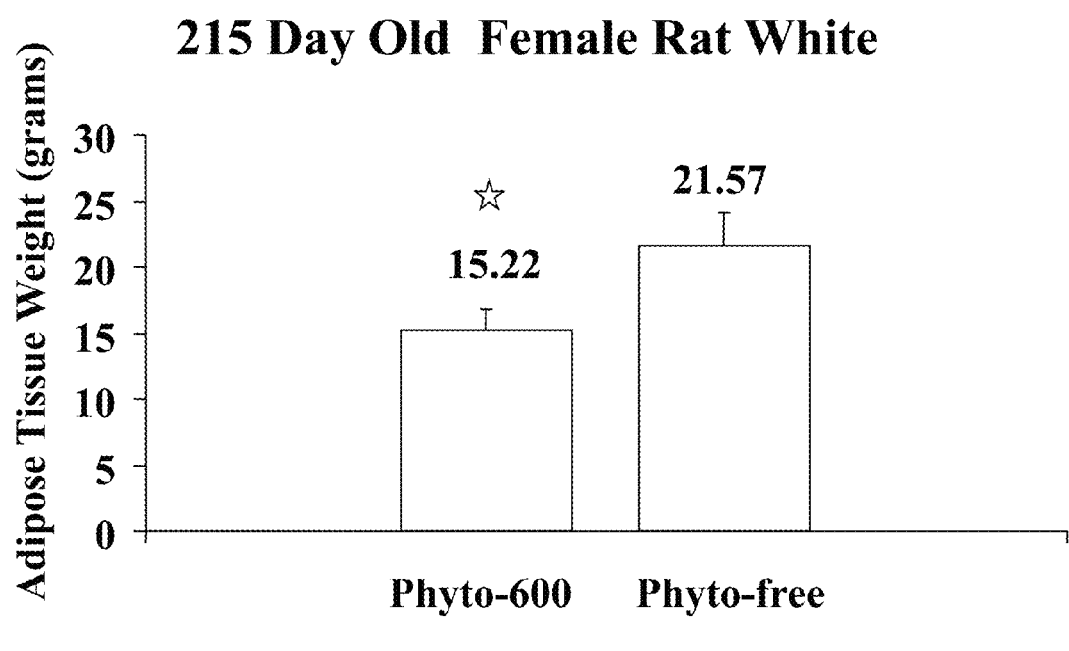
FIG. 25 shows the white adipose tissue mass of female rats fed either a Phyto-600 or a Phyto-Free diet after 50 days of age.
Figure 26:
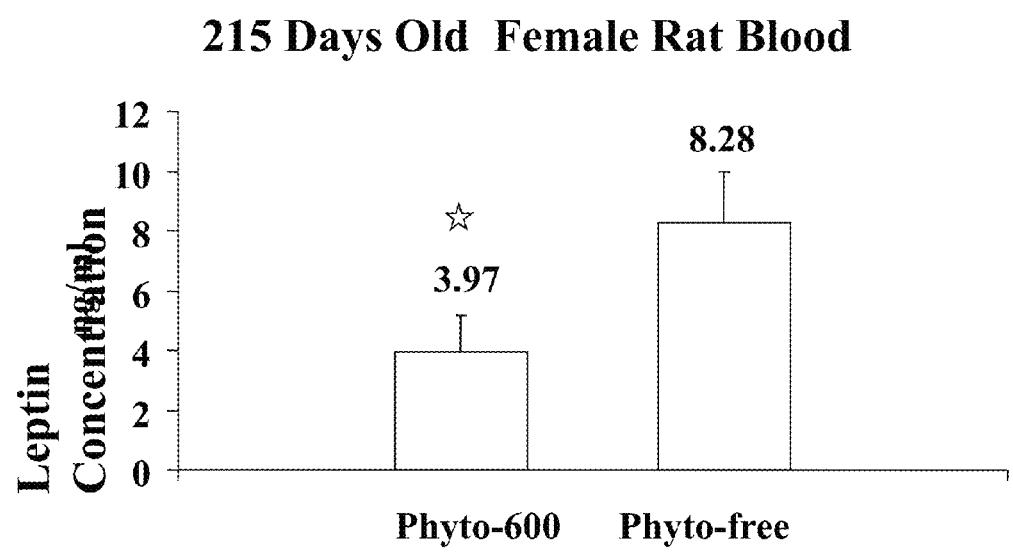
FIG. 26 shows the serum leptin levels of female rats fed either a Phyto-600 or a Phyto-Free diet after 50 days of age.
Figure 27:
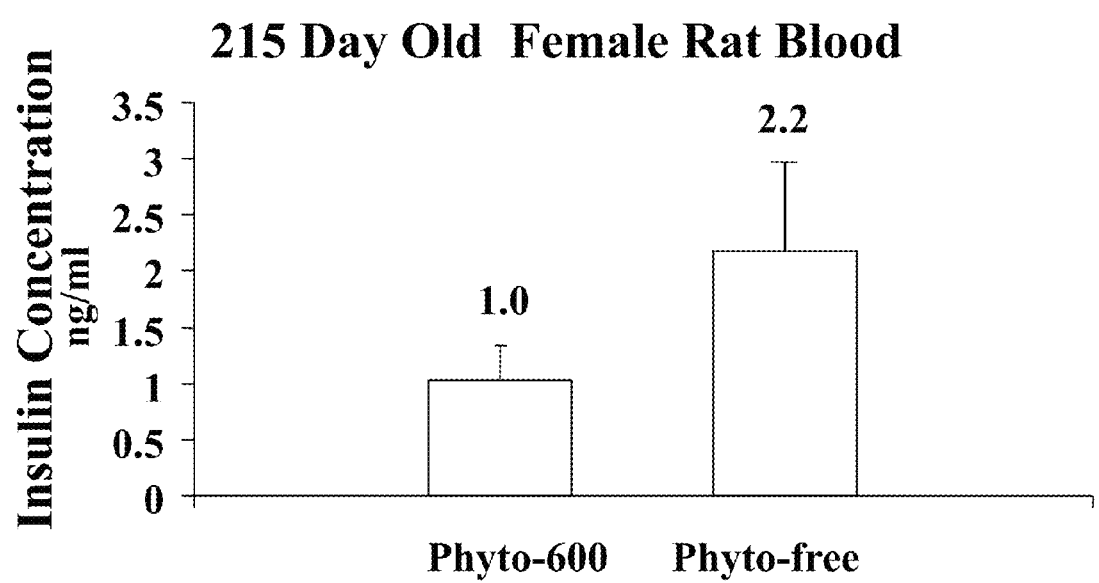
FIG. 27 shows the serum insulin levels of female rats fed either a Phyto-600 or a Phyto-Free diet after 50 days of age.

Adult female rats are placed on the Phyto-600 or Phyto-Free diet treatments from 50 to 215 days of age. Prior to 50 days of age the animals can be raised on a diet that contains approximately Phyto-200 ppm of isoflavones, or similar a diet such as those used by animal suppliers. At 215 days of age. Phyto-600-fed females weigh significantly less than Phyto-Free-fed females, representing about a 7% reduction in body weight, shown in FIG. 24. White adipose tissue in Phyto-600-fed females at 215 days of age is significantly reduced by about 30% compared to that of females fed the Phyto-Free diet, shown in FIG. 25. Correspondingly, serum leptin levels in the Phyto-600-fed females were significantly lower than those of Phyto-Free-fed, shown in FIG. 26. Insulin levels were reduced in the Phyto-600-fed vs. Phyto-Free-fed females to a similar degree seen previously, but did not reach statistical significance, shown in FIG. 27.

Example 10

Figure 28:
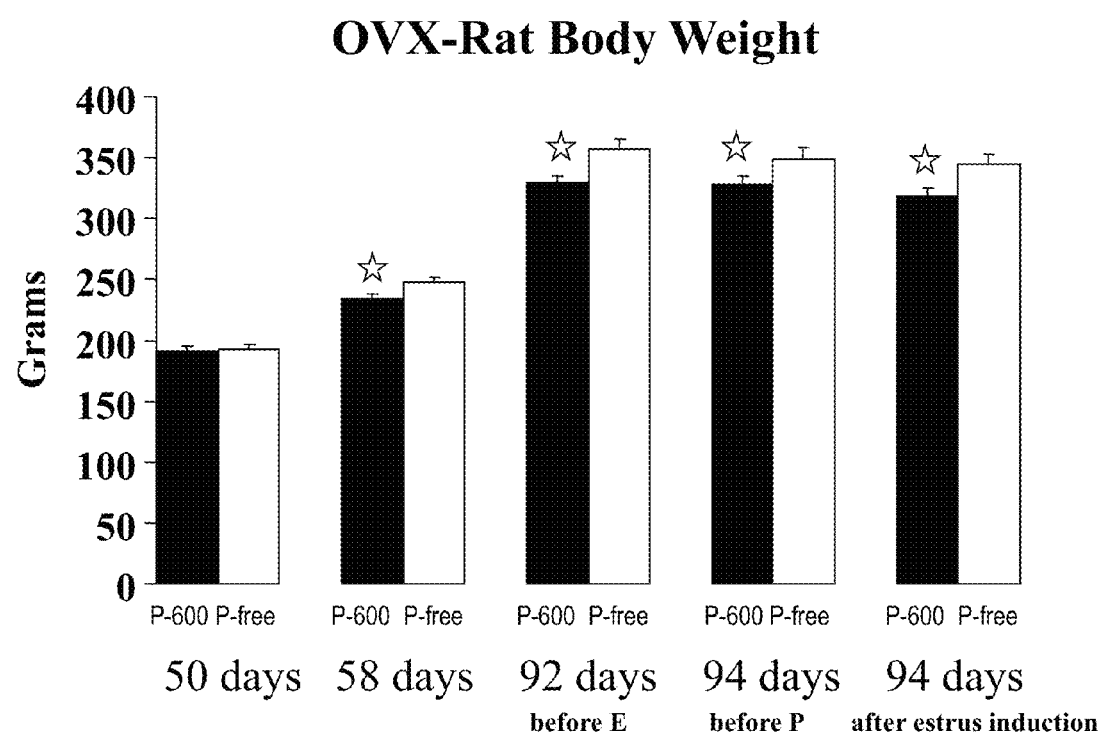
FIG. 28 shows body weights of OVX rats fed either a Phyto-600 (black bars) or a Phyto-Free (white bars) diet after and placed on a behavioral estrus induction regimen.

This example demonstrates the effects of a Phyto-600 or Phyto-Free diet on adult ovariectomized (OVX) rats. The OVX rat is a well-established animal model of postmenopausal human females. In addition, OVX permits the subcutaneous injections of estrogen and progesterone to stimulate behavioral estrus in rats, to determine the effects of a Phyto-600 or Phyto-Free diet. Adult ovariectomized rats are fed a phytoestrogen diet of approximately 200 ppm of isoflavones ("Phyto-200") until 50 days of age (all animals are ovariectomized at approximately 40 days of age). The female rats are age and weight matched at 50 days of age and placed into one of two diet treatments: either the Phyto-600 (black bars) or Phyto-Free (white bars) until 94 days of age. Baseline body weights are taken at 50 days of age before the animals are placed on the diet treatments, again at 58 days (8 days of diet treatment), at 92 days of age (before injection of estradiol), and at 94 days of age (before injection of progesterone, and 6 hours later at 94 days of age (after chemical induction of behavioral estrus), shown in FIG. 28.

After consuming the diets for 8 days, the Phyto-600-fed rats display a slight but significant reduction in body weight (of about 7%) compared to Phyto-Free-fed. This reduction in body weight is maintained before and during the chemical induction of behavioral estrus by the estrogen and progesterone (steroid) injections.

Figure 29:
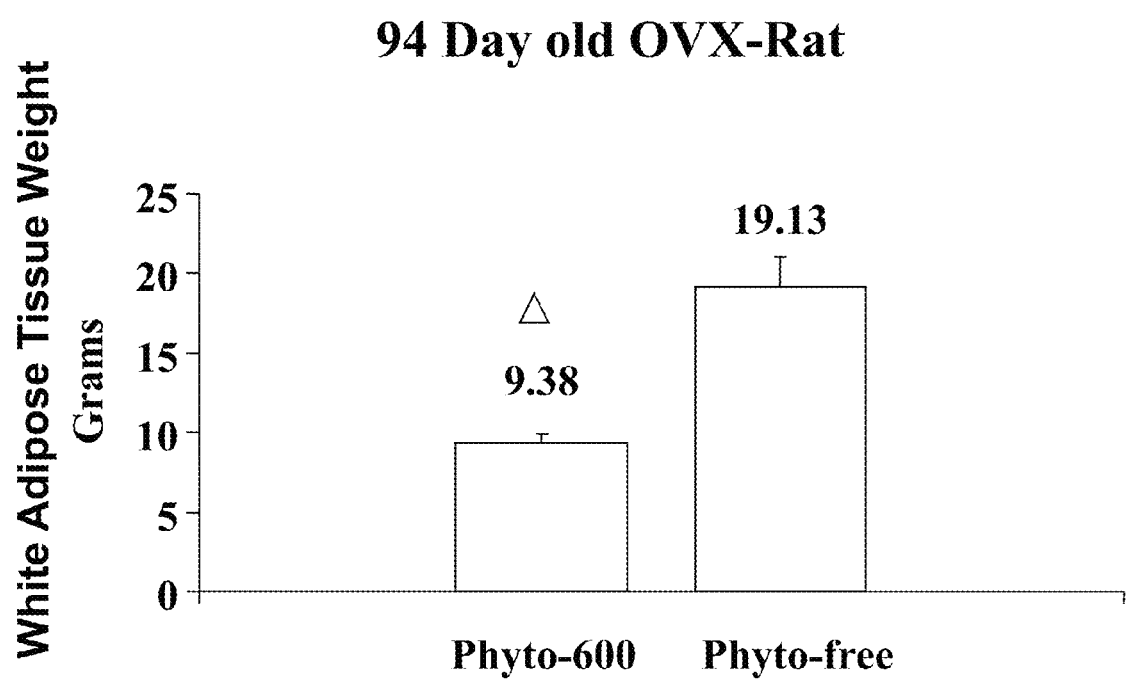
FIG. 29 shows the white adipose tissue mass of OVX rats fed either a Phyto-600 or a Phyto-Free diet.

White adipose tissue is measured at 94 days of age after the chemical induction of behavioral estrus, Phyto-600-fed OVX rats have approximately 50% less white adipose tissue mass compared to Phyto-Free-fed OVX rats, shown in FIG. 29, consistent with findings in Examples 9 and 10.

Figure 30:
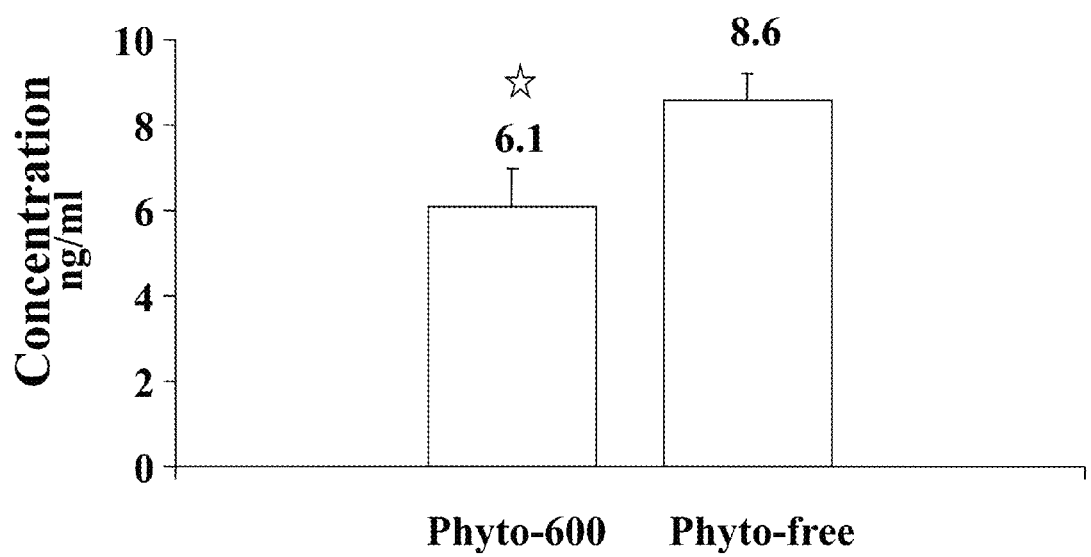
FIG. 30 shows the serum leptin levels of OVX rats fed either a Phyto-600 or a Phyto-Free diet.

Serum leptin levels in Phyto-600-fed OVX rats are decreased by approximately 30% compared to Phyto-Free-fed rats, shown in FIG. 30, reflecting the decreased white adipose tissue mass.

Example 11

Male and female Long-Evans rats are purchased from a supplier at 50 days of age. All animals are raised (from conception to 50 days of age) on the Phyto-200 diet. At 50 days old the male and female rats are randomly assigned to one of four diet treatment groups: 1) AIN-76 diet containing approximately <5 ppm isoflavones, 2) the Phyto-Free, 3) Phyto-200, or 4) Phyto-600 diet, described in previous examples. The AIN-76 diet contains extremely low concentrations of isoflavones, its formulation is quite different compared to the other three diets. For example, the sucrose content is very high (almost approaching 50% of the total diet formulation) and has a dense white consistency that the rats may not enjoy consuming as much as the regular plant-based ingredient diets (i.e., the Phyto-Free diet uses corn and wheat in its formulation which contains very low levels of isoflavones); the Phyto-200 or Phyto-600 diets use varying amount of soy meal in their formulations. The male rats are maintained on their assigned diets until 350 days of age (equivalent to middle-age in humans). The female rats are maintained on the diets until 279 days of age (approaching middle-age in humans). Food and water intake is measured to determine the potential influence of these parameters on body weight changes. In each case these factors do not contribute to the reductions in body weight with consumption of the isoflavone-containing diets (i.e., Phyto-200 and Phyto-600 diets; data not shown).

Males—

Figure 31:
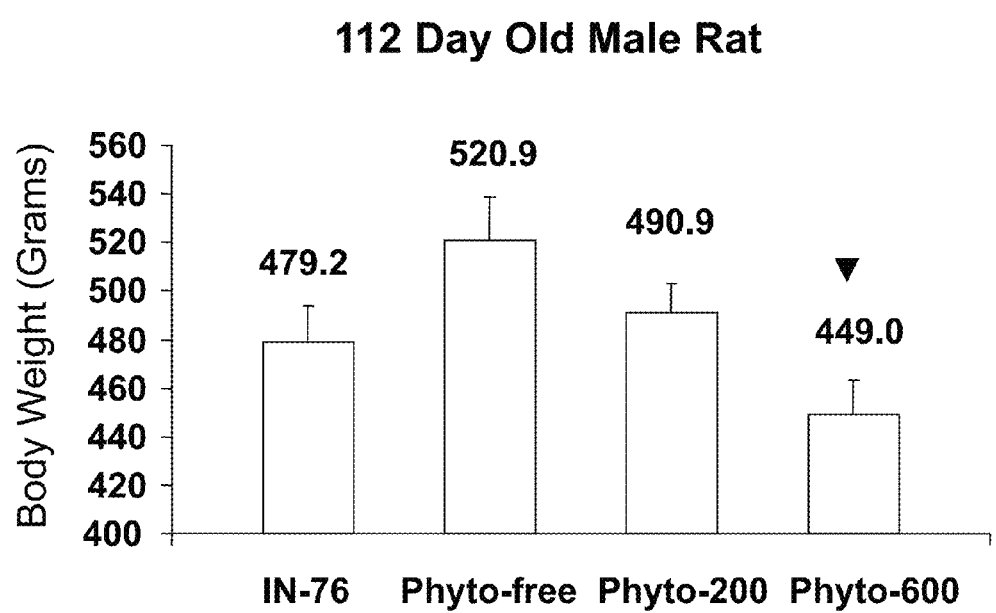
FIG. 31 shows the body weights of 112-day-old male rats fed AIN-76, Phyto-Free, Phyto-200, or Phyto-600 diets.

At 112 days of age (on the diets for approximately 62 days), body weights are recorded, shown in FIG. 31. The males fed the Phyto-Free diet have the heaviest body weights and the Phyto-600-fed males have the lowest, while the males on the AIN-76 and the Phyto-200 diets fall in between these two group values. The Phyto-600-fed body weights are significantly lower, by approximately 14%, than the Phyto-Free-fed males.

Figure 32:
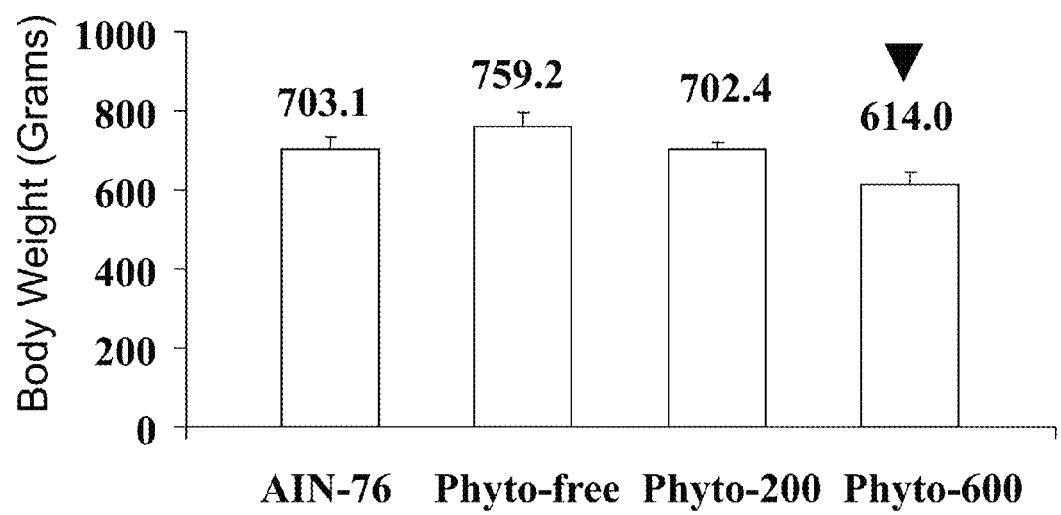
FIG. 32 shows the body weights of 279-day-old male rats fed AIN-76, Phyto-Free, Phyto-200, or Phyto-600 diets.
Figure 33:
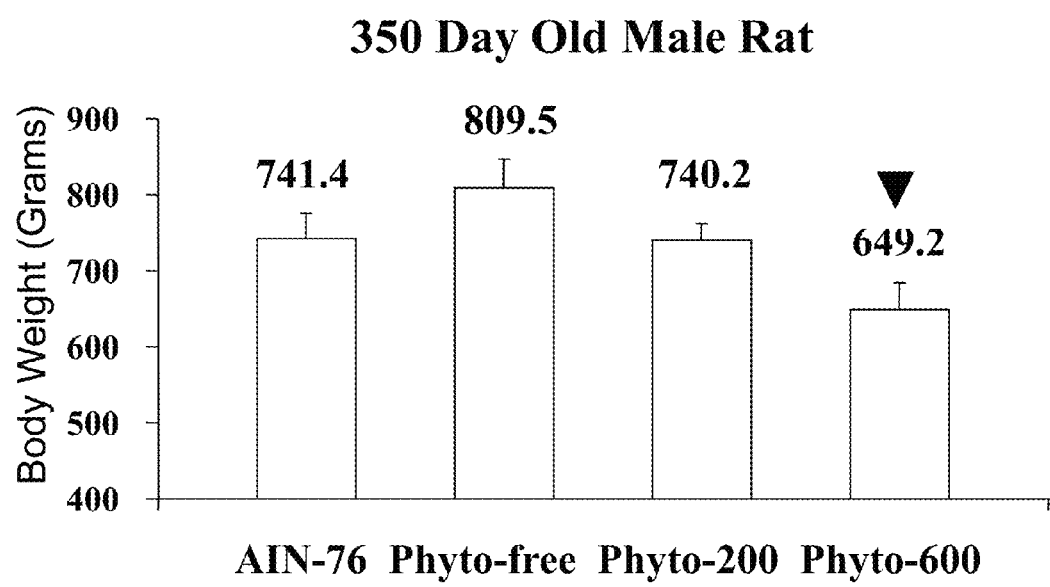
FIG. 33 shows the body weights of 350-day-old male rats fed AIN-76, Phyto-Free, Phyto-200, or Phyto-600 diets.

Correspondingly, at 279 and 350 days of age the male rats have a similar profile to that observed at 112 days of age, shown in FIGS. 32 and 33, respectively. The males fed the Phyto-Free diet display the heaviest body weights and the Phyto-600-fed males display the lowest body weights, while the males on the AIN-76 and Phyto-200 diets fall in between these two group values.

Figure 34:
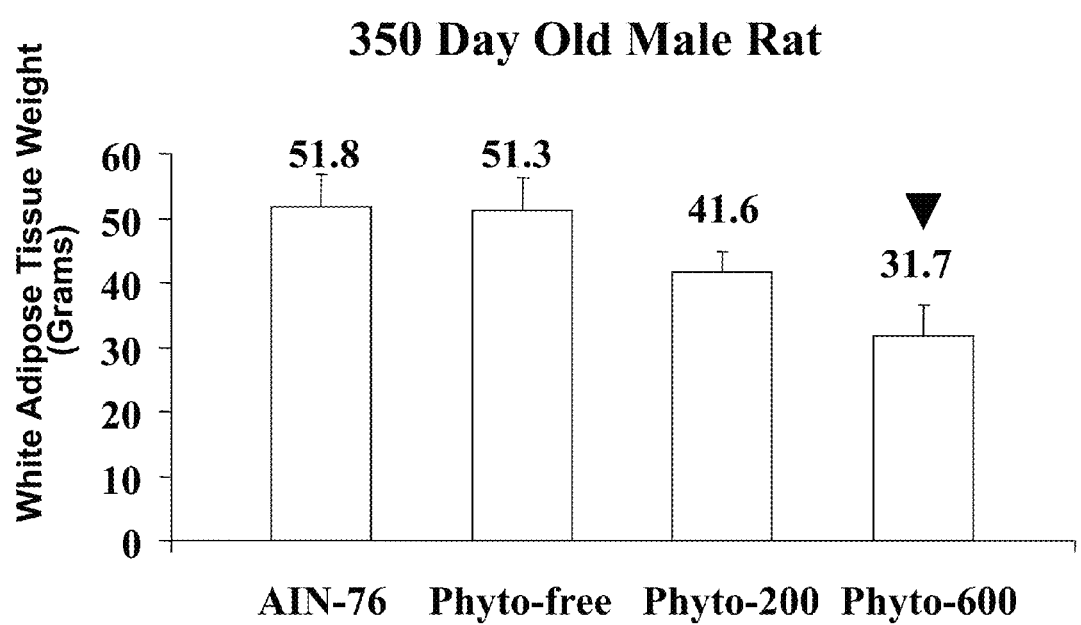
FIG. 34 shows the adipose tissue mass from 350-day-old male rats fed AIN-76, Phyto-Free, Phyto-200, or Phyto-60) diets.

Males fed the AIN-76 or the Phyto-Phyto-Free fed males display the highest white adipose tissue weights, measured at 350 days of age. The Phyto-200-fed males show a 19% non-significant reduction in white adipose tissue weight compared to AIN-76 or Phyto-Free-fed rats. Male rats fed the Phyto-600 diet have significantly less adipose tissue mass, an approximate 40% reduction, compared to AIN-76 or Phyto-Free-fed rats, shown in FIG. 34.

Figure 35:
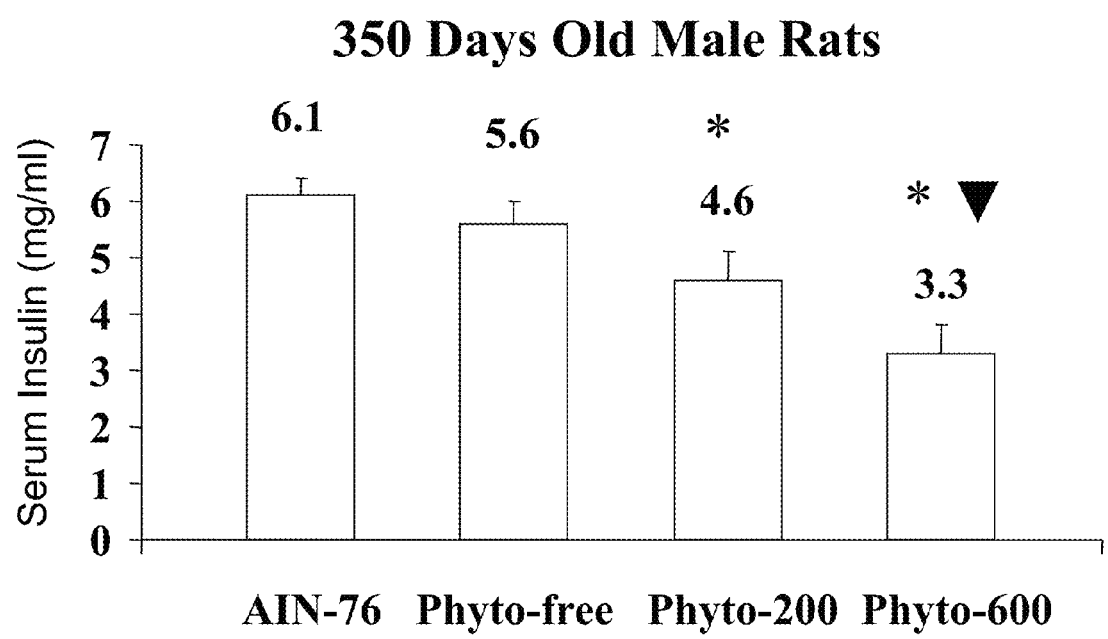
FIG. 35 shows serum insulin levels in 350-day-old male rats fed AIN-76, Phyto-Free, Phyto-200, or Phyto-600 diets.
Figure 36:
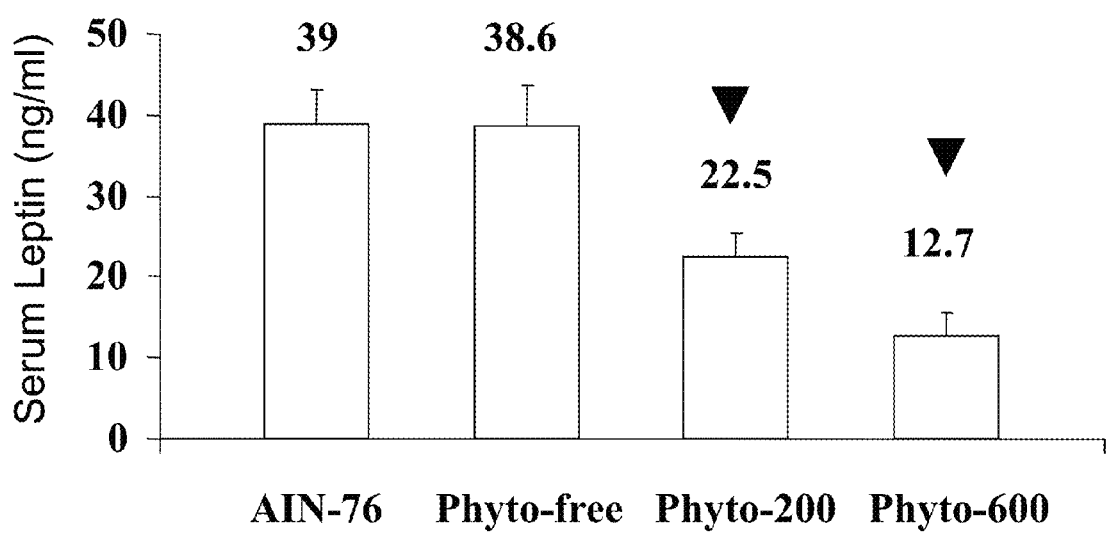
FIG. 36 shows serum leptin levels in 350-day-old male rats fed AIN-76, Phyto-Free, Phyto-200, or Phyto-600 diets.

Both serum insulin and leptin levels are significantly reduced as a function of increasing concentrations of isoflavones in the diet treatments, shown in FIGS. 35 and 36, respectively. For example, males fed the Phyto-200 or Phyto-600 diets have significant reductions in insulin levels compared to AIN-76 fed males. Also, Phyto-600-fed males show an approximate 50% reduction in insulin levels compared to Phyto-Free-fed male Serum leptin profiles display a similar pattern to that of the insulin results, where Phyto-200- or Phyto-600-fed males have significant reductions in serum insulin levels compared to either AIN-76 or Phyto-Free-fed males. Insulin levels in the Phyto-600-fed males are 46% lower compared to the Phyto-200-fed males. However, the difference between these two diet groups do not reach significance ($p<0.065$).

Females—

Figure 37:
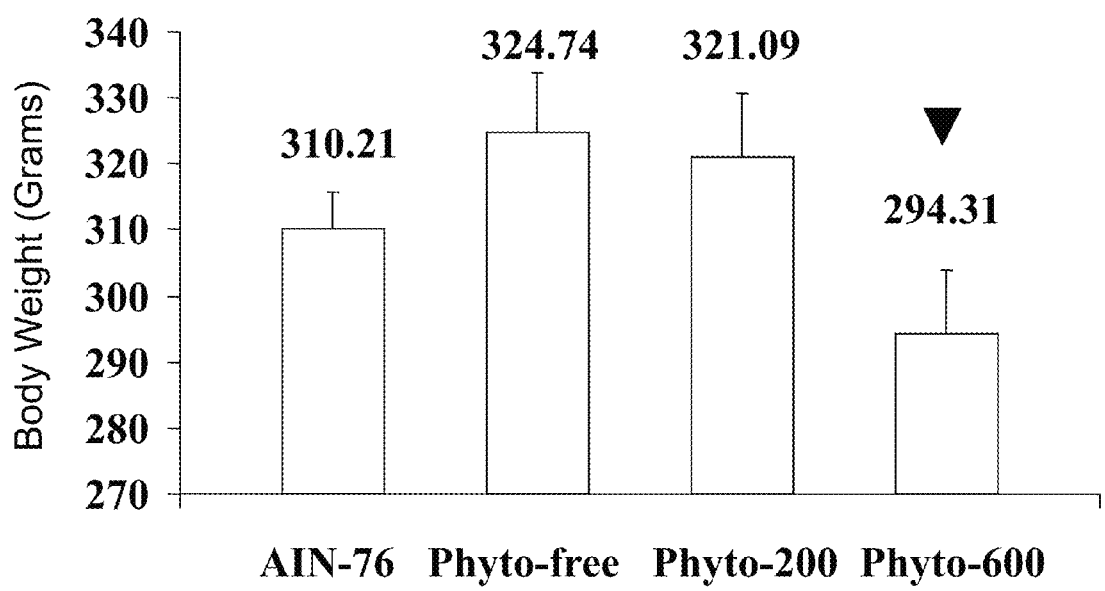
FIG. 37 shows body weights of 112-day-old female rats fed AIN-76, Phyto-Free, Phyto-200, or Phyto-600 diets.

To determine the influence of the four diet treatments on body weight in female rats, the body weights are measured at 112 and 279 days of age. At 112 days of age, females fed the Phyto-Free and the Phyto-200 diets have the heaviest body weights and the Phyto-600-fed females have the lowest, while the AIN-76 diet group fall in between the values of the other three groups, shown in FIG. 37. Body weights of the Phyto-600-fed groups are significantly lower, by approximately 10%, compared to the Phyto-Free- and the Phyto-200-fed females.

Figure 38:
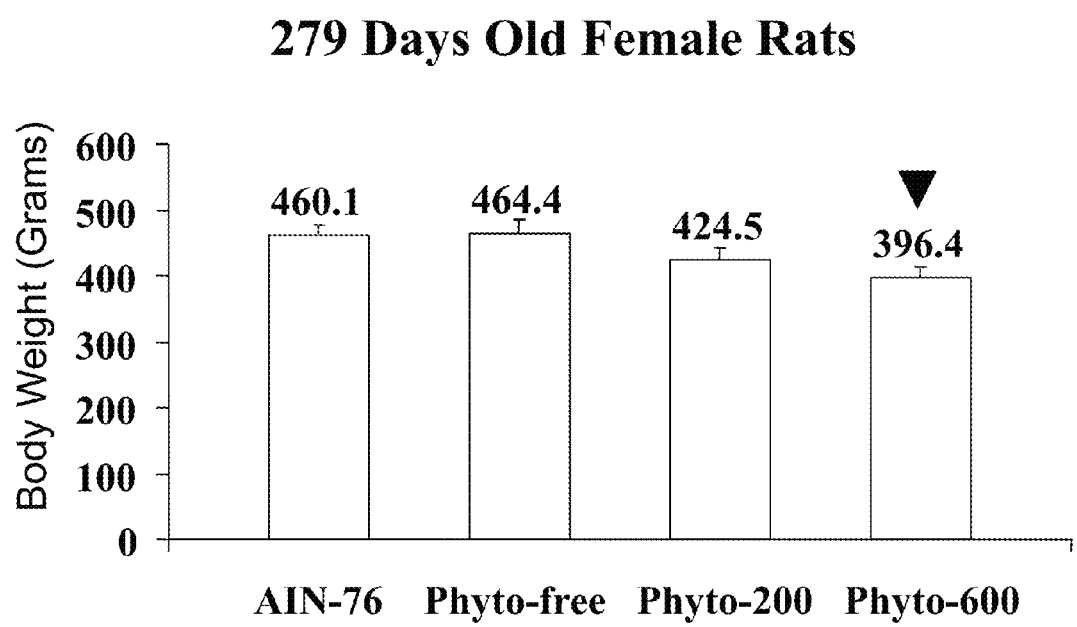
FIG. 38 shows body weights of 279-day-old female rats fed AIN-76, Phyto-Free, Phyto-200, or Phyto-600 diets.

At 279 days of age, female rats have a similar profile to that of age-matched males for changes in body weight as influenced by the diet treatments, shown in FIG. 38. Females fed the Phyto-600 diet display the lowest body weights compared to AIN-76 or Phyto-Free-fed groups. This significant reduction in body weight in Phyto-600-fed females is approximately 15% between the diet treatment groups tested.

Example 12

Noble rats were used to determine whether an inbred strain of rat has body and adipose tissue changes similar to those of out-bred strains of rats such as the Long-Evans animals when placed on isoflavone-rich diets. Due to inbreeding, Noble rats are more fragile animals. For example, pregnant dams do not always carry their litters to term and frequently have smaller litters. Noble rats have been used for more than twenty years because they spontaneously generate tumors with aging, especially in hormonal-dependent organs of the reproductive tract. Thus, Noble rats have been extensively studied in the area of cancer research (e.g., R. L. Noble, Prostate carcinoma of the Nb rat in relation to hormones, Int Rev Exp Pathol, 1982, 23:113-159).

Figure 39:
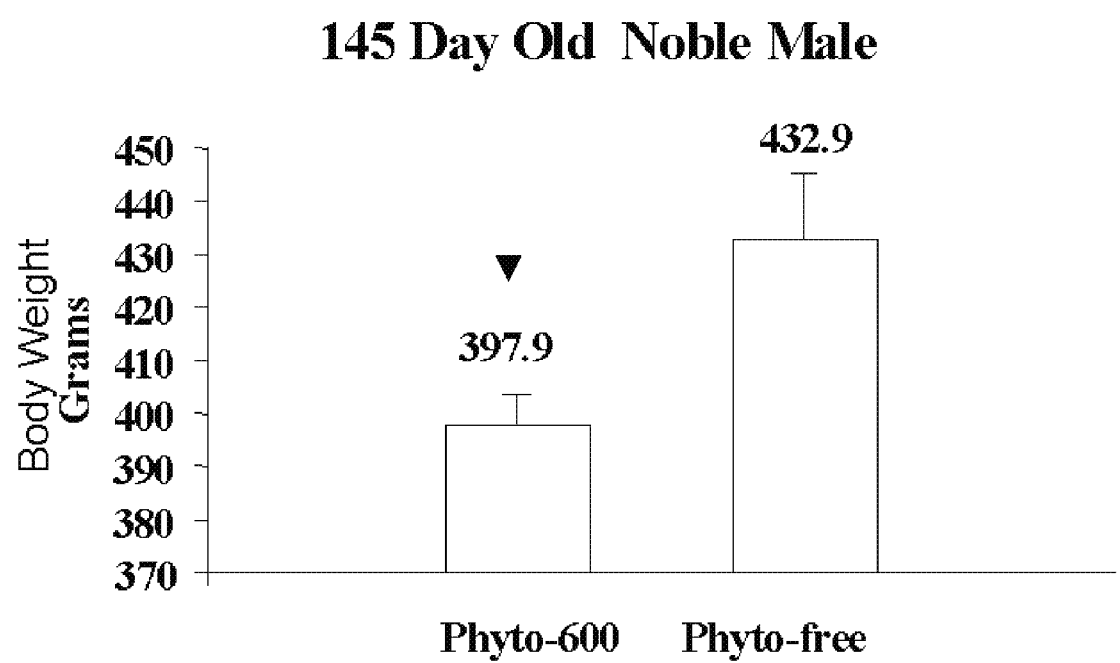
FIG. 39 shows body weights of 145-day-old male Noble rats fed Phyto-Free or Phyto-600 diets.
Figure 40:
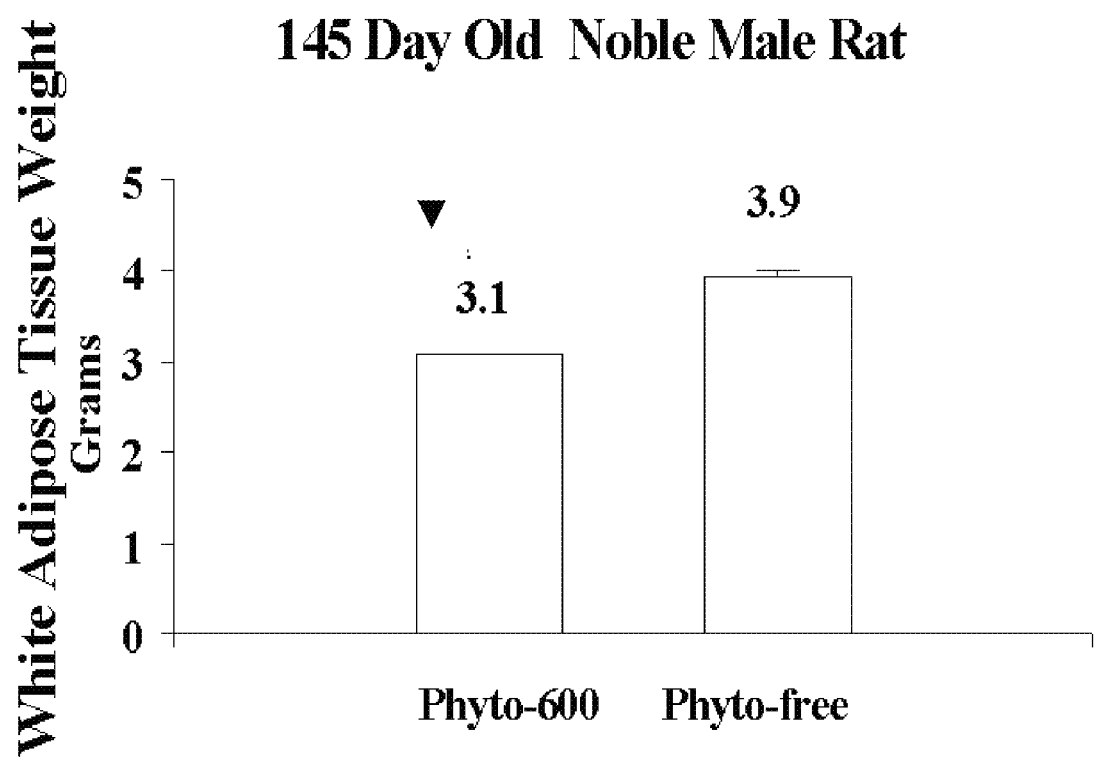
FIG. 40 shows white adipose tissue mass from 145-day-old male Noble rats fed Phyto-Free or Phyto-600 diets.

Male and female Noble rats are fed either the Phyto-Free or Phyto-600 diets from conception until 145 days of age. Male Noble rats fed the Phyto-600 diet have significantly lower body weights at 145 days of age compared to age-matched males fed the Phyto-Free diet, shown in FIG. 39. As previously observed for Long-Evans rats, the significant reduction in body weight represents a modest but consistent decrease of approximately 8% compared to Phyto-Free-fed males. In addition, white adipose tissue mass is significantly decreased in Phyto-600-fed males compared to Phyto-Free-fed, shown in FIG. 40.

Figure 41:
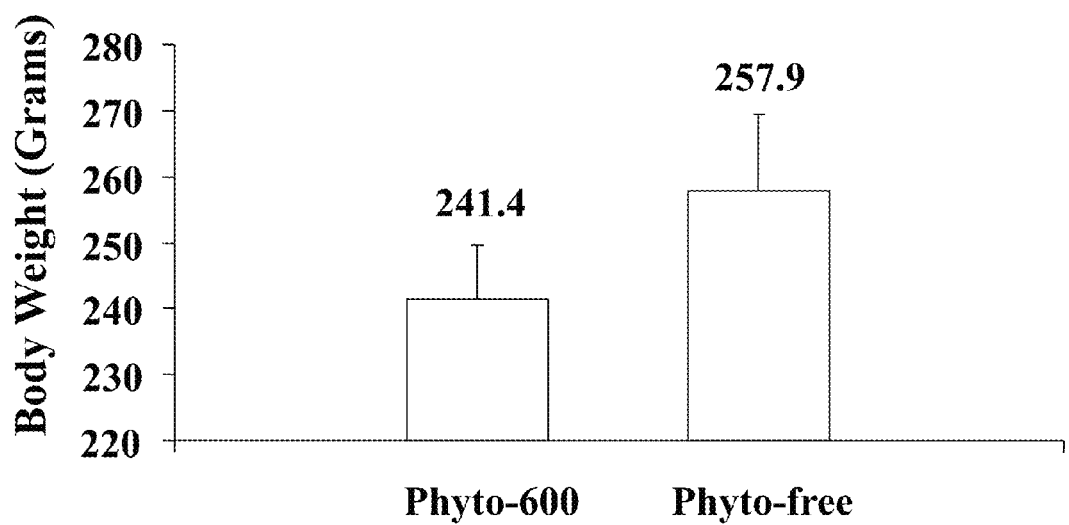
FIG. 41 shows body weights of 145-day-old female Noble rats fed Phyto-Free or Phyto-600 diets.
Figure 42:
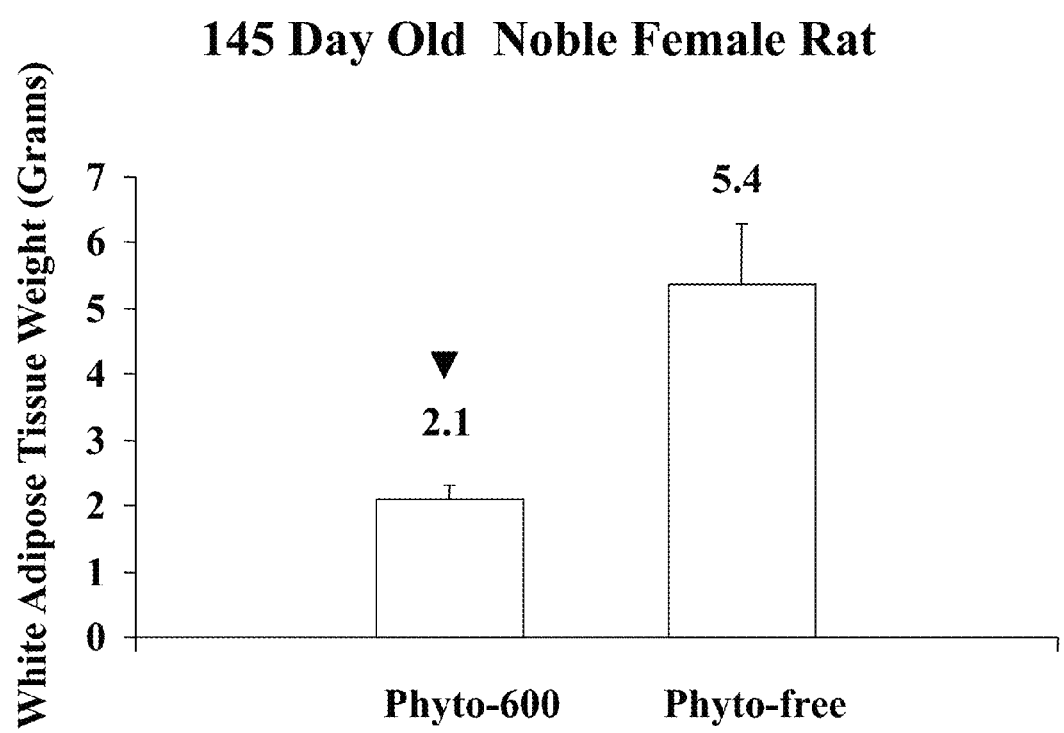
FIG. 42 shows white adipose tissue mass from 145-day-old female Noble rats fed Phyto-Free or Phyto-600 diets.

Female Noble rats fed the Phyto-600 diet have a 6% reduction in body weight compared to Phyto-Free-fed females, shown in FIG. 41. White adipose tissue mass is markedly decreased female Noble rats fed the Phyto-600 diet, shown in FIG. 42. The Phyto-600 diet group has a 61% reduction in adipose tissue compared to Phyto-Free-fed rats. The decrease in white adipose tissue is similar to that seen in Long-Evans rats.

Example 13

Figure 43:
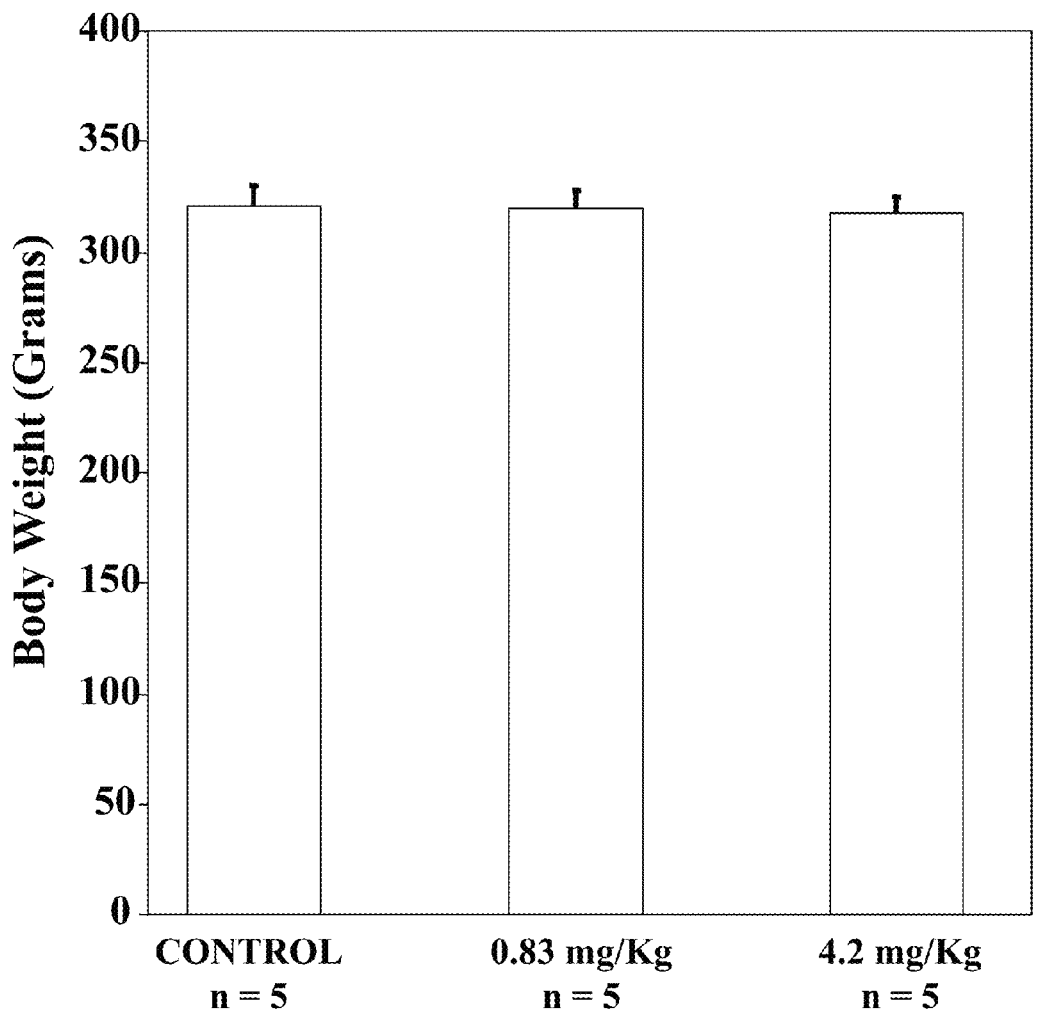
FIG. 43 shows baseline body weights of three groups of rats on a Phyto-Free diet prior to receiving equol injections.
Figure 44:
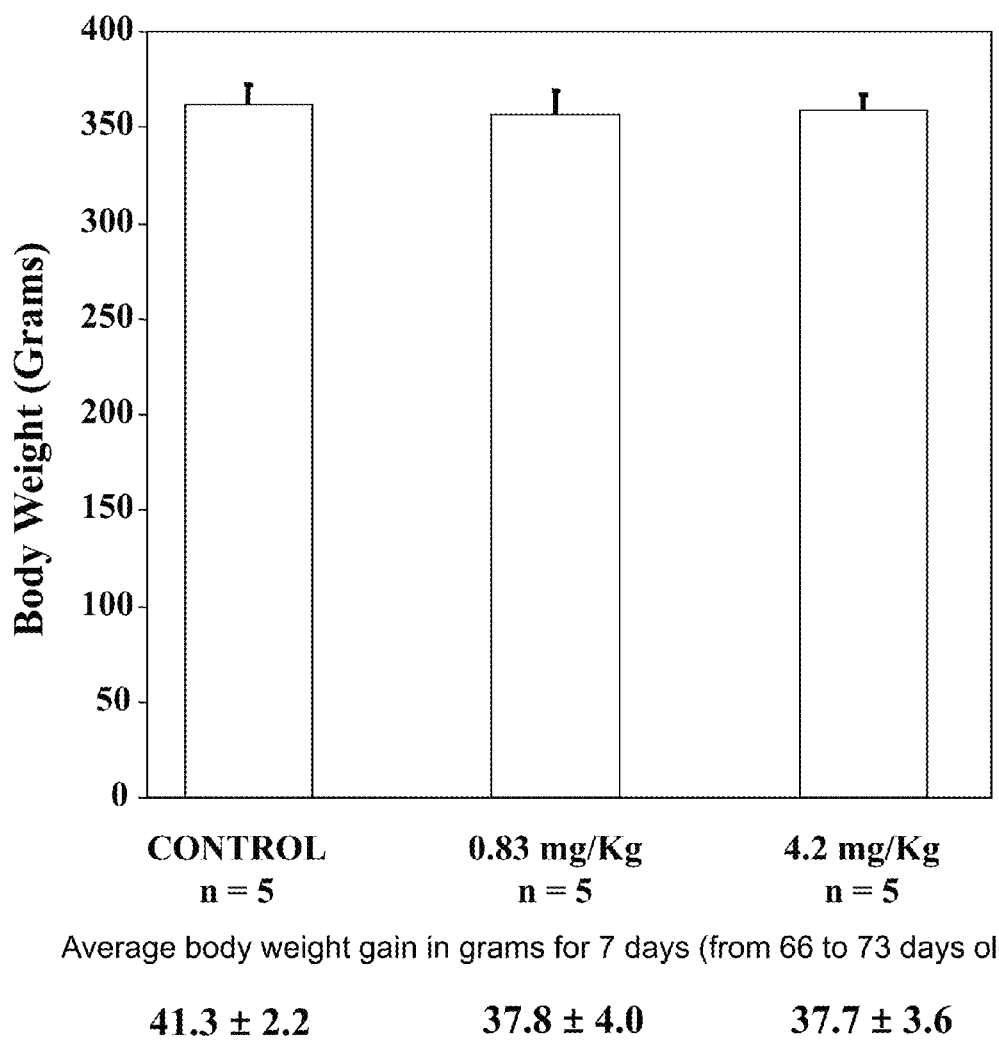
FIG. 44 shows body weights of three groups of rats after 21 days on a Phyto-Free diet prior to receiving equol or vehicle injections.

Prior to initiation of a Phyto-Free diet period Male Long-Evans rats are fed a Phyto-200 diet, as described in previous examples. The rats are placed on a diet containing the Phyto-Free diet at approximately 52 days of age and randomly assigned to three groups. Baseline body weights after 14 days and 21 days on the Phyto-Free diet for all rats are similar, shown in FIGS. 43 and 44, respectively. Beginning at 73 days of age, rats receive daily subcutaneous 0.1 cc injections of vehicle (peanut oil), 1 milligram of a racemic mixture of equol in vehicle (0.83 mg/kg body weight/day), or 5 milligrams of a racemic mixture of equol in vehicle (4.2 mg/kg body weight/day) once every three days.

Figure 45:
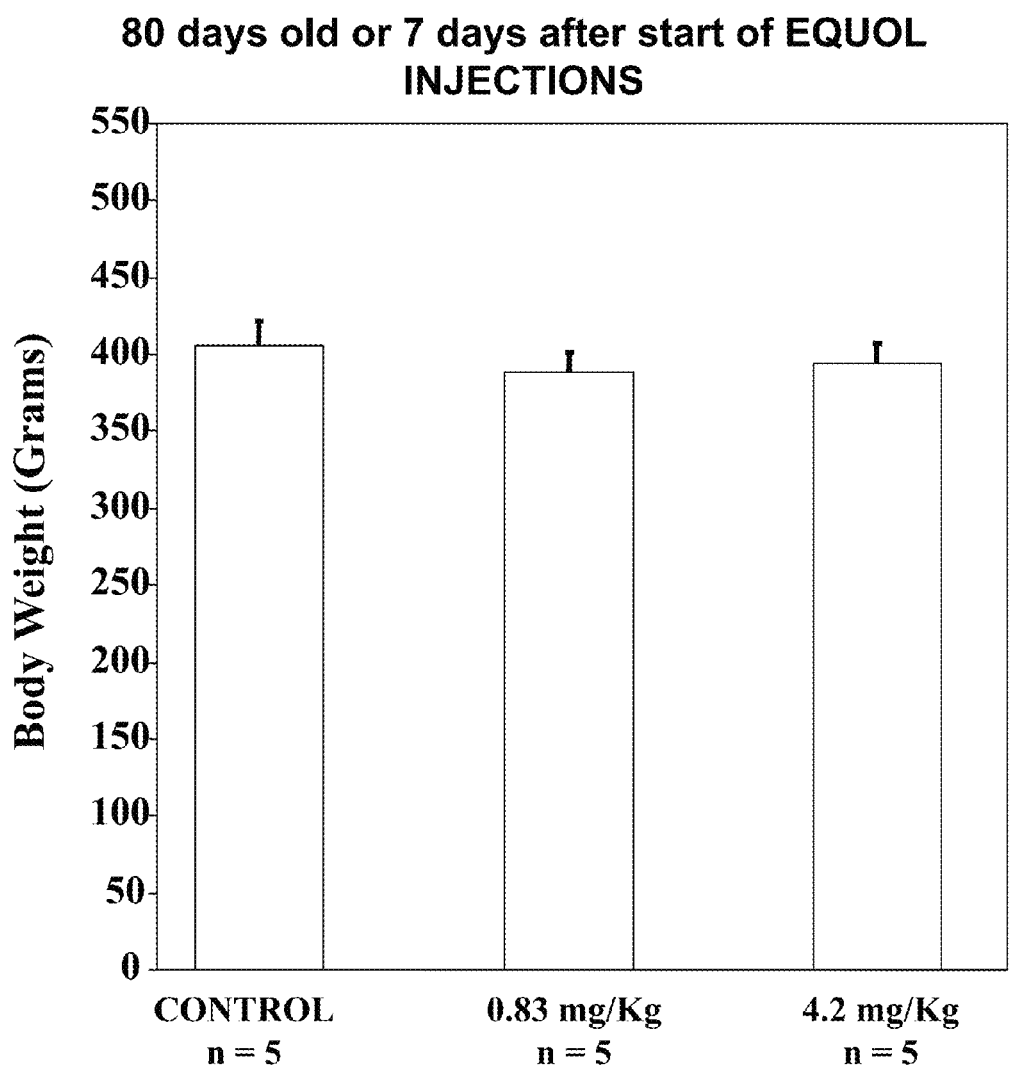
FIG. 45 shows body weights of three groups of rats on a Phyto-Free diet 7 days after receiving equol or vehicle injections.
Figure 46:
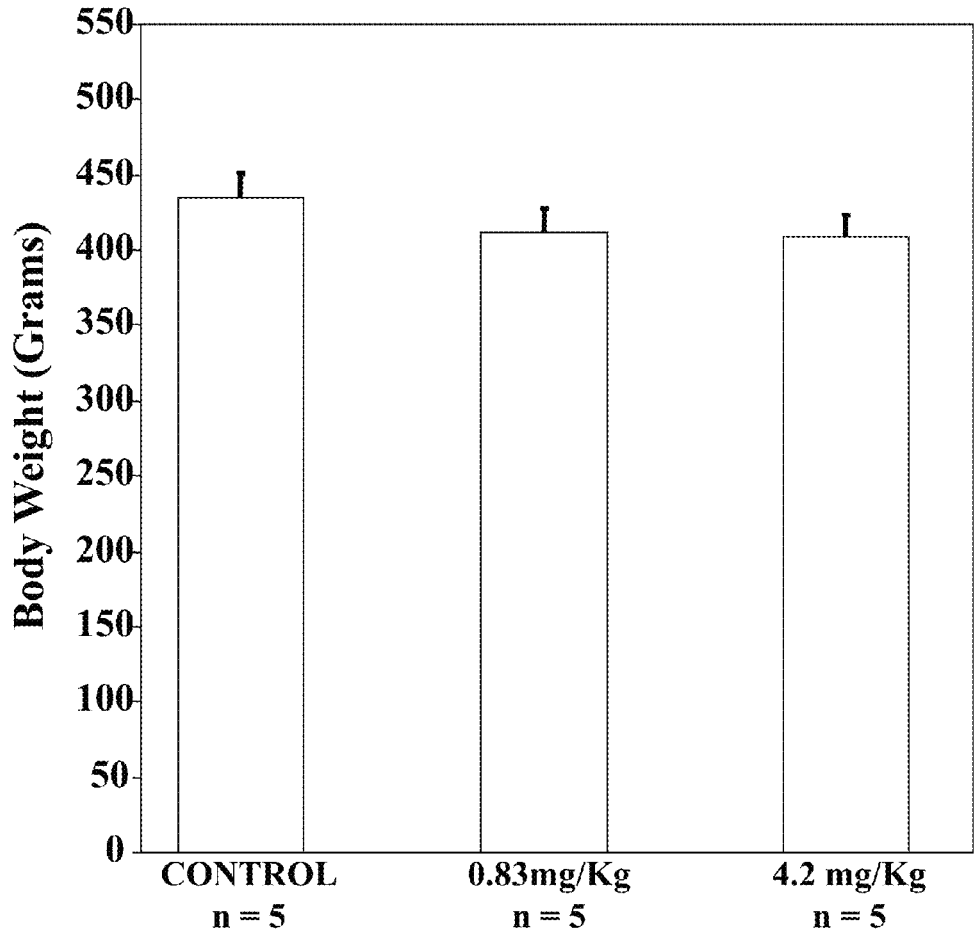
FIG. 46 shows body weights of three groups of rats on a Phyto-Free diet 15 days after receiving equol or vehicle injections.

At 80 and 88 days of age, there are slight decreases in body weights and average body weight gains in both equol-injected groups compared to controls, however, these values are not significantly different from controls, shown in FIGS. 45 and 46, respectively.

Figure 47:
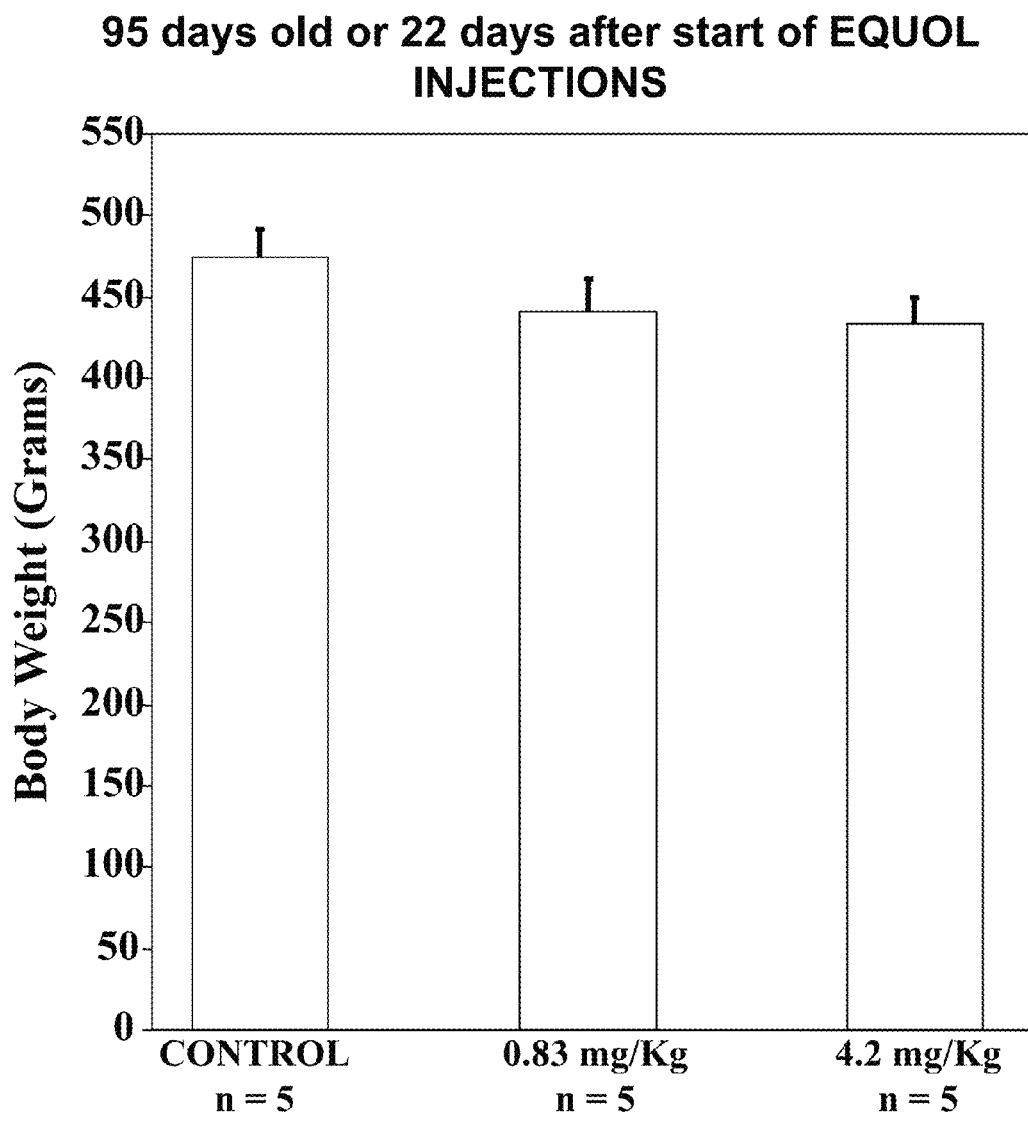
FIG. 47 shows body weights of three groups of rats on a Phyto-Free diet 22 days after receiving equol or vehicle injections.
Figure 48:
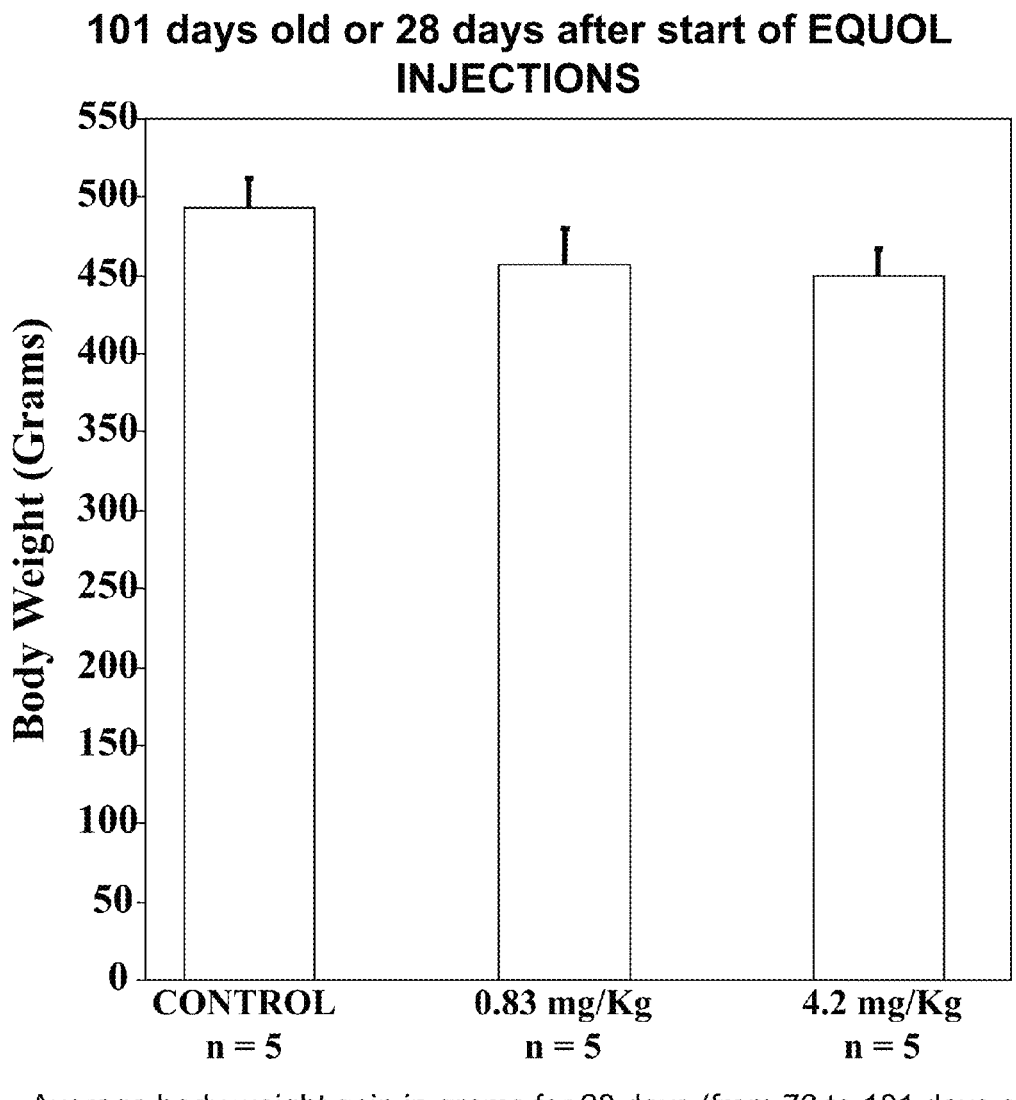
FIG. 48 shows body weights of three groups of rats on a Phyto-Free diet 28 days after receiving equol or vehicle injections.
Figure 49:
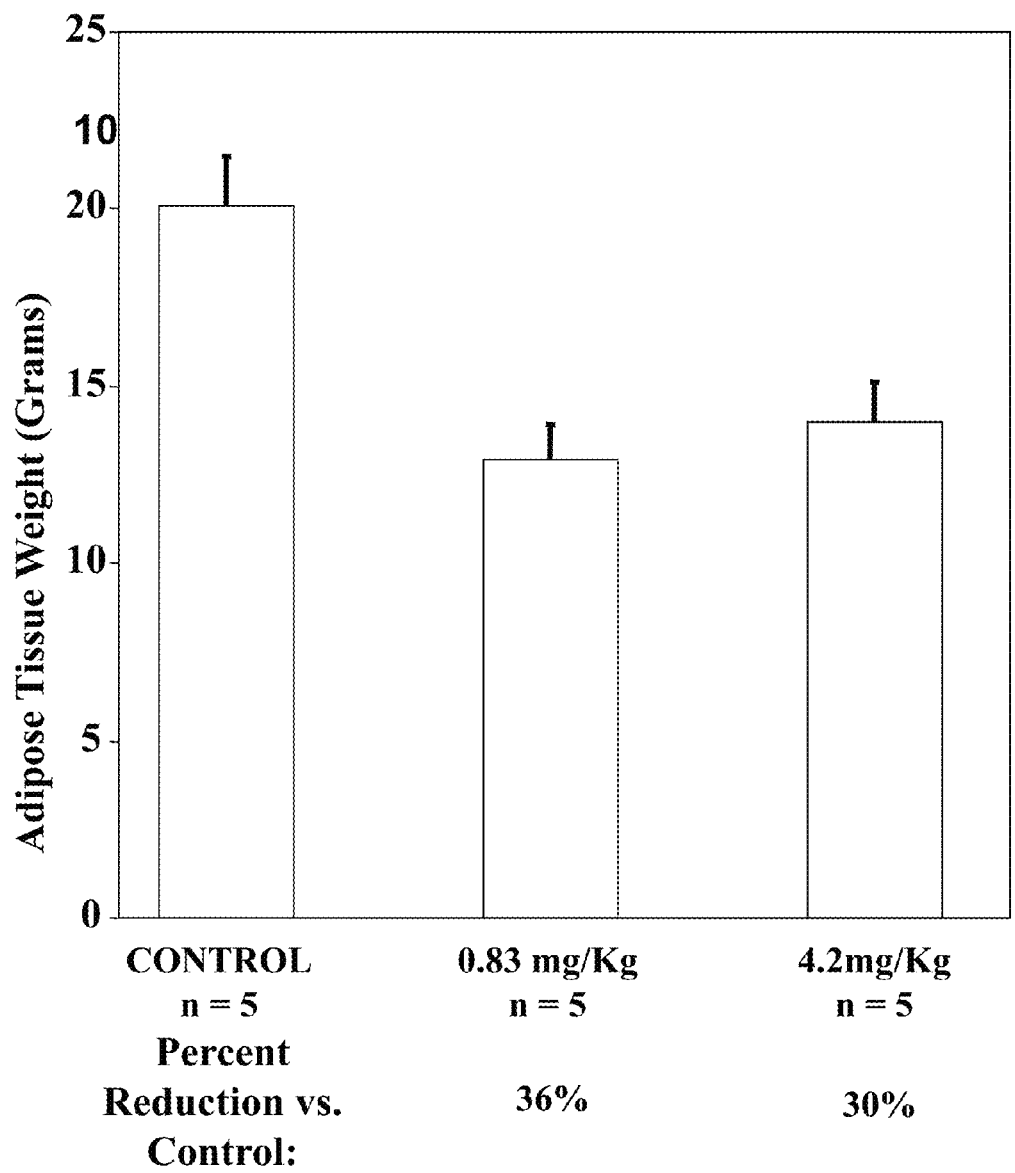
FIG. 49 shows adipose tissue mass from three groups of rats on a Phyto-Free diet 28 days after receiving equol or vehicle injections.

By the time the animals are 95 and 101 days of age, body weights are only slightly decreased, ranging from 5 to 9% in equol-treated groups, shown in FIGS. 47 and 48. However, the average body weight gains in equol-injected animals at both 95 and 101 days are significantly reduced compared to control values. Though body weight differences are not significant, adipose tissue deposition is strikingly lower in equol-treated groups. Adipose tissue mass in 101-day-old rats injected with equol is reduced by approximately 33% compared to controls, shown in FIG. 49.

Figure 50:
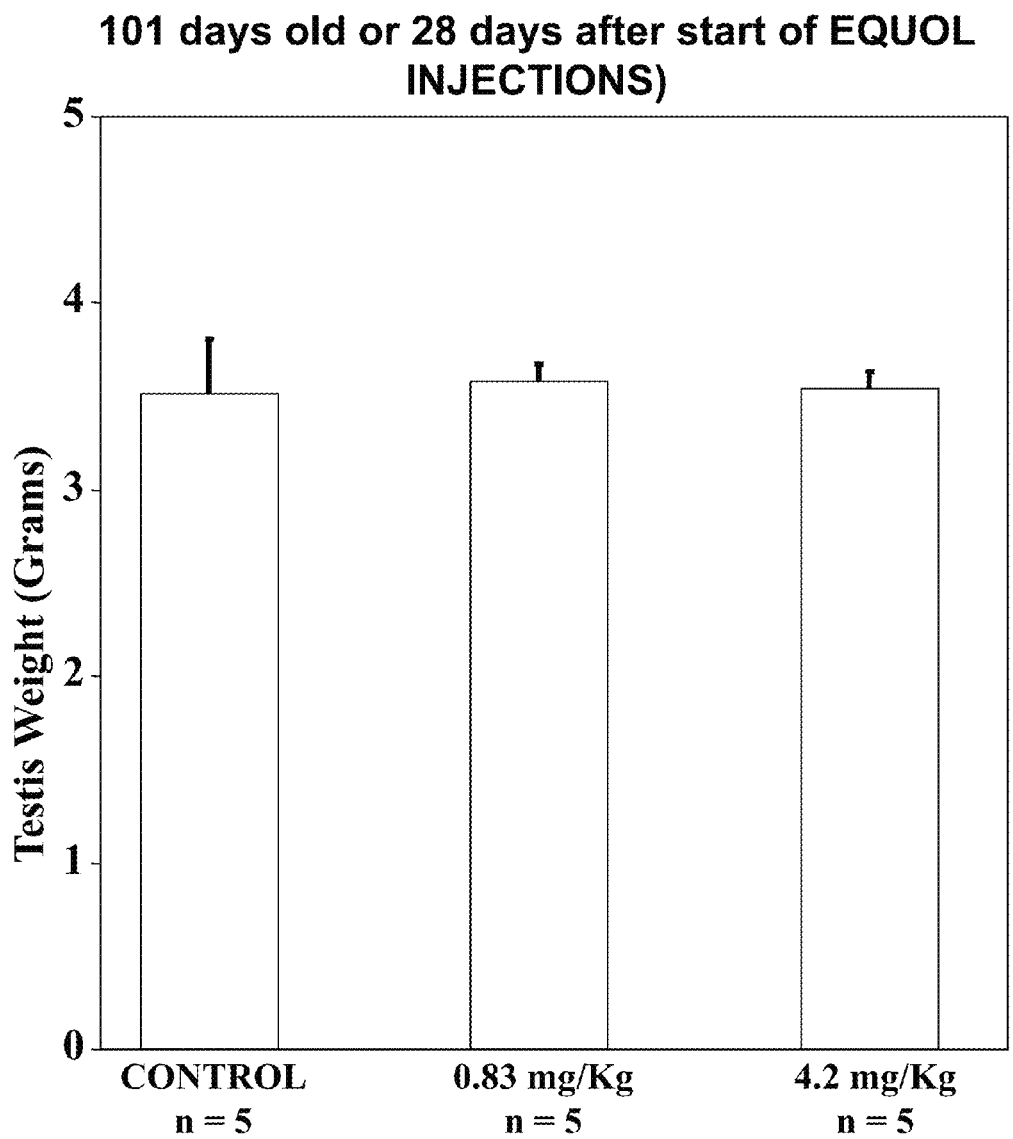
FIG. 50 shows testes weight from three groups of rats on a Phyto-Free diet 28 days after receiving equol or vehicle injections.

To determine whether equol injections have an adverse effect on male reproductive organs, testis weights are quantified in these animals. There are no significant alterations in testes weight with the equol injections, with testicular weight essentially the same among the injection treatment groups, shown in FIG. 50.

Example 14

Fifty day-old Long-Evans males and females are caged individually and maintained on a 10-hour dark 14-hour light schedule (lights on 1400-0400). Animals are randomly assigned to diet groups, and allowed ad libitum access to one of four diet treatments: 1) AIN-76, 2) Phyto-Free, 3) Phyto-200, or 4) Phyto-600 diet. The rats remain on the diets until mid-aged (at approximately 300 days of age in males and at approximately 330 days of age in females) when the animals are tested in the elevated plus maze and anxiety-related behaviors were quantified. Thereafter, serum phytoestrogen levels are quantified by GC/MS according to the method described by Coward L et al, J Agric Food Chem, 41:1961-1967. The behavioral patterns of anxiety are compared to the serum profiles of circulating isoflavone levels in the diet treatment groups by sex.

Figure 51:
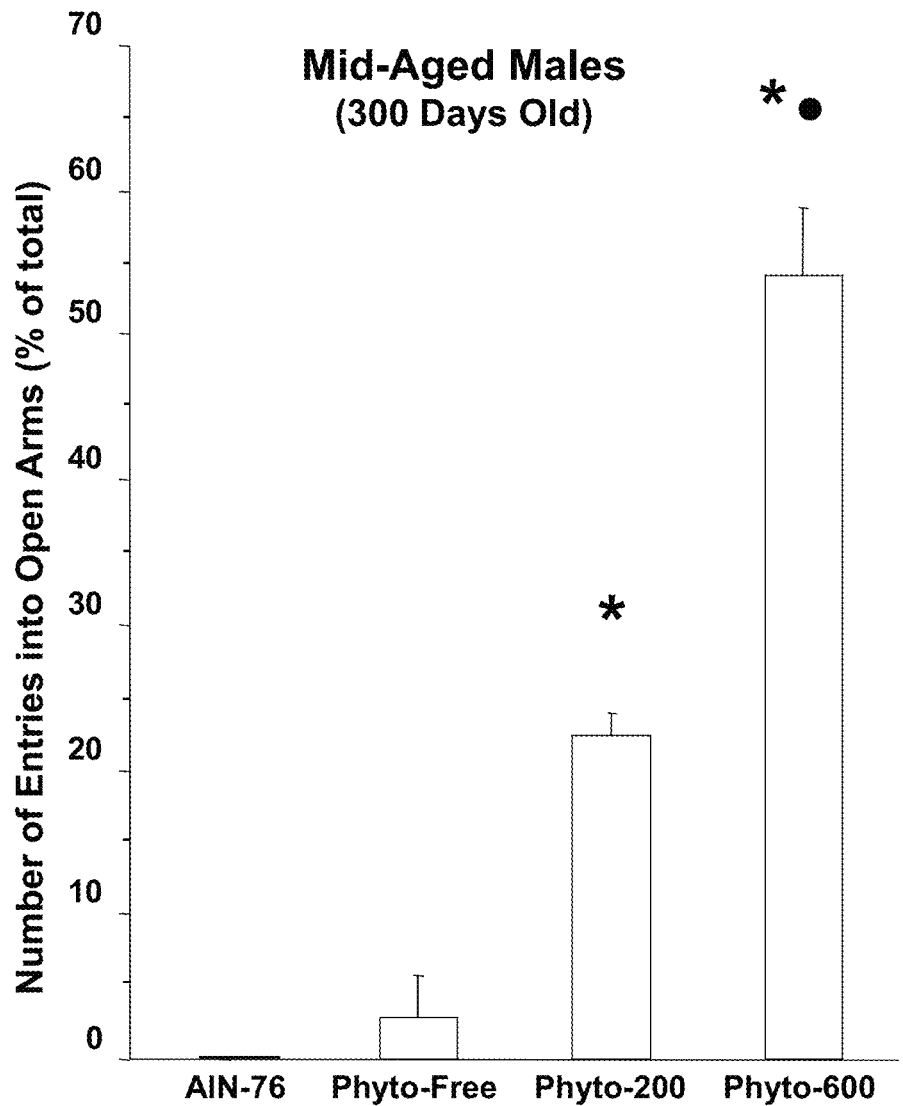
FIG. 51 shows number elevated-plus maze anxiety-related behavior (entries into open arms) of 300-day-old male rats fed 4 different diets.
Figure 52:
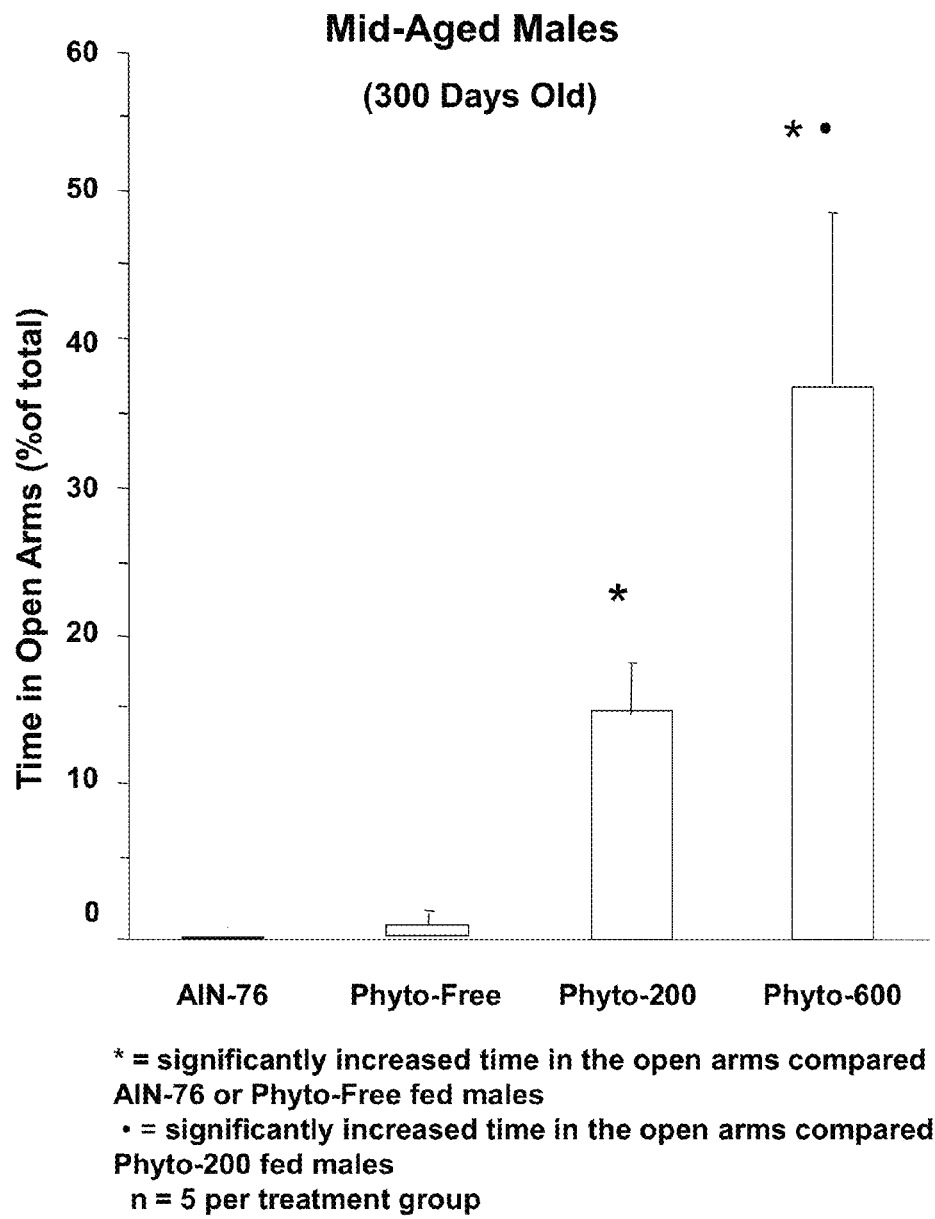
FIG. 52 shows elevated-plus maze anxiety-related behavior (time in open arms) of 300-day-old male rats fed 4 different diets.

In males, there is a dose-dependent expression of anxiety-related behaviors where animals fed the highest concentration of isoflavones display the lowest anxiety parameters. In contrast, animals fed the AIN-76 diet display the highest levels of anxiety, shown in FIG. 51. When the percent of time spent in the open arms is analyzed a similar pattern is seen to that of the number of entries into the open arms. Notably, the Phyto-600 fed males display the highest percentage of time spent in the open arms, while the lowest percentage of time spent in the open arms is display by animals fed the AIN-76 diet, with Phyto-free and Phyto-200 values falling in between these maximal responses in a dose-dependent fashion, shown in FIG. 52.

Figure 53:
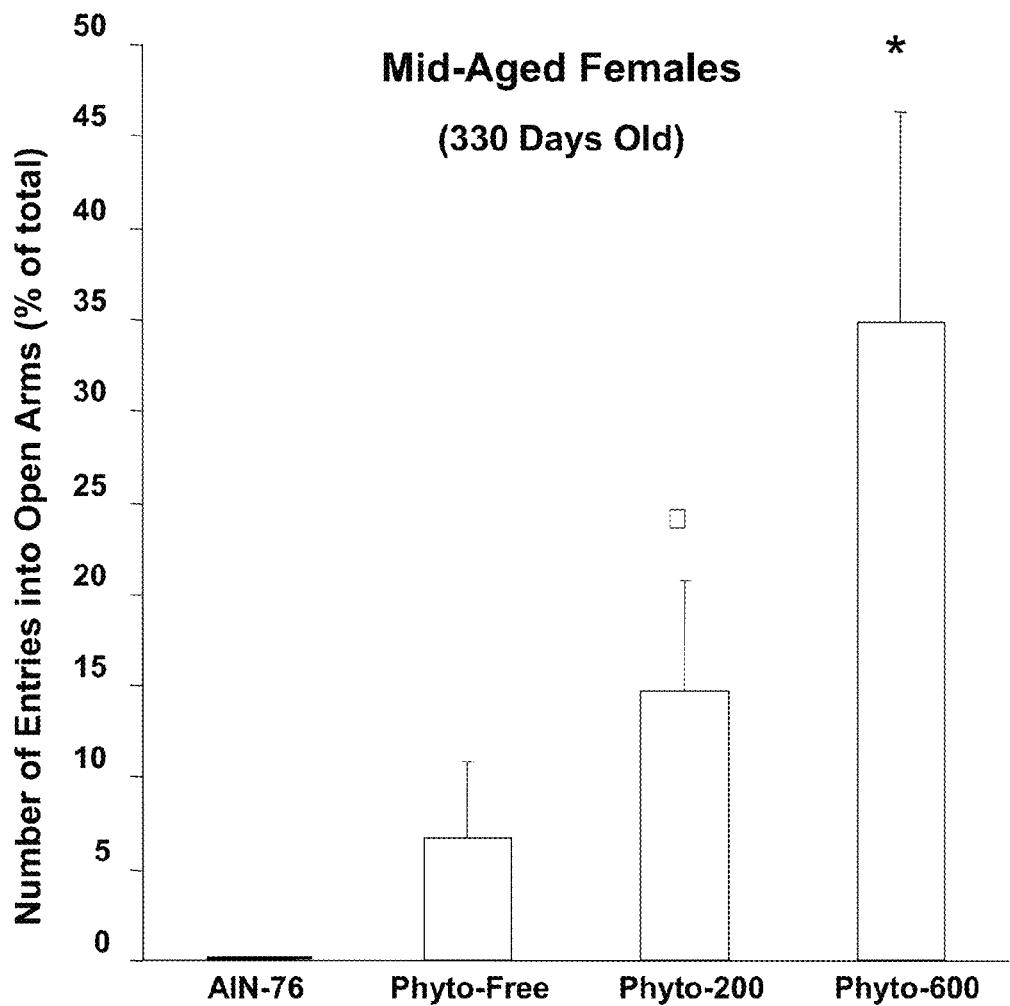
FIG. 53 shows elevated-plus maze anxiety-related behavior (entries into open arms) of 330-day-old female rats fed 4 different diets.
Figure 54:
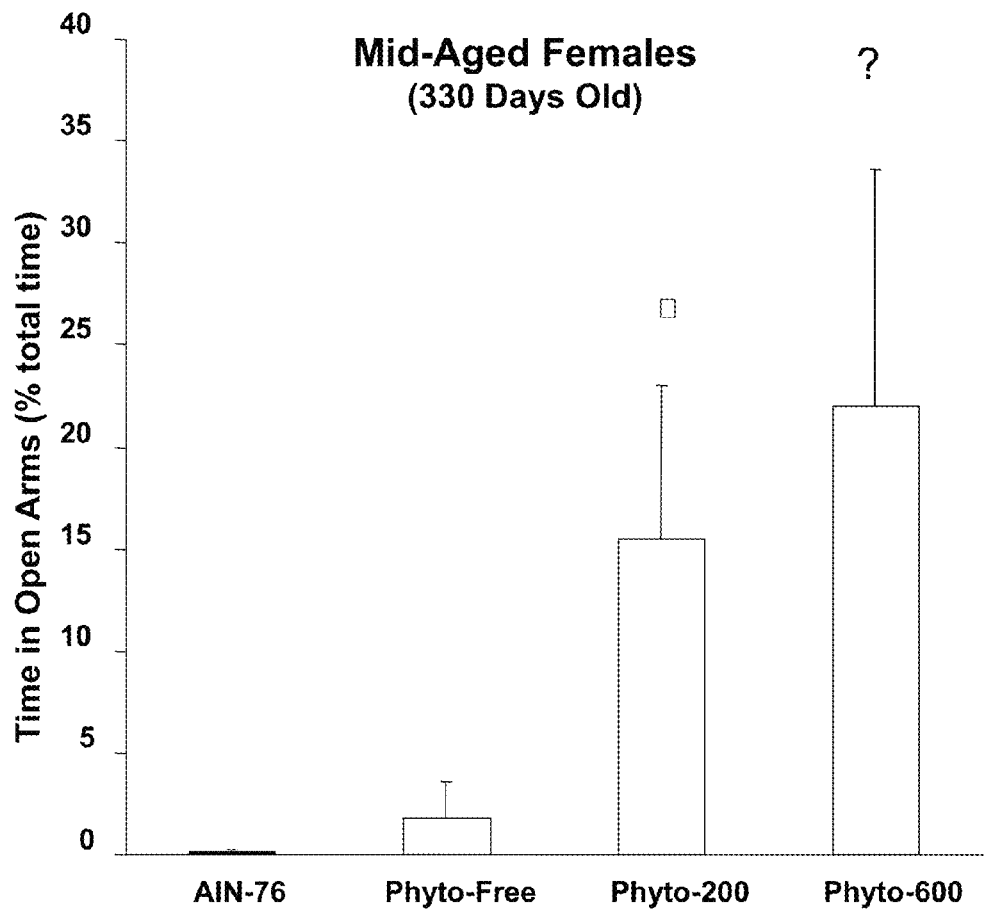
FIG. 54 shows elevated-plus maze anxiety-related behavior (time in open arms) of 330-day-old female rats fed 4 different diets.

Prior to testing in the elevated plus maze, females are monitored by vaginal smears for 12 consecutive days to verify that none are cycling to minimize effects of the estrous cycle. Female rats have a similar pattern of anxiety-related behaviors as those observed in the male rats. However, the influence of dietary isoflavones is not as robust as that seen in males. Although, the highest percentage of the number of entries into (FIG. 53) or time spent on the open arms (FIG. 54) is seen in Phyto-600-fed females, with a stair-step pattern of decline until the lowest percentage of entries is seen in the AIN-76-fed females.

Figure 55:
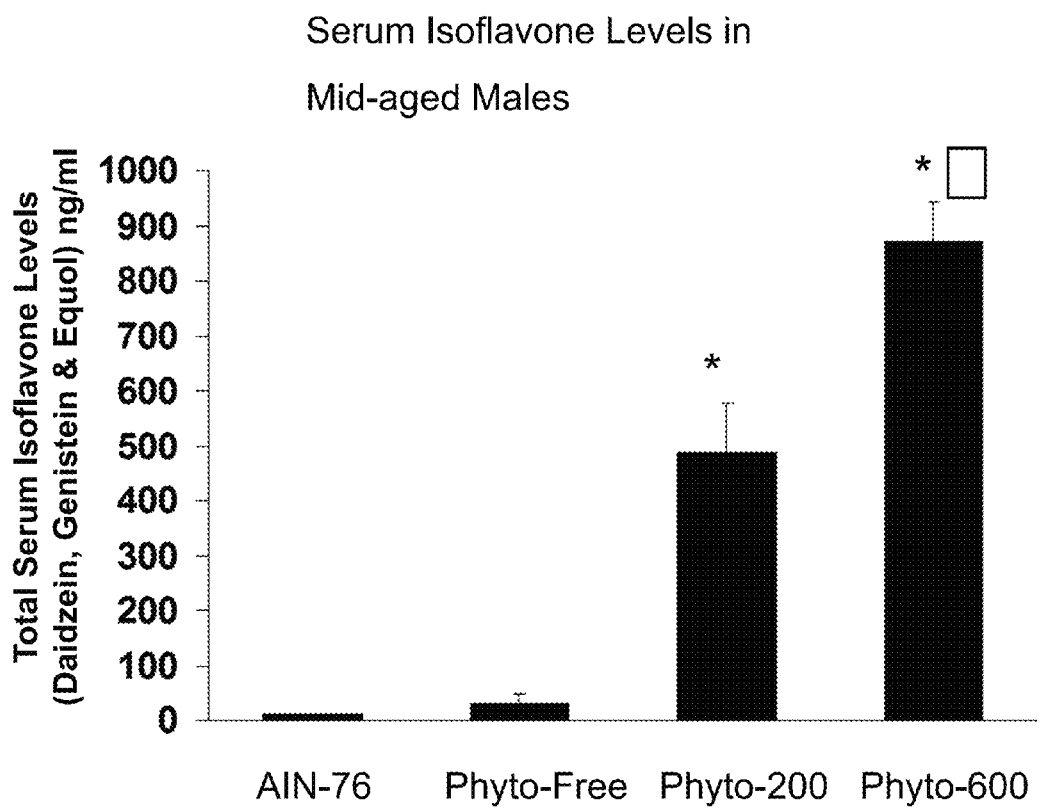
FIG. 55 shows serum isoflavone levels in 300-day-old male rats fed 4 different diets.
Figure 56:
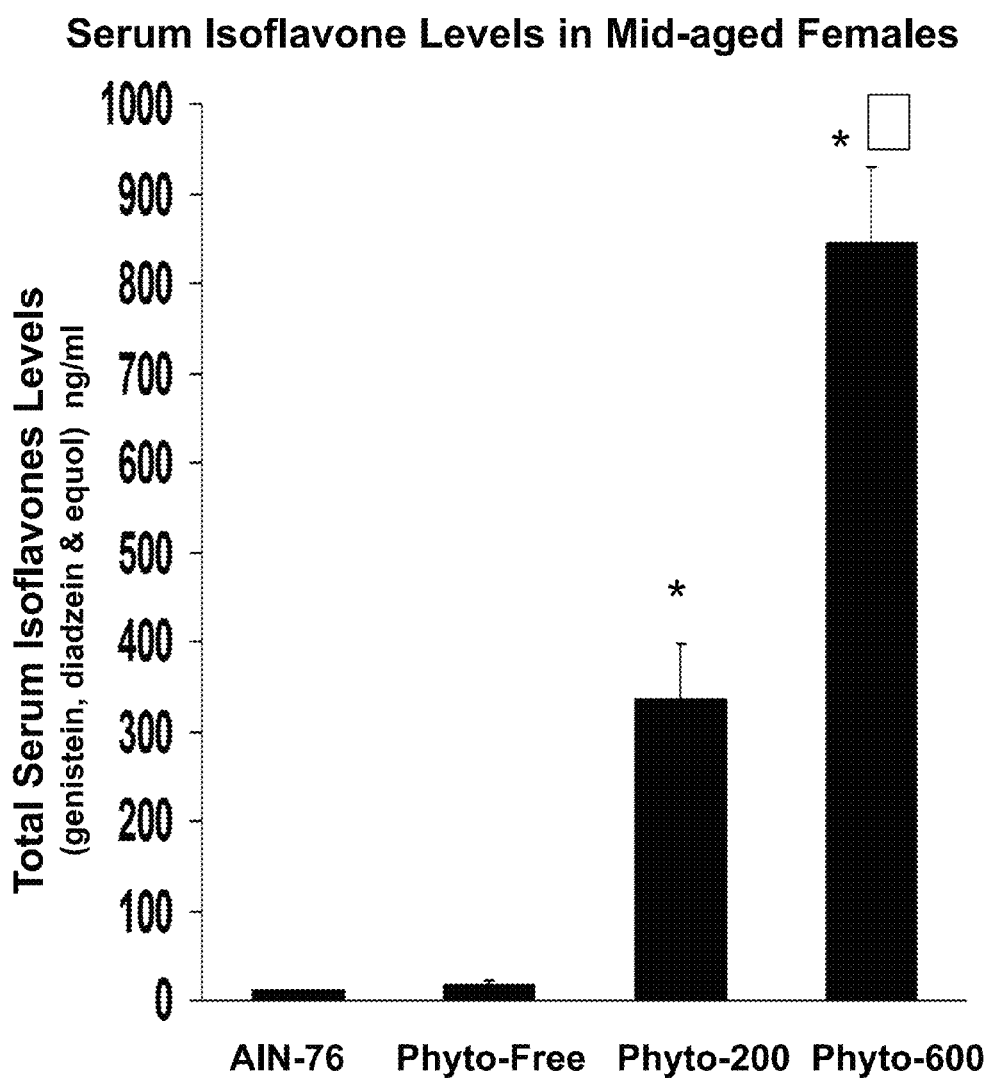
FIG. 56 shows serum isoflavone levels in 330-day-old female rats fed 4 different diets.

When behavioral testing is complete, the serum phytoestrogen levels are determined and compared to the patterns of anxiety-related behaviors. In both males (FIG. 55) and females (FIG. 56), the circulating isoflavone levels correspond to the expression of anxiety-related behaviors, demonstrating an association between circulating isoflavone molecules and anxiety. These data demonstrate that the isoflavone content of a diet can have significant effects on anxiety.

Example 15

Adult male Sprague-Dawley rats receive daily injections of either DMSO, racemic equol (0.250 mg/Kg/day), R-equol (0.250 mg/Kg/day), or S-equol (0.250 mg/Kg/day) in a total volume of 0.3 cc DMSO by subcutaneous injection. At the end of seven consecutive days of treatment the animals are tested in the elevated plus maze in order to quantify anxiety-related behaviors. As shown in Table 5 below, males injected with racemic equol or R-equol display a significant decrease in anxiety levels compared to control rats.

TABLE 5

Anxiety-Related Behaviors in the Elevated Plus Maze of Equol Injected Male Rats.

| Injection Treatment Groups | Center Area (in seconds) | Open Arm Time (in seconds) | Open Arm Entries (in seconds) |
|---|---|---|---|
| DMSO | 17.5 + 4.1 | 16.3 + 4.0 | 1.0 + 0.03 |
| Equol (racemic) | 37.1 + 6.3* | 40.9 + 7.0* | 2.3 + 0.4* |
| R-Equol | 36.4 + 7.6 | 50.0 + 10.0* | 2.0 + 0.3* |
| S-Equol | 27.5 + 4.1 | 33.6 + 7.0 | 2.0 + 0.4** |

*= significant decrease in anxiety-related parameters (i.e., center area of maze time or time spent in the open arms or number of open arm entries) vs. control values.
**= significant decrease in anxiety-related behavior (i.e., number of open arm entries) vs. control values.
n = 8 animals per group.

These findings are consistent with those obtained utilizing the 4 dietary treatments containing different concentrations of isoflavones, and demonstrate that equol is a major factor in regulating anxiety and other neurological states such as mood and depression that have obvious potential for broad health benefits.

Example 16

Figure 57:
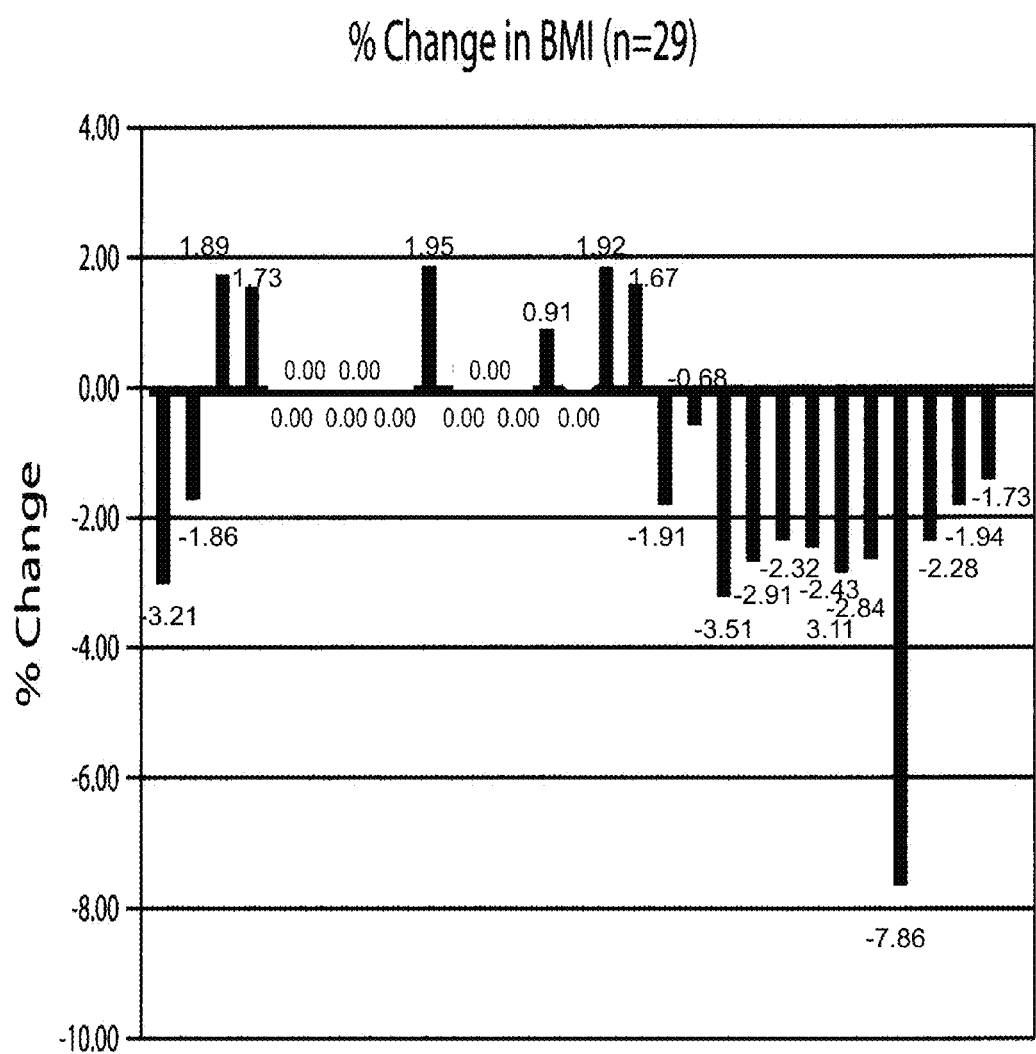
FIG. 57 shows the observed change in BMI for individuals after 5 weeks of strict adherence to a diet containing isoflavones.

Twenty-nine (29) adults with hypercholesterolemia are fed a diet containing 33 mg of total isoflavones daily for 5 weeks. FIG. 57 shows the observed change in BMI for each of the 29 individuals after 5 weeks of strict adherence to the diet containing isoflavones. The average reduction in BMI over this period, although small, is nevertheless significant (p=0.01). These results suggest that phytoestrogen-rich diets can influence weight control in humans. The study did not identify the component(s) responsible or the mechanism of weight control. Average baseline BMI (n=29) is 26.6±0.8, and the average BMI (n=29) at 5 weeks is 26.2±0.7.

While various embodiments of the present invention have been described in detail, it will be apparent that further modifications and adaptations of the invention will occur to those skilled in the art. It is to be expressly understood that such modifications and adaptations are within the spirit and scope of the present invention.

We claim:

1. A method for treating or preventing a physiological or pathophysiological conditions of benign prostatic hyperplasia and prostate cancer and mediated by androgens in a mammal comprising:
    administering to the mammal an effective amount of a composition consisting of:
        equol comprising a racemic mixture of R-equol and S-equol enantiomers; and
        at least one of a pharmaceutically, nutraceutically, or cosmetically acceptable carrier, adjuvant, or excipient,
    thereby treating or preventing the physiological and pathophysiological conditions of benign prostatic hyperplasia and prostate cancer.

2. The method of claim 1, wherein the equol is in a pharmaceutical.

3. The method of claim 1, wherein the equol is in an over-the-counter medicament.

4. The method of claim 1, wherein the equol is in a food product.

5. The method of claim 1, wherein the composition comprises at least 1 mg equol for oral administration.

* * * * *